(12) United States Patent
Jung

(10) Patent No.: US 6,399,808 B1
(45) Date of Patent: Jun. 4, 2002

(54) EFFICIENT CARBAMATE SYNTHESIS

(75) Inventor: Kyung Woon Jung, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/513,691

(22) Filed: Feb. 25, 2000

Related U.S. Application Data

(60) Provisional application No. 60/121,867, filed on Feb. 26, 1999, provisional application No. 60/126,151, filed on Mar. 25, 1999, provisional application No. 60/138,656, filed on Jun. 14, 1999, and provisional application No. 60/149,905, filed on Aug. 23, 1999.

(51) Int. Cl.$^7$ ..................... C07C 229/02; C07C 271/00
(52) U.S. Cl. ........................... 560/19; 560/24; 560/125
(58) Field of Search ............................. 560/19, 24, 125

(56) References Cited

U.S. PATENT DOCUMENTS 4,550,188 A * 10/1985 Frulla et al. .................. 560/24
5,698,731 A * 12/1997 Bosetti et al. ................ 560/24

OTHER PUBLICATIONS

Li et al (1997): Bioorganic & Medicinal Chemistry Letters, vol. 7, 2909–2912.*
Chu et al (1999): Tetrahedron Letters, vol. 40, 1847–1850.*

* cited by examiner

*Primary Examiner*—T. A. Solola
*Assistant Examiner*—Golam M. M. Shameem
(74) *Attorney, Agent, or Firm*—Katten Muchin; Zavis Rosenman

(57) ABSTRACT

A method of preparing carbamates of the general formula RR'—N—CO$_2$—R" by reacting an amine with carbon dioxide and an organic electrophile in an anhydrous solvent in the presence of a cesium base, whereby carbamate synthesis is accomplished in good yield at mild temperatures, either in solution or on a solid support, and wherein R, R', and R" are hydrogen, alkyl of 1–18 carbon atoms, silyl, phenyl, benzyl, cyclopentyl, cyclohexyl, cycloheptyl, cyclooctyl, allyl, or heterocycle, which are widely used as industrial products, and as intermediates in organic synthesis.

19 Claims, 5 Drawing Sheets

EFFICIENT CARBAMATE SYNTHESIS

RELATED APPLICATIONS

The present application is related to U.S. Provisional Applications No. 60/121,867 filed Feb. 26, 1999, No. 60/126,151 filed Mar. 25, 1999, No. 60/138,656 filed Jun. 14, 1999, and No. 60/149,905 filed Aug. 23, 1999, each of which is herein incorporated by reference in its respective entirety.

1. FIELD OF THE INVENTION

The present invention relates to an efficient method for the synthesis of carbamates of the following general formula,

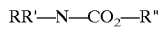

RR'—N—CO$_2$—R"

and N-alkylated derivatives thereof, wherein R, R', and R" are selected from the group consisting of hydrogen, alkyl of 1–18 carbon atoms, silyl, phenyl, benzyl, cyclopentyl, cyclohexyl, cycloheptyl, cyclooctyl, allyl, and heterocycles, which are widely used as industrial products, and as intermediates in organic synthesis. In particular, the invention relates to a method providing efficient formation of carbamates from amines, carbon dioxide, and an organic electrophile, in the presence of a cesium base and, optionally, tetrabutylammonium iodide.

2. BACKGROUND OF THE INVENTION

Carbamates are widely used in industry and research, for example as fungicides, pharmaceuticals, cosmetics, and antibacterial preparations; as intermediates and cleavable protective groups in organic synthesis; and as peptidomimetic compounds.

Carbamates are prepared by a variety of methods, in particular by reaction of amines with alkyl chloroformates; by reaction of alcohols with carbamoyl chlorides or isocyanates; via reactions involving metal complexes or acyl transfer agents; and in some cases by the use of the highly toxic, and inconvenient to handle, phosgene reagent. See for example, Greene, T. W. and Wuts, P. G. M., "Protective Groups in Organic Synthesis"; 1991; Wiley and Sons, p. 309–348.

The above methods suffer from certain drawbacks and limitations. Harsh reaction conditions, including elevated temperatures are often required to achieve acceptable yields of carbamate products. Use of harsh conditions complicates synthesis of compounds containing labile functional groups, requiring either additional protection/deprotection steps, or post-synthesis purification, thus lowering yields and increasing costs. Harsh reaction conditions can also promote inversion of chiral centers causing undesirable racemization of products. Furthermore, the reagents required are often toxic, for example isocyanates, or highly toxic, such as phosgene. In addition, activated compounds used in carbamate synthesis, such as acyl transfer agents, may be unstable. The latter problem is compounded when relatively unreactive aromatic amines are used. For each of these reasons, an improved method for the synthesis of carbamates has long been sought.

Carbon monoxide and certain metal catalysts can be used to synthesize carbamates from several starting compounds, including amines. Metals such as palladium, iridium, uranium, and platinum are used as catalysts. Not only are these metals expensive, but frequently a redox-active co-catalyst such as ferrous chloride is advantageous, which complicates purification and is corrosive.

Methods using carbon dioxide in place of the more toxic carbon monoxide for synthesis of carbamates have been reported, (see for example, Yoshida, Y., et al., *Bull. Chem. Soc. Japan* 1989, 62, 1534; and Aresta, M., et al., *Tetradedron*, 1991, 47, 9489) but such reactions often require harsh reaction conditions such as elevated temperatures.

Therefore, there exists a need for a method that simply and efficiently converts amines to carbamates in substantial yield. Furthermore, a desirable method would require less toxic and/or more stable reagents than are currently used. Preferably such a method could be performed under mild reaction conditions to minimize side reactions, and could provide for conversion of even poorly reactive amines, such as aromatic amines, both in solution and on solid supports.

BRIEF SUMMARY OF THE INVENTION

It is therefore an object of the present invention to provide an improved process for the conversion of amines to carbamates which avoids the aforementioned disadvantages and drawbacks.

It is a further object of the present invention to provide a process that obviates harsh reaction conditions, such as, but not limited to, reaction at high temperatures, or the presence of corrosive transition metal compounds.

It is a further object of the present invention to provide a process characterized by a three-component coupling of an amine, carbon dioxide, and an organic electrophile at mild temperatures in the presence of a cesium base.

It is a further object of the present invention to provide a simple and efficient method for the preparation of silylcarbamates.

It is yet a further object of the invention to provide methods for the synthesis of carbamate compounds upon a solid support matrix.

It is yet a further object of the invention to provide simple and efficient methods for selective synthesis of N-alkylated carbamates.

It is still a further object of the invention to provide methods for the synthesis of carbamates that avoid racemization and preserve the enantiomeric purity of the starting materials.

These and other objects of the present invention will become obvious to those skilled in the art upon review of the following disclosure.

Disclosed herein are methods for the conversion of amines that yield substantially carbamates; require reagents of lesser toxicity and higher stability than those agents set forth in the prior art; can be performed under mild reaction conditions to minimize side reactions; and provide for conversion of amines to carbamates both in solution and on solid supports. In a preferred embodiment, cesium carbonate, a source of carbon dioxide, an amine, and an alkyl halide are reacted in an anhydrous solvent. This catalytic process allows for the efficient and inexpensive preparation of various carbamates essential to industrial and research uses. Applications of the developed methodologies disclosed herewith include peptidomimetic synthesis, combinatorial library synthesis, drug design, protection of groups and the like.

DETAILED DESCRIPTION OF THE DRAWINGS

Figure 1:
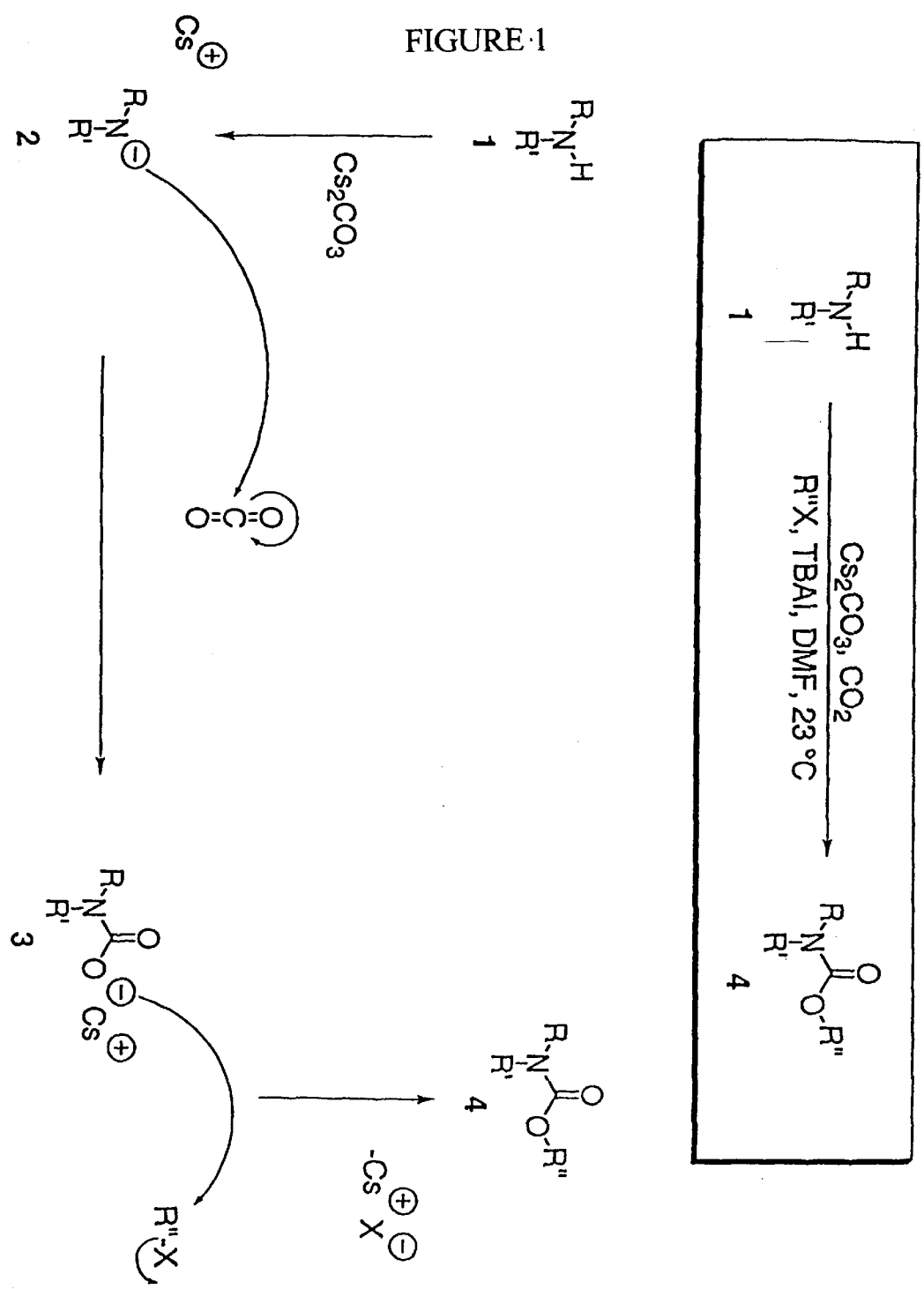
FIG. 1 shows the proposed mechanism for cesium-promoted carbamate synthesis in the presence of an amine RR'NH, an organic electrophile R"X, and CO$_2$.

FIG. 1 shows the proposed mechanism for cesium-promoted carbamate synthesis in the presence of an amine RR'NH, an organic electrophile R"X, and $CO_2$. Not to be limited by theory, the incipient in situ generated amide (2) can be formed by the reaction of an amine (1) with cesium carbonate in anhydrous DMF. The amide is free from the conjugate cesium ion; it is a "naked anion", which renders it more nucleophilic. The amide (2) then rapidly reacts with carbon dioxide, giving rise to carbamate ester (3). The carbamate ester (3) further reacts with the electrophile R"—X, producing carbamate (4) in high yields.

Figure 2:
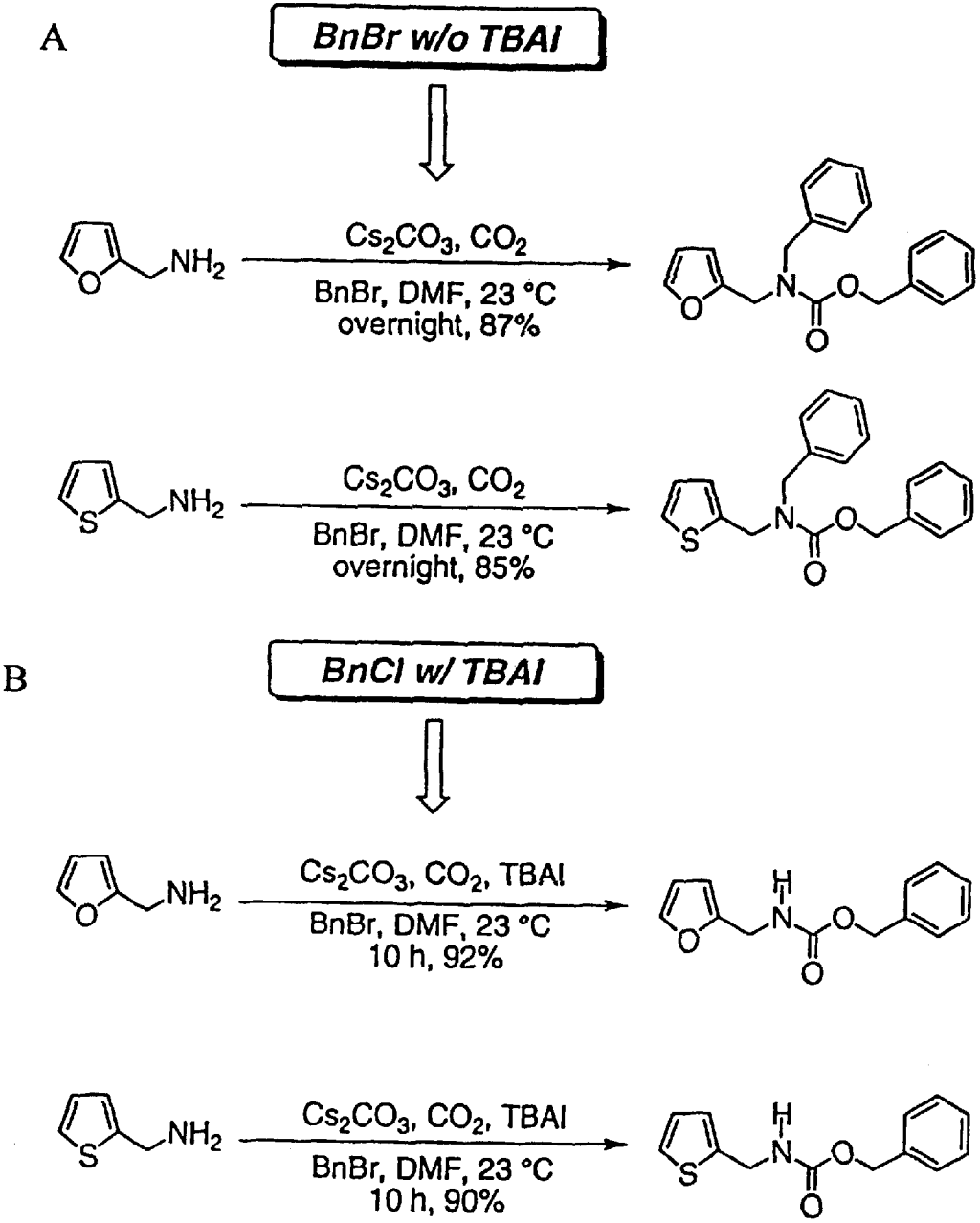
FIG. 2 shows how tributylammonium iodide (TBAI) can be used control the extent of N-alkylation obtained during carbamate synthesis carried out according to the present invention.

FIG. 2 shows how additive TBAI can be used control the extent of N-alkylation obtained during carbamate synthesis carried out according to the present invention. 2-furanmethylamine and 2-thiophenemethylamine are converted to their corresponding carbamates by reaction with benzyl bromide and bubbling carbon dioxide in anhydrous DMF in the presence of cesium carbonate. After reaction at room temperature overnight, 85–87% yields of the respective N-alkylated carbamates are obtained. FIG. 2A. In contrast, when an additive such as TBAI, or other quaternary amine, is included in the reaction, N-alkylation of the product carbamate is suppressed, and the carbamate is obtained in 90–92% yield. FIG. 2B. Thus, the degree of N-alkylation of carbamates obtained using the present invention can be controlled through the addition to the reaction mixture of controlled amounts of additives such as TBAI.

Figure 3:
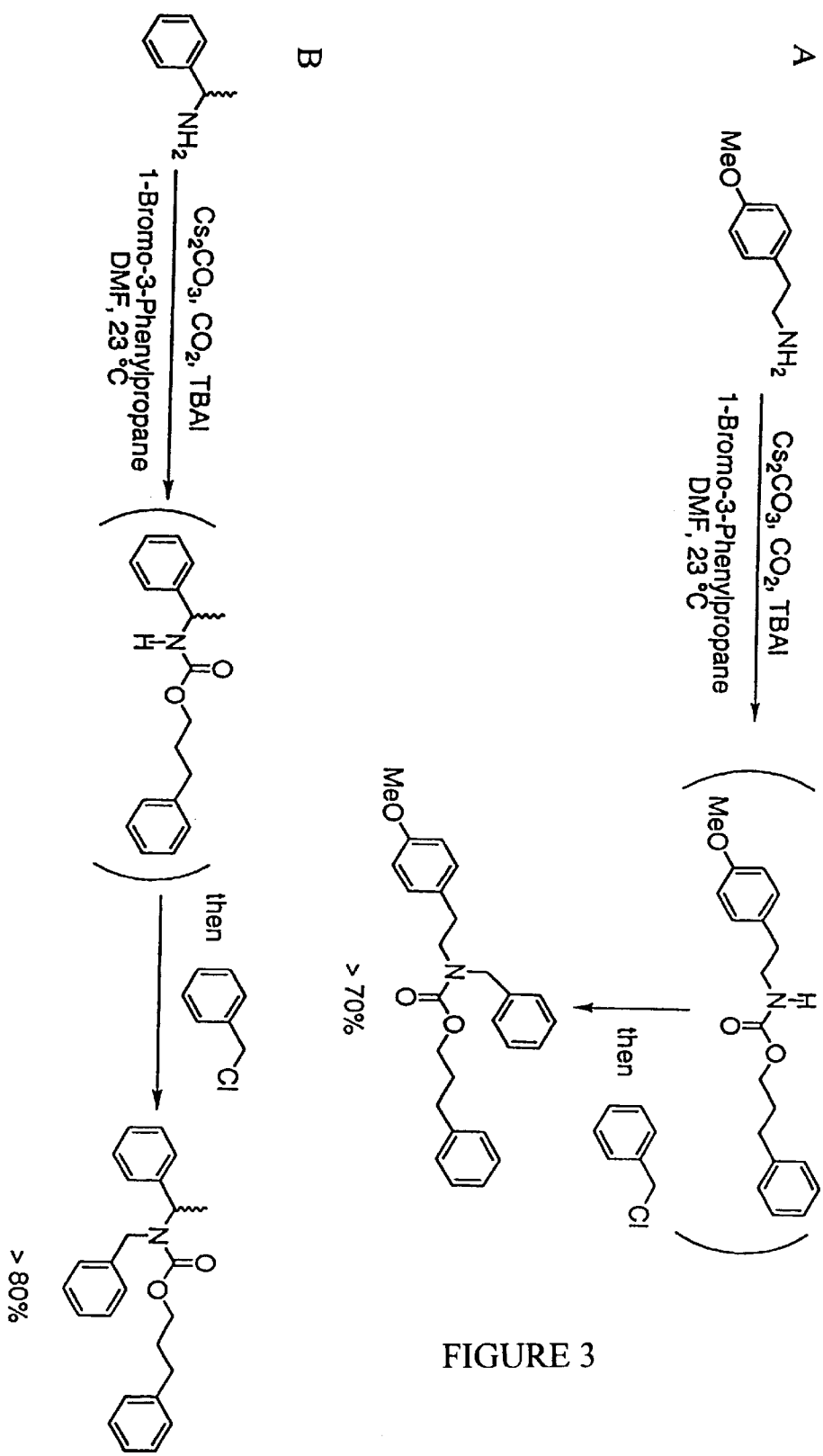
FIG. 3 shows a "one-pot" reaction method whereby different organic electrophiles can be used for carbamate synthesis and subsequent N-alkylation.

FIG. 3 different organic electrophiles can be used for carbamate synthesis and for subsequent N-alkylation of the carbamate. By manipulation of the molar ratios of the organic electrophile relative to amine, and the timing of their addition, surprisingly it is possible to synthesize carbamates comprising different chemical moieties attached at the N- and O-linked positions. Thus, referring now to FIG. 3, there are shown in FIGS. 3A and 3B two examples whereby synthesis of carbamate using a first organic electrophile is accomplished in good yield in the presence of TBAI to suppress N-alkylation, and in a subsequent step an excess of a second, chemically different organic electrophile is added, whereby N-alkylation by the second organic electrophile proceeds smoothly and in good yield. A stoichiometric excess of the second organic electrophile is preferred in this embodiment of the invention to overcome suppression of N-alkylation by TBAI. Therefore, the present invention provides a simple "one-pot" reaction method for the synthesis of N-alkylated carbamates with different moieties at the N- and O-linked positions.

Figure 4:
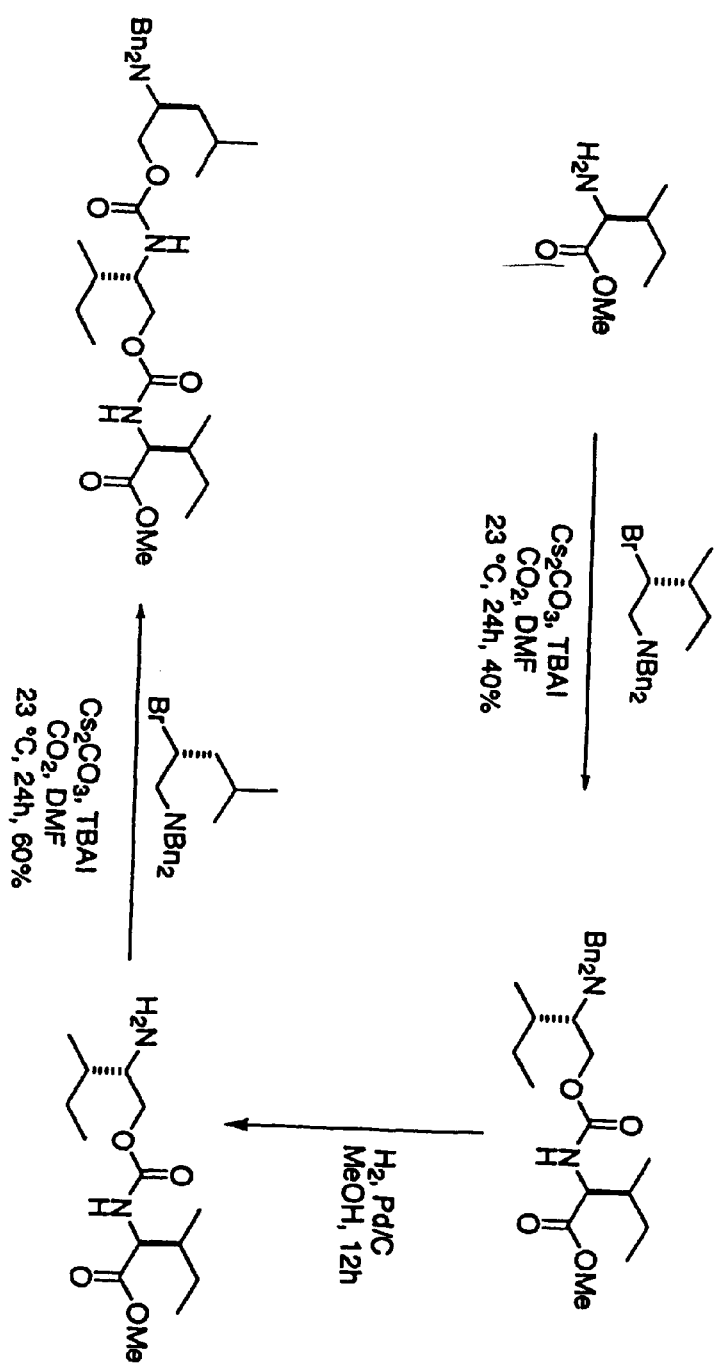
FIG. 4 shows synthesis of peptidomimetic compounds carbamation according to the present invention.

FIG. 4 shows synthesis of peptidomimetic carbamate compounds is efficiently and simply achieved using the present invention. Referring now to FIG. 4, synthesis of an O-methylated Leu-Ile-Leu peptidomimetic compound is shown as an illustrative example. An organic electrophile that also comprises an N-protected amine (here protected by N-butylation) is coupled in a first step via carbamate synthesis to an amine that also comprises a protected carboxylate group (here protected by O-methylation), yielding a peptidomimetic dipeptide analogue with protected N- and C-termini. Deprotection of the N-terminus (here by catalytic hydrogenation) exposes the N-terminal amine for a further cycle of carbamate synthesis through addition of a second organic electrophile that also comprises a protected amine group. Deprotection of the latter protected amine permits the synthetic process to continue. Thus, cycles of alternate carbamate coupling and deprotection steps can be used in the present invention to provide a diverse range of peptidomimetic compounds comprising natural and/or non-natural amino-acid sidechains for use in screening for biological activities, and for other applications.

Figure 5:
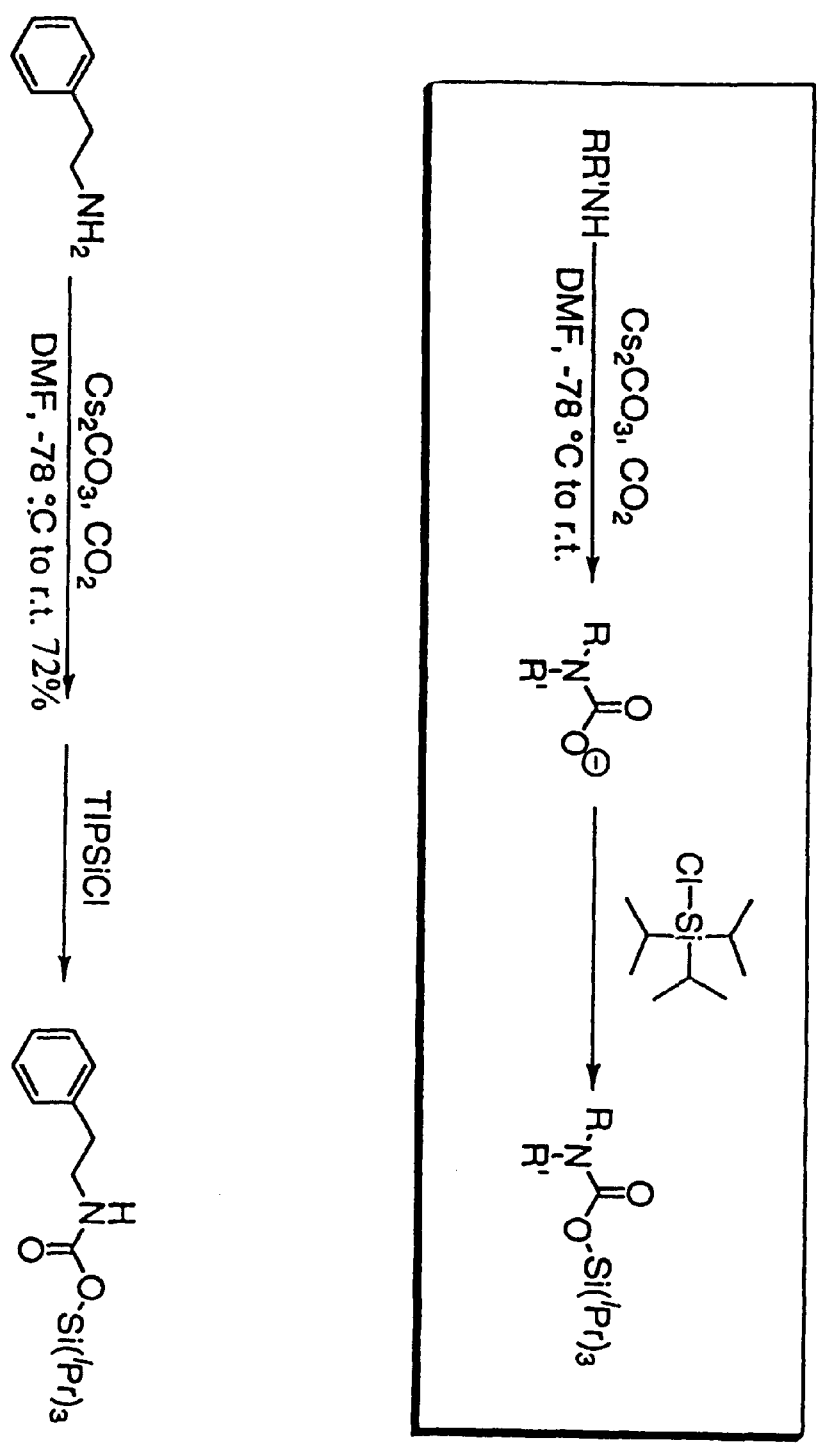
FIG. 5 shows synthesis of silylcarbamates by the present invention.

FIG. 5 shows synthesis of silylcarbamates by the present invention. In this embodiment, low reaction temperatures are preferred (−78° C. to room temperature) and TBAI may optionally be added. The organic electrophile in the present embodiment is triisopropyl silicon chloride (TIPSiCl), resulting in a novel triisopropyl silicon ester that may be cleaved, and is therefore useful in synthetic strategies requiring protection of carboxylic acids.

DETAILED DESCRIPTION OF THE INVENTION

The present invention is directed to providing improved methods for synthesis of carbamates, which substantially obviate the above mentioned problems of the prior art.

The present invention is based upon the inventor's discovery that the synthesis of carbamates of the general formula:

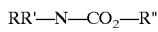

RR'—N—CO$_2$—R"

from the corresponding amine, organic electrophile, and carbon dioxide, is catalyzed by certain cesium bases, wherein R, R', and R" are selected from the group consisting of hydrogen, alkyl of 1–18 carbon atoms, silyl, phenyl, benzyl, cyclopentyl, cyclohexyl, cycloheptyl, cyclooctyl, allyl, and heterocycles.

In the present disclosure, the term amine includes primary, secondary, aromatic, and heterocyclic amines comprising at least one carbon atom and at least one hydrogen covalently bonded to the amine nitrogen. The concentration of the amine is not critical. A concentration of about 0.2 M is advantageous.

The term organic electrophile includes organic halides such as chlorides, bromides, and iodides, as well as other organic electrophiles such as those containing mesyl (O—Ms) or tosyl (O—Ts) groups, silyl halides, or other organic compounds which are activated for electrophilic reaction. In preferred embodiments, chlorides and bromides are used. Most preferably, bromides are used. Organic iodides are less advantageous as electrophiles because they typically react more slowly than corresponding bromides or chlorides, and may be prone to rearrangement. The concentration of organic electrophile is advantageously from a slight molar excess to a several-fold excess, relative to amine concentration.

Advantageously, the cesium salt is cesium carbonate, cesium bicarbonate, cesium bromide, cesium hydroxide, or mixtures thereof In a most preferred embodiment, the cesium salt is cesium carbonate. Cesium carbonate is also preferred when undesirable side reactions, which may be promoted by stronger bases, must be minimized. The production of cesium halides during the reaction helps to drive the reaction to completion where the cesium halide (eg. CsBr) produced by the reaction is insoluble in the solvent used. The preferred amount of cesium salt is about a threefold excess compared to amine.

Optionally, tetrabutyl ammonium iodide (TBAI), or other material promoting halide-exchange, may be included. An advantageous amount of TBAI is from about 0.1 to 2.0 relative to amine concentration.

In the present invention, an anhydrous solvent is provided in which the cesium base is sufficiently soluble to promote carbamate synthesis. The solvent is preferably dimethyl sulfoxide, N,N-dimethylformamide (DMF), 1-methyl-2-pyrrolidinone (NMP), N,N-dimethylacetamide (DMAC), or a mixture thereof. Most preferably the solvent is DMF.

Optionally, a molecular sieve may be added to effectively sequester water produced the reaction. Preferably, a powdered molecular sieve is used that has a pore diameter of about 3–5 Å.

The invention will be readily understood by those of ordinary skill in the art by reference to the following examples and figures.

EXAMPLE 1

Cesium-Promoted Carbamate Synthesis

As a first example, carbamate (2) is prepared in a 40% yield by treatment of phenethylamine (1) in the presence of cesium carbonate, tetrabutylammonium iodide (TBAI), and n-butyl bromide in anhydrous DMF at 93° C. for 21 hours.

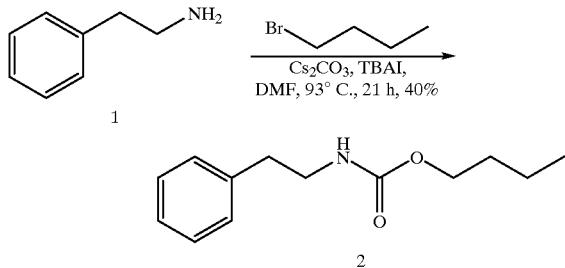

EXAMPLE 2

Efficient Cesium-Promoted Carbamate Synthesis in the Presence of a Carbon Dioxide Source In a preferred embodiment, improved carbamate yield is obtained by supplementing the reaction with a continuous source of carbon dioxide, preferably by bubbling the reaction with a gas containing carbon dioxide. This example is a three-component coupling of amine (3) and n-butyl bromide, at room temperature and in the presence of a continuous source of carbon dioxide, to synthesize benzylcarbamate (4) in high yield. A yield of 96% of benzylcarbamate (4) is obtained in 3 hours at 23° C. from the reaction of n-butyl bromide and benzylamine (3) in anhydrous DMF in the presence of cesium carbonate and tetrabutylammonium iodide (TBAI).

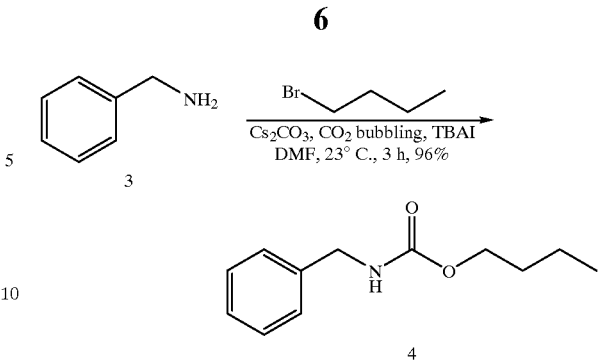

EXAMPLES 3–25

Efficient Synthesis of Carbamates from Alkyl and Primary Amines

A useful feature of the present invention is that carbamates can be prepared by reactions of a very wide range of amines and organic electrophiles under mild conditions, as set forth in the following examples. In these examples, high yields of carbamates of the general formula R—NH—CO$_2$—R' are produced from a range of structurally diverse primary amines reacted with organic electrophiles, preferably organic bromides or chlorides. Reactions are carried out at mild temperatures, preferably 23° C. or 0° C. Examples 3–25 demonstrate the versatility of the present invention and the syntheses are described in detail below.

EXAMPLE 3

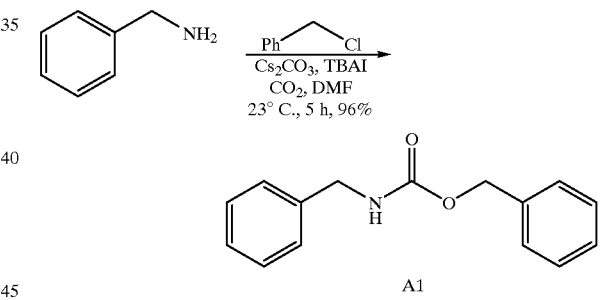

Preparation of carbamate A1: Carbon dioxide is bubbled into a stirred suspension containing benzylamine (0.22 g, 2 mmol), tetrabutylammonium iodide (2.22 g, 6 mmol, 3 eq.) and cesium carbonate (1.95 g, 6 mmol, 3 eq.) in anhydrous N,N-dimethylformamide (10 mL) at room temperature for 1 hour. Benzyl chloride (0.76 g, 6 mmol, 3 eq.) is added in one portion into the reaction and the mixture is stirred at room temperature for 5 hours. The reaction is quenched with water (20 mL) and extracted with ethyl acetate (3×20 mL). The resulting organic layer is then washed consecutively with water (3×20 mL), brine (20 mL), and dried over anhydrous sodium sulfate. Filtration and concentration in vacuo provides the crude carbamate as an oil, which is purified by silica gel column chromatography (9:1 hexanes-EtOAc) to yield the desired carbamate A1 (0.463 g, 96%). Data for A1: IR (thin film) 3331, 3087, 3032, 2957, 2897, 1690, 1534, 1455, 1266, 1140, 748 cm$^{-1}$. $^1$H NMR (360 MHz, CDCl$_3$) δ4.21 (d, 2H, J=5.1 Hz), 4.97 (s, 2H), 6.96–7.18 (m, 11H). $^{13}$C NMR (90 MHz, CDCl$_3$) δ45.12, 66.84, 127.49, 128.11, 128.50, 128.65, 136.45, 138.35, 156.38.

EXAMPLE 4

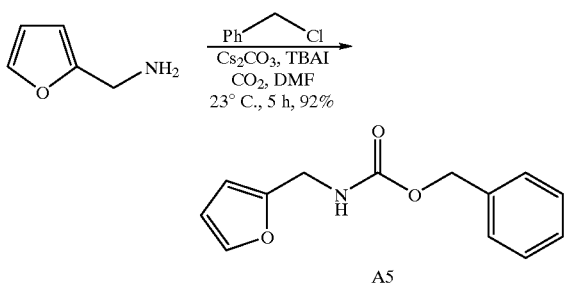

Preparation of carbamate A5: Carbon dioxide is bubbled into a stirred suspension of furfurylamine (0.29 g, 3 mmol), tetrabutylammonium iodide (3.33 g, 9 mmol, 3 eq.) and cesium carbonate (2.93 g, 9 mmol, 3 eq.) in N,N-dimethylformamide (15 mL) at room temperature for 1 hour at 0° C. Benzyl chloride (1.04 mL, 9 mmol, 3 eq.) is added in one portion into the reaction and the mixture is stirred at room temperature for 5 h. The reaction is quenched with water (30 mL) and extracted with ethyl acetate (3×30 mL). The resulting organic layer is then washed consecutively with water (3×30 mL), brine (30 mL), and dried over anhydrous sodium sulfate. Filtration and concentration in vacuo provide the crude carbamate as a oil, which is purified by column chromatography (9:1 hexanes-EtOAc) to the desired carbamate A5 (0.593 g, 92%). Data for A5: IR (thin film) 3326, 3033, 2951, 1716, 1539, 1248, 1132, 1008, 737 cm$^{-1}$. $^1$H NMR (360 MHz, CDCl$_3$) δ4.37 (d, 2H, J=4.37 Hz), 5.12 (s, 2H), 5.13 (bs, NH), 6.23 (s, 1H), 6.30–6.32 (s, 1H), 7.33–7.36 (m, 6H). $^{13}$C NMR (90 MHz, CDCl$_3$) δ38.06, 66.89, 107.22, 110.36, 128.12, 128.49, 136.34, 142.18, 151.50, 156.13.

EXAMPLE 5

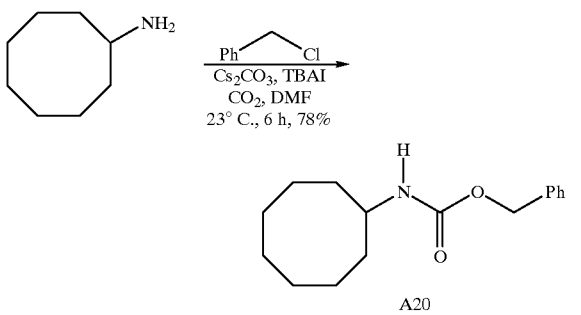

Preparation of carbamate A20. To a solution of cyclooctylamine (0.25 g, 2 mmol) in anhydrous N,N-dimethylformamide (10 mL), cesium carbonate (1.96 g, 6 mmol, 3 eq.) and tetrabutylammonium iodide (2.22 g, 6 mmol, 3 eq.) are added to the solution with vigorous stirring. Carbon dioxide is bubbled into the solution continuously for 1 hour before benzyl chloride (0.76 g, 6 mmol, 3 eq.) is added in one portion. The reaction is allowed to proceed at room temperature with constant carbon dioxide bubbling and stirring for 6 hours, at which point the amine is consumed. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (5:1 hexanes:EtOAc) affords carbamate A20 (0.41 g, 78%) as a pale yellow oil. Data for A20: IR (thin film) 3330, 3087, 3063, 3031, 2920, 2853, 1697, 1528, 1452, 1311, 1233, 1049 cm$^{-1}$. $^1$H NMR (360 MHz, CDCl$_3$) δ1.36–1.78 (m, 20H), 4.66 (s, 2H), 7.08–7.17 (m, 5H). $^{13}$C NMR (90 MHz, CDCl$_3$) δ23.40, 25.27, 27.10, 32.20, 50.98, 66.28, 127.90, 127.98, 128.36, 136.62, 155.33.

EXAMPLE 6

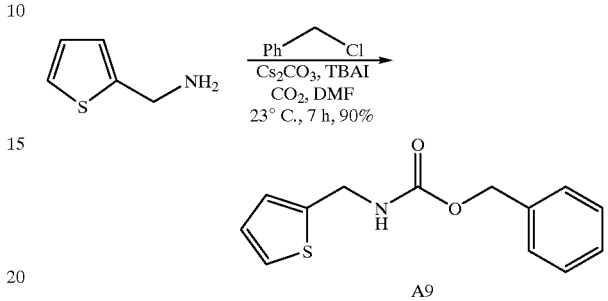

Preparation of carbamate A9: Carbon dioxide is bubbled into a stirred suspension of 2-thiophenemethylamine (0.11 g, 1 mmol), tetrabutylammonium iodide (1.11 g, 3 mmol, 3 eq.) and cesium carbonate (1 g, 3 mmol, 3 eq.) in N,N-dimethylformamide (5 mL) for 1 hour at 0° C. 1-Bromo-3-phenylpropane (0.60 g, 3 mmol, 3 eq.) is added in one portion into the reaction and the mixture is stirred at room temperature for 7 hours. The reaction is quenched with water (10 mL) and extracted with ethyl acetate (3×10 mL). The resulting organic layer is then washed consecutively with water (3×10 mL), brine (10 mL), and dried over anhydrous sodium sulfate. Filtration and concentration in vacuo provide the crude carbamate as an oil, which is purified by column chromatography (9:1 hexanes-EtOAc) to give the desired carbamate A9 (0.256 g, 90%). Data for A9: IR (thin film) 3342, 3034, 2962, 2927, 1684, 1539, 1455, 1254, 1125, 969, 697 cm$^{-1}$. $^1$H NMR (360 MHz, CDCl$_3$) δ4.47–4.49 (d, 2H, J=8.35 Hz), 5.08 (s, 2H), 5.23 (bs, NH), 6.88–7.30 (m, 8H). $^{13}$C NMR (90 MHz, CDCl$_3$) δ39.87, 66.88, 125.11, 125.75, 126.83, 128.11, 128.48, 136.30, 141.14, 156.02.

EXAMPLE 7

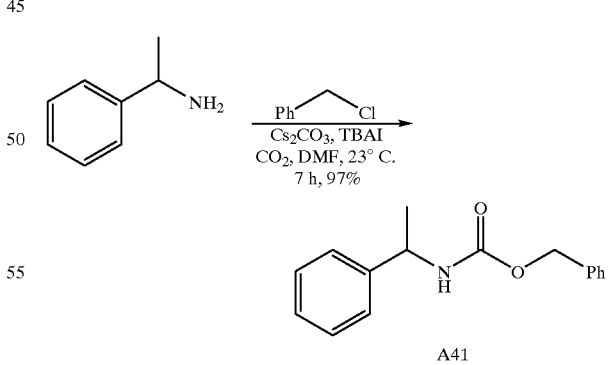

Preparation of carbamate A41. Carbon dioxide is bubbled into a stirred suspension of D, L-α-methylbenzylamine (0.24 g, 2 mmol), tetrabutylammonium iodide (2.22 g, 6 mmol, 3 eq.) and cesium carbonate (1.95 g, 6 mmol, 3 eq.) in N,N-dimethylformamide (10 mL) at room temperature for 1 h. Benzyl chloride (0.92 mL, 6 mmol, 3 eq.) was added in one portion into the reaction and the mixture stirred at room temperature for 7 h. The reaction is quenched with water (20 mL) and extracted with ethyl acetate (3×20 mL). The resulting organic layer is washed consecutively with water (3×20 mL), brine (20 mL), and dried over sodium sulfate. Filtration and concentration in vacuo provide the crude carbamate as an oil, which is purified by column chromatography (9:1 hexanes-EtOAc) to yield carbamate A41 (0.495 g, 97%). Data for A41: IR (thin film) 3324, 3087, 3063, 3031, 2974, 2931, 1697, 1531, 1452, 1329, 1242, 1056, 1028 cm$^{-1}$. $^1$H NMR (360 MHz, CDCl$_3$) δ1.56 (s, 3H), 4.97 (m, 1H), 5.14 (q, 2H, J=12 Hz), 5.68 (m, 1H), 7.35–7.39 (m, 10H). $^{13}$C NMR (90 MHz, CDCl$_3$) δ22.11, 50.37, 66.30, 125.68, 126.90, 127.82, 128.16, 128.27, 143.45, 155.40.

EXAMPLE 8

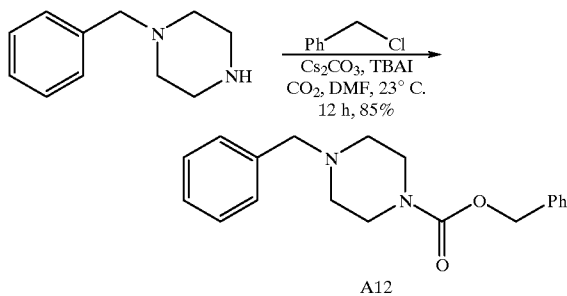

Preparation of carbamate A12. To a solution of 1-benzylpiperazine (0.20 g, 1.1 mmol) in anhydrous N,N-dimethylformamide (6 mL), cesium carbonate (1.1 1 g, 3.4 mmol, 3 eq.) and tetrabutylammonium iodide (1.26 g, 3.4 mmol, 3 eq.) are added to the solution with vigorous stirring. Carbon dioxide is bubbled into the solution continuously for 1 hour before benzyl chloride (0.43 g, 3.4 mmol, 3 eq.) is added. The reaction was allowed to proceed at room temperature with constant carbon dioxide bubbling and stirring for 12 hours at which point the amine is consumed. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (5:1 hexanes:EtOAc) affords carbamate A12 (0.29 g, 85%) as an oil. Data for A12: IR (thin film) 3317, 3061, 3025, 2942, 2857, 1701, 1428, 1296, 1227, 1121, 1013, 933, 747, 699 cm$^{-1}$. $^1$H NMR (360 MHz, CDCl$_3$) δ2.02 (q, 2H, J=7.04 Hz), 2.74 (t, 2H, J=7.62 Hz), 2.86 (bs, 2H), 3.69 (bs, 2H), 4.18 (t, 2H, J=6.48 Hz), 4.61 (d, 2H, J=13 Hz), 7.13–7.32 (m, 10 H). $^{13}$C NMR (90 MHz, CDCl$_3$) δ30.60, 32.32, 45.61, 64.86, 125.92, 126.28, 126.45, 128.78, 141.39, 155.65.

EXAMPLE 9

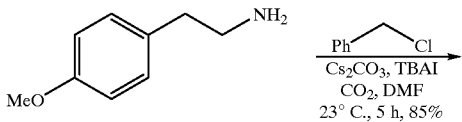

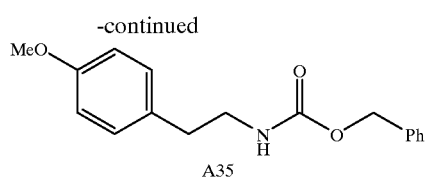

Preparation of carbamate A35. To a cooled solution (0° C.) of p-methoxyphenethylamine (0.20 g, 1.3 mmol) in anhydrous N,N-dimethylformamide (7 mL), cesium carbonate (1.3 g, 4 mmol, 3 eq.) and tetrabutylammonium iodide (1.46 g, 4 mmol, 3 eq.) are added to the solution with vigorous stirring. Carbon dioxide is bubbled into the solution continuously for 1 hour before benzyl chloride (0.54 g, 4 mmol, 3 eq.) is added. The reaction is allowed to proceed at room temperature with constant carbon dioxide bubbling and stirring for 5 hours. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (5:1 hexanes:EtOAc) affords carbamate A35 (0.380 g, 85%) as an oil. Data for A35: IR (thin film) 3330, 3060, 3029, 2962, 2942, 2840, 1682, 1612, 1540, 1464, 1295, 1248, 1184, 1029 cm$^{-1}$. $^1$H NMR (360 MHz, CDCl$_3$) 2.76 (t, 2H, J=6.87 Hz), 3.41–3.43 (m, 2H), 3.78 (s, 3H), 4.9 (bs, N<u>H</u>), 5.10 (s, 2H), 6.85 (2, 2H, J=8.46 Hz), 7.00 (d, 2H, J=8.4 Hz), 7.43 (m, 5H). $^{13}$C NMR (90 MHz, CDCl$_3$) δ35.01, 42.28, 55.10, 66.44, 113.9, 127.96, 128.37, 129.59, 130.58, 136.51, 156.21, 158.12.

EXAMPLE 10

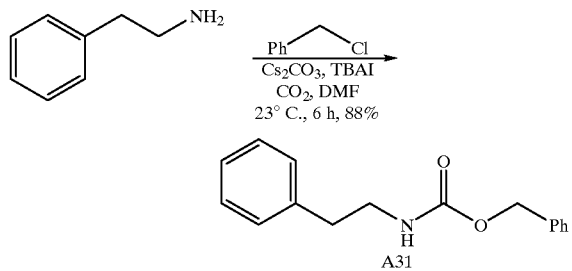

Preparation of carbamate A31. To a solution of phenethylamine (0.20 g, 1.7 mmol) in anhydrous N,N-dimethylformamide (8.5 mL), cesium carbonate (1.6 g, 5 mmol, 3 eq.) and tetrabutylammonium iodide (1.83 g, 5 mmol, 3 eq.) are added to the solution with vigorous stirring. Carbon dioxide is bubbled into the solution continuously for 1 hour before benzyl chloride (0.63 g, 5 mmol, 3 eq.) was added. The reaction is allowed to proceed at room temperature with constant carbon dioxide bubbling and stirring for 6 hours at which point the amine is consumed. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (5:1 hexanes:EtOAc) affords carbamate A31 (0.55 g, 88%) as a pale yellow oil. Data for A31: IR (thin film) 3332, 3058, 2936, 1699, 1520, 1456, 1252, 1136, 1084, 742, 697 cm$^{-1}$ H NMR (360 MHz, CDCl$_3$) δ2.83 (t, 2 H, J=6.81 Hz), 3.48 (q, 2H, J=6.45 Hz), 4.82 (bs, N<u>H</u>), 5.11 (s, 2H), 7.18–7.36 (m, 10H). $^{13}$C NMR (90 MHz, CDCl$_3$) δ36.05, 42.19, 66.61, 126.50, 128.09, 128.50, 128.61, 128.77, 136.56, 138.69, 156.21.

EXAMPLE 11

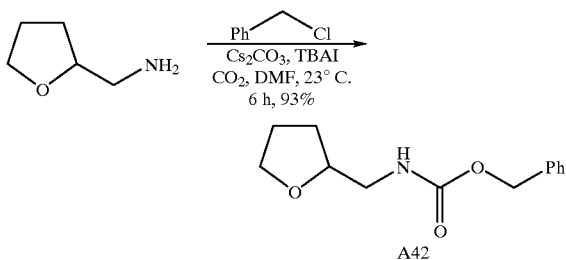

Preparation of carbamate A42. To a solution of tetrahydrofurfurylamine (0.1 g, 1.0 mmol) in anhydrous N,N-dimethylformamide (5 mL), cesium carbonate (1.0 g, 3 mmol, 3 eq.) and tetrabutylammonium iodide (1.11 g, 3 mmol, 3 eq.) are added to the solution with vigorous stirring. Carbon dioxide is bubbled into the solution continuously for 1 hour before benzyl chloride (0.51 g, 3 mmol, 3 eq.) is added. The reaction is allowed to proceed at room temperature with constant carbon dioxide bubbling and stirring for 6 hours at which point the amine is consumed. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (9:1 hexanes:EtOAc) afforded carbamate A42 (0.22 g, 93%) as an oil. Data for A42: IR (thin film) 3345, 3087, 3063, 3030, 2970, 2947, 2871, 1700, 1496, 1465, 1455, 1417, 1364, 1237, 1131, 1100, 1063 cm$^{-1}$. $^1$H NMR (360 MHz, CDCl$_3$) δ1.31–1.35 (m, 1H), 1.67–1.77 (m, 3H), 2.95–3.68 (m, 4H), 4.37–4.95 (m, 2H), 5.02 (s, 2H), 6.79–7.20 (m, 5H). $^{13}$C NMR (90 MHZ, CDCl$_3$) δ25.41, 29.01, 50.95, 67.18, 67.86, 78.04, 118.80, 125.87, 128.40, 137.84, 156.50.

EXAMPLE 12

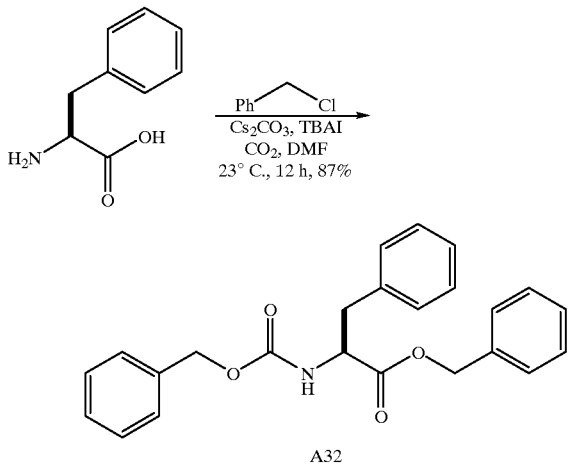

Preparation of carbamate A32. To a solution of L-phenylalanine (0.66 g, 4 mmol) in anhydrous N,N-dimethylformamide (20 mL), cesium carbonate (3.9 g, 12 mmol, 3 eq.) and tetrabutylammonium iodide (4.5 g, 12 mmol, 3 eq.) are added to the solution with vigorous stirring. Carbon dioxide is bubbled into the solution continuously for 1 hour before benzyl chloride (1.4 g, 12 mmol, 3 eq.) is added. The reaction is allowed to proceed at room temperature with constant carbon dioxide bubbling and stirring for 12 hours. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (2:1 hexanes:EtOAc) affords carbamate A32 (1.05 g, 87%) as an oil. Data for A32: IR (thin film) 3338, 3063, 3031, 2953, 1718, 1519, 1345, 1256, 1212, 1055, 742, 697 cm$^{-1}$. $^1$H NMR (360 MHz, CDCl$_3$) δ3.12 (m, 2H), 4.84 (m, 1H), 5.03–5.18 (m, 4H), 5.21 (brs, NH), 7.02–7.34 (m, 15H). 13C NMR (90 MHz, CDCl$_3$) δ38.15, 54.80, 68.96, 67.24, 127.08, 128.08, 128.17, 128.52, 128.56, 129.31, 135.04, 135.51, 136.21, 156.61, 171.36.

EXAMPLE 13

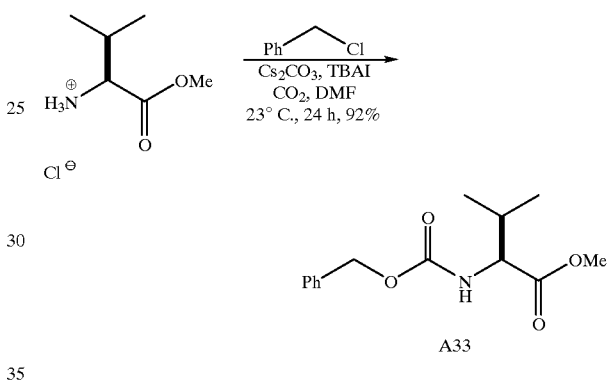

Preparation of carbamate A33. To a solution of L-valine-methyl ester hydrochloride (0.33 g, 2 mmol) in anhydrous N,N-dimethylformamide (10 mL), cesium carbonate (2.0 g, 6 mmol, 3 eq.) and tetrabutylammonium iodide (2.22 g, 6 mmol, 3 eq.) are added to the solution with vigorous stirring. Carbon dioxide is bubbled into the solution continuously for 1 hour before benzyl chloride (0.75 g, 6 mmol, 3 eq.) is added. The reaction is allowed to proceed at room temperature with constant carbon dioxide bubbling and stirring for 24 hours. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (9:1 hexanes:EtOAc) affords carbamate A33 (0.487 g, 92%) as an oil. Data for A33: IR (thin film) 3348, 3063, 2963, 2676, 1714, 1519, 1454, 1372, 1312, 1213, 1162, 1094, 1026, 1016, 739 cm$^{-1}$. $^1$H NMR (360 MHz, CDCl$_3$) δ0.88 (m, 3H), 0.91 (m, 3H), 2.10 (m, 1H), 3.81 (s, 3H), 4.30 (m, 1H), 5.10 (s, 2H), 5.25 (m 1H), 7.15–7.35 (m, 5H). $^{13}$C NMR (90 MHz, CDCl$_3$) δ17.51, 18.91, 31.27, 52.12, 59.00, 67.01, 128.16, 128.52, 136.23, 156.20, 172.84.

EXAMPLE 14

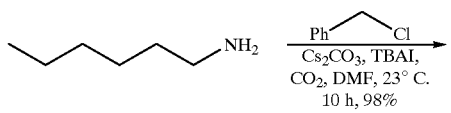

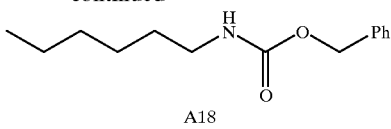

A18

Preparation of carbamate A18. Into a stirred solution of n-hexylamine (0.20 g, 2 mmol) in anhydrous N,N-dimethylformamide (10 mL), cesium carbonate (1.92 g, 6 mmol, 3 eq.) and tetrabutylammonium iodide (2.18 g, 6 mmol, 3 eq.) are added. Carbon dioxide was bubbled through the solution at 0° C. for 1 hour before benzyl chloride (0.76 g, 6 mmol, 3 eq.) is added to the solution. The reaction proceeded at room temperature with constant carbon dioxide bubbling for 10 h after which all the starting material (n-hexylamine) is consumed. The reaction mixture is quenched with water (30 mL) and extracted with ethyl acetate (3×30 mL) thoroughly. The organic layer is then washed with water (2×30 mL), brine (30 mL), and dried over anhydrous sodium sulfate. Evaporation of the solvent and subjection to silica gel column chromatography (5:1 hexanes:EtOAc) affords carbamate A18 (0.45 g, 98%) as an oil. Data for A18: IR (thin film) 3337, 3065, 3033, 2955, 2930, 2858, 1700, 1534, 1455, 1249, 1138 cm$^{-1}$. $^1$H NMR (360 MHz, CDCl$_3$) δ0.79 (t, 3H, J=6.87 Hz), 1.20–1.40 (m, 8H), 3.02–3.12 (m, 2H), 4.78 (bs, N$\underline{H}$), 5.01 (s, 2H), 7.17–7.30 (m, 5H). $^{13}$C NMR (90 MHz, CDCl$_3$) δ13.93, 22.46, 26.30, 29.81, 31.36, 66.43, 127.97, 128.40, 136.59, 156.32.

EXAMPLE 15

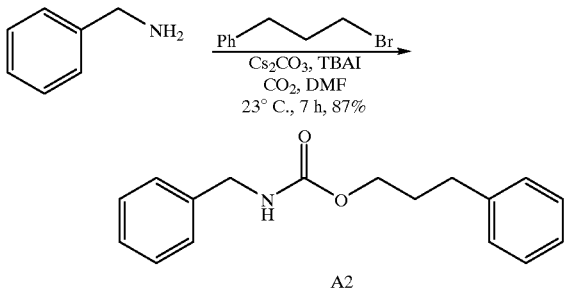

A2

Preparation of carbamate A2: Carbon dioxide is bubbled into a stirred suspension of benzylamine (0.11 g, 1 mmol), tetrabutylammonium iodide (1.11 g, 3 nmmol, 3 eq.) and cesium carbonate (1 g, 3 mmol, 3 eq.) in anhydrous N,N-dimethylformamide (5 mL) at room temperature for 1 hour. 1-Bromo-3-phenyl propane (0.46 mL, 3 mmol, 3 eq.) is added in one portion into the reaction and the mixture is stirred at room temperature for 7 hours. The reaction is quenched with water (10 mL) and extracted with ethyl acetate (3×10 mL). The resulting organic layer is then washed consecutively with water (3×10 mL), brine (20 mL), and dried over anhydrous sodium sulfate. Filtration and concentration in vacuo provides the crude carbamate as an oil, which is purified by column chromatography (9:1 hexanes-EtOAc) to afford the desired carbamate A2 (0.229 g, 87%). Data for A2: IR (thin film) 3330, 3085, 3062, 3027, 2949, 2859, 1699, 1524, 1496, 1453, 1256, 1138 cm$^{-1}$. $^1$H NMR (360 MHz, CDCl$_3$) δ1.96 (m, 2H), 2.70 (t, 2H, J=7.53 Hz), 4.14 (t, 2H, J=6.52 Hz), 4.38 (d, 2H, J=5.76 Hz), 5.04 (bs, N$\underline{H}$), 7.18–7.39 (m, 10H). $^{13}$C NMR (90 MHz, CDCl$_3$) δ30.63, 32.11, 45.01, 64.38, 125.90, 127.43, 128.36, 128.62, 138.54, 141.33, 156.62.

EXAMPLE 16

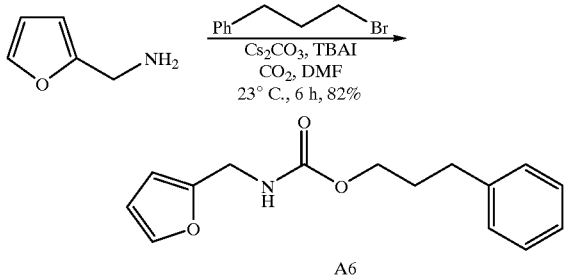

A6

Preparation of carbamate A6: Carbon dioxide is bubbled into a stirred suspension of furfurylamine (0.29 g, 3 mmol), tetrabutylammonium iodide (3.33 g, 9 mmol, 3 eq.) and cesium carbonate (2.93 g, 9 mmol, 3 eq.) in N,N-dimethylformamide (15 mL) at room temperature for 1 hour. 1-Bromo-3-phenylpropane (1.36 g, 9 mmol, 3 eq.) is added in one portion into the reaction and the mixture is stirred at room temperature for 6 hours. The reaction is quenched with water (30 mL) and extracted with ethyl acetate (3×30 mL). The resulting organic layer is then washed consecutively with water (3×30 mL), brine (30 mL), and dried over anhydrous sodium sulfate. The solvent is concentrated and the crude residue is purified by column chromatography (9:1 hexanes-EtOAc) to yield the desired carbamate A6 (0.637 g, 82%). Data for A6: IR (thin film) 3330, 3147, 3318, 3084, 3061, 3026, 2951, 2861, 1705, 1602, 1524, 1453, 1327, 1247 cm$^{-1}$. $^1$H NMR (360 MHz, CDCl$_3$) δ1.96 (m, 2H), 2.68 (t, 2H, J=7.53 Hz), 4.12 (t, 2H, J=6.52 Hz), 4.35 (d, 2H, J=5.36 Hz) 5.06 (bs, N$\underline{H}$), 6.24 (s, 1H), 6.32–6.33 (s, 1H), 7.17–7.36 (m, 6H). $^{13}$C NMR (90 MHz, CDCl$_3$) δ30.36, 31.83, 37.72, 64.19, 106.88, 110.14, 125.69, 128.14, 141.08, 141.83, 151.58, 156.31.

EXAMPLE 17

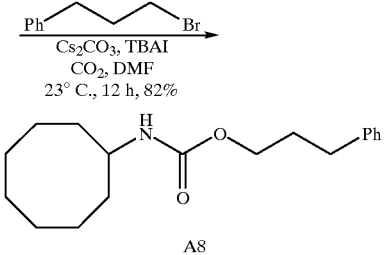

A8

Preparation of carbamate A8. To a solution of cyclooctylamine (0.127 g, 1 mmol) in anhydrous N,N-dimethylformamide (5 mL), cesium carbonate (1 g, 3 mmol, 3 eq.) and tetrabutylammonium iodide (1.11 g, 3 mmol, 3 eq.) are added to the solution with vigorous stirring. Carbon dioxide is bubbled into the solution continuously for 1 hour before 1-bromo-3-phenylpropane (0.46 mL, 3 mmol, 3 eq.) is added. The reaction is allowed to proceed at room temperature with constant carbon dioxide bubbling and stirring for 12 hours at which point the amine is consumed. The reaction mixture is quenched with water and extracted with ethyl acetate (3×30 mL). The extracts are washed with water (2×30 mL), brine (30 mL), and dried over anhydrous sodium sulfate. Evaporation of the solvent and subjection of the crude residue to column chromatography (9:1 hexanes:EtOAc) affords carbamate A8 (0.237 g, 82%) as a pale yellow oil. Data for A8: IR (thin film) 3326, 3061, 3026, 2920, 2855, 1695, 1529, 1497, 1452, 1312, 1246, 1051 cm$^{-1}$. $^1$H NMR (360 MHz, CDCl$_3$) δ1.26–1.67 (m, 14H), 1.71–1.78 (m, 2H), 2.47 (t, 2H, J=7.53 Hz), 2.28 (m, 1H), 3.89 (t, 2H, J=6.52 Hz), 7.00–7.13 (m, 6H). $^{13}$C NMR (90 MHz, CDCl$_3$) δ23.42, 25.26, 27.09, 30.62, 32.08, 32.20, 50.80, 63.80, 125.77, 128.25, 141.33, 155.60.

EXAMPLE 18

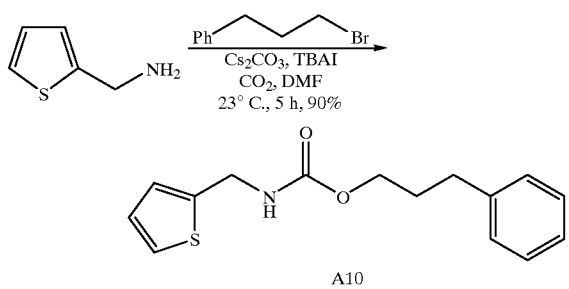

A10

Preparation of carbamate A10: Carbon dioxide is bubbled into a stirred suspension of 2-thiophenemethylamine (0.11 g, 1 mmol), tetrabutylammonium iodide (1.11 g, 3 mmol, 3 eq.) and cesium carbonate (1 g, 3 mmol, 3 eq.) in N,N-dimethylformamide (5 mL) at room temperature for 1 hour. 1-Bromo-3-phenylpropane (0.60 g, 3 mmol, 3 eq.) is added in one portion into the reaction and the mixture is stirred at ambient temperature for 5 hours. The reaction is then quenched with water (10 mL) and extracted with ethyl acetate (3×10 mL). The resulting organic layer is then washed consecutively with water (3×10 mL), brine (10 mL), and dried over anhydrous sodium sulfate. Removal of the solvent provides the crude carbonate as an oil, which was purified by column chromatography (9:1 hexanes-EtOAc) to yield the desired carbamate A10 (0.256 g, 90%). Data for A10: IR (thin film) 3328, 3105, 3083, 3061, 3025, 2948, 2860, 1700, 1517, 1453, 1327, 1246, 1130cm$^{-1}$. $^1$H NMR (360 MHz, CDCl$_3$) δ2.01 (m, 2H), 2.73 (t, 2H, J=7.53 Hz), 4.17 (t, 2H, J=6.52 Hz), 4.55 (s, 2H), 5.52 (bs, NH), 6.97–7.36 (m, 8H). $^{13}$C NMR (90 MHz, CDCl$_3$) δ30.35, 31.80, 39.48, 64.12, 124.69, 125.36, 125.67, 126.23, 128.12, 141.04, 141.39, 156.19.

EXAMPLE 19

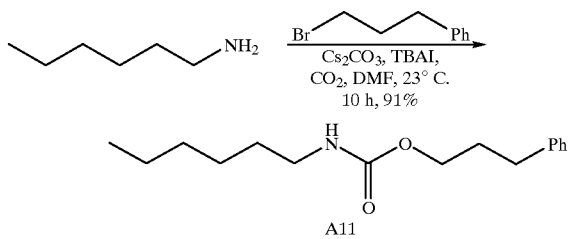

A11

Preparation of carbamate A11. Into a stirred solution of n-hexylamine (0.20 g, 2 mmol) in anhydrous N,N-dimethylformamide (10 mL), cesium carbonate (1.92 g, 6 mmol, 3 eq.) and tetrabutylammonium iodide (2.18 g, 6 mmol, 3 eq.) are added. Carbon dioxide is bubbled through the solution for 1 hour at 0° C. before 1-bromo-3-phenylpropane (1.17 g, 6 mmol, 3 eq.) is added to the solution. The reaction is allowed to proceed at room temperature with constant carbon dioxide bubbling for 10 h after which all the starting material (n-hexylamine) is consumed. The reaction mixture is quenched with water (~30 mL) and extracted with ethyl acetate (3×30 mL) thoroughly. The organic layer is then washed with water (2×30 mL), brine (30 mL), and dried over anhydrous sodium sulfate. Evaporation of the solvent and subjection to silica gel column chromatography (5:1 hexanes:EtOAc) affords carbamate A11 (0.39 g, 91%) as an oil. Data for A11: IR (thin film) 3336, 3062, 3026, 2954, 2929, 2857, 1697, 1535, 1454, 1249, 1142, 1030 cm$^{-1}$. $^1$H NMR (360 MHz, CDCl$_3$) δ0.72 (t, 3H, J=6.87 Hz), 1.12–1.30 (m, 8H), 1.74 (s, 2H), 2.39 (m, 2H), 2.86 (m, 2H), 3.90 (m, 2H), 5.11 (bs, NH), 6.99–7.08 (m, 5H). $^{13}$C NMR (90 MHz, CDCl$_3$) δ13.62, 22.18, 26.04, 29.54, 30.36, 31.11, 31.71, 40.05, 63.46, 125.47, 127.94, 140.96, 156.42.

EXAMPLE 20

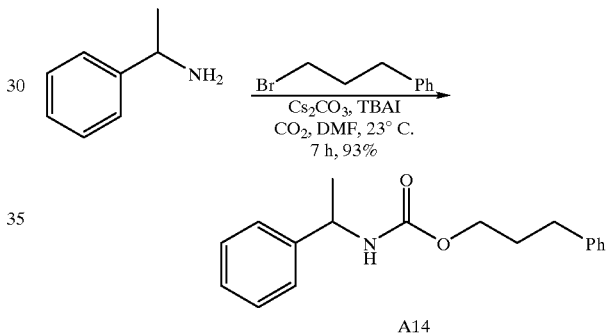

A14

Preparation of carbamate A14: Carbon dioxide is bubbled into a stirred suspension of D,L-α-methylbenzylamine (0.121 g, 1 mmol), tetrabutylammonium iodide (1.11 g, 3 mmol, 3 eq.) and cesium carbonate (1 g, 3 mmol, 3 eq.) in N,N-dimethylformamide (5 mL) at room temperature for 1 h. 1-Bromo-3-phenylpropane (0.60 g, 3 mmol, 3 eq.) is added in one portion into the reaction and the mixture is stirred at room temperature for 7 h. The reaction is quenched with water (10 mL) and extracted with ethyl acetate (3×10 mL). The resulting organic layer is then washed consecutively with water (3×10 mL), brine (10 mL), and dried over sodium sulfate. Filtration and concentration in vacuo provide the crude carbamate as an oil, which is purified by column chromatography (9:1 hexanes-EtOAc) to yield the desired carbamate A14 (0.263 g, 93%). Data for A14: IR (thin film) 3324, 3061, 3027, 2972, 1698, 1532, 1453, 1328, 1245, 1061, 748, 699 cm$^{-1}$. $^1$H NMR (360 MHz, CDCl$_3$) δ1.50 (d, 3H, J=6.66 Hz), 1.93 (m, 2H), 2.68 (m, 2H), 4.06–4.11 (m, 2H), 4.82 (m, 1H), 4.98 (m, 1H), 7.17–7.38 (m, 10H). $^{13}$C NMR (90 MHz, CDCl$_3$) δ22.41, 30.61, 32.10, 50.51, 64.23, 125.87, 127.24, 128.34, 128.59, 141.35, 143.58, 155.77.

EXAMPLE 21

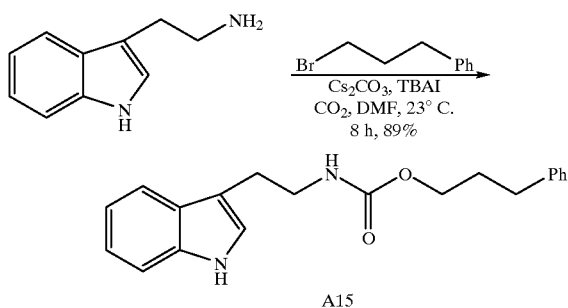

A15

Preparation of carbamate A15: Carbon dioxide is bubbled into a stirred suspension of tryptamine (0.160 g, 1 mmol), tetrabutylammonium iodide (1.11 g, 3 mmol, 3 eq.) and cesium carbonate (1 g, 3 mmol, 3 eq.) in N,N-dimethylformamide (5 mL) at room temperature for 1 h. 1-Bromo-3-phenylpropane (0.60 g, 3 mmol, 3 eq.) is added in one portion into the reaction and the mixture is stirred at room temperature for 8 h. The reaction is quenched with water (10 mL) and extracted with ethyl acetate (3×10 mL). The resulting organic layer is then washed consecutively with water (3×10 mL), brine (10 mL), and dried over sodium sulfate. Filtration and concentration in vacuo provide the crude carbamate as an oil, which is purified by column chromatography (9:1 hexanes-EtOAc) to yield carbamate A15 (0.287 g, 89%). Data for A15: IR (thin film) 3413, 3330, 3058, 3025, 2942, 2855, 1697, 1520, 1455, 1338, 1257, 1082 cm$^{-1}$. $^1$H NMR (360 MHz, CDCl$_3$) δ2.40 (m, 2H), 2.84 (m, 2H), 3.14 (m, 2H), 3.60 (m, 2H), 4.24 (m, 2H), 4.94 (brs, NH), 7.01–8.60 (m, 9H). $^{13}$C NMR (90 MHz, CDCl$_3$) δ25.85, 30.72, 32.20, 41.39, 64.31, 111.42, 112.67, 118.75, 119.41, 122.12, 122.30, 126.03, 127.37, 128.50, 136.51, 141.47, 156.93.

EXAMPLE 22

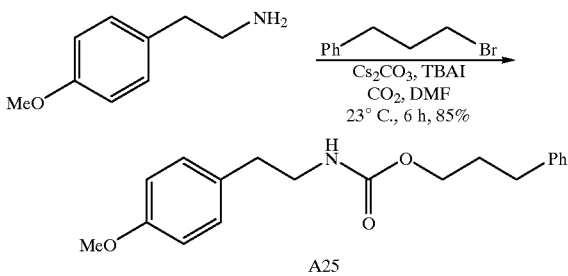

A25

Preparation of carbamate A25. To a stirred solution of p-methoxy-phenethylamine (0.2 g, 1 mmol) in anhydrous N,N-dimethylformamide (7 mL,), cesium carbonate (1.30 g, 3 mmol, 3 eq.) and tetrabutylammonium iodide (1.5 g, 3 mmol, 3 eq.) are added to the solution with vigorous stirring. Carbon dioxide is bubbled into the solution continuously for 1 hour before 1-bromo-3-phenylpropane (0.79 g, 3 mmol, 3 eq.) is added. The reaction is allowed to proceed at ambient temperature with constant carbon dioxide bubbling and stirring for 6 hours at which point the amine is consumed. The reaction mixture is quenched with water and extracted with ethyl acetate (3×30 mL). The combined organic layers are rinsed with water (2×30 mL), brine (30 mL) and dried over anhydrous sodium sulfate. Evaporation of the solvent and subjection of the crude residue to column chromatography (5:1 hexanes:EtOAc) affords carbamate A25 (0.350 g, 85%) as a pale yellow oil. Data for A25: IR (thin film) 3323, 3062, 3029, 2959, 2941, 2866, 2836, 1680, 1611, 1537, 1512, 1468, 1298, 1246, 1032 cm$^{-1}$. $^1$H NMR (360 MHz, CDCl$_3$) δ1.93–1.95 (m, 2H), 2.66 (t, 2H, J=7.38 Hz), 2.77 (t, 2H, J =6.66 Hz), 3.42 (m, 2H), 3.79 (s, 3H), 4.1 (m, 2H), 4.69 (bs, NH), 6.83–7.38 (m, 9H). $^{13}$C NMR (90 MHz, CDCl$_3$) δ30.66, 32.14, 35.20, 42.29, 55.24, 64.17, 114.02, 125.92, 128.39, 129.71, 130.79, 141.40, 156.58, 158.25.

EXAMPLE 23

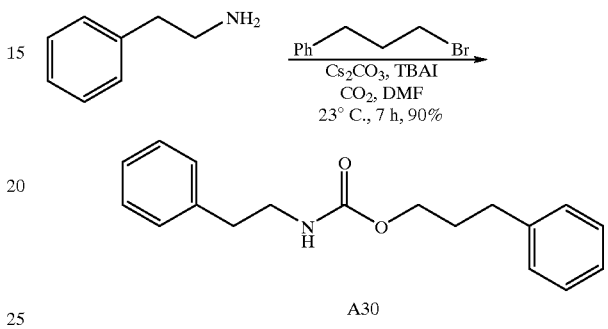

A30

Preparation of carbamate A30. To a solution of phenethylamine (0.20 g, 1.7 mmol) in anhydrous N,N-dimethylformamide (9 mL), cesium carbonate (1.6 g, 5 mmol, 3 eq.) and tetrabutylammonium iodide (1.83 g, 5 mmol, 3 eq.) are added to the solution with vigorous stirring. Carbon dioxide is bubbled into the solution continuously for 1 hour before 1-bromo-3-phenylpropane (0.98 g, 5 mmol, 3 eq.) is added. The reaction is allowed to proceed at room temperature with constant carbon dioxide bubbling and stirring for 7 hours at which point the amine is consumed. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (5:1 hexanes:EtOAc) afforded carbamate A30 (0.43 g, 90%) as a pale yellow oil. Data for A30: IR (thin film) 3335, 3061, 3026, 2943, 2862, 1716, 1539, 1454, 1250, 1139, 1030, 910, 844, 743, 699 cm$^{-1}$. $^1$H NMR (360 MHz, CDCl$_3$) δ1.96 (m, 2H), 2.70 (t, 2H, J=7.53 Hz), 4.14 (t, 2H J=6.52 Hz), 4.38 (d, 2H, J=5.76 Hz), 5.04 (bs, NH), 7.18–7.39 (m, 10H). $^{13}$C NMR (90 MHz, CDCl$_3$) δ30.63, 32.11, 36.13, 42.08, 64.17, 125.90, 127.43, 128.36, 128.62, 138.54, 141.33, 156.62.

EXAMPLE 24

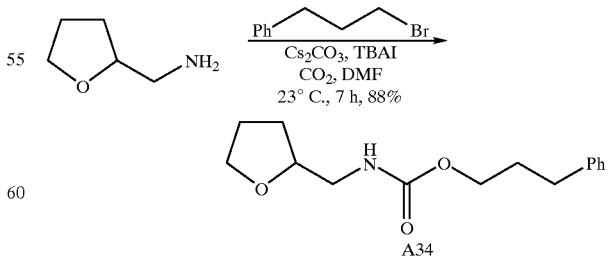

A34

Preparation of carbamate A34. To a solution of tetrahydrofurylamine (0.20 g, 1.7 mmol) in anhydrous N,N-dimethylformamide (9 mL), cesium carbonate (1.0 g, 5 mmol, 3 eq.) and tetrabutylammonium iodide (1.1 g, 5 mmol, 3 eq.) are added to the solution with vigorous stirring. Carbon dioxide is bubbled into the solution continuously for 1 hour before 1-bromo-3-phenylpropane (0.63 g, 5 mmol, 3 eq.) is added. The reaction is allowed to proceed at room temperature with constant carbon dioxide bubbling and stirring for 7 hours at which point the amine is consumed. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (5:1 hexanes:EtOAc) affords carbamate A34 (0.39 g, 88%) as a pale yellow oil. Data for A34: IR (thin film) 3330, 2949, 2870, 1719, 1538, 1454, 1248, 1149, 1082, 1024, 747, 700 cm$^{-1}$. $^1$H NMR (360 MHz, CDCl$_3$) δ1.34–1.39 (m, 2H), 1.68–1.80 (m, 4H), 2.49 (t, 2H, J=7.31Hz), 2.90–2.98 (m, 1H), 3.22–3.27 (m, 1H), 3.55–3.91 (m, 5H), 5.04 (bs, NH), 6.98–7.11 (m, 5H). $^{13}$C NMR (90 MHz, CDCl$_3$) δ25.82, 28.40, 30.66, 32.12, 44.75, 64.20, 68.07, 76.79, 125.089, 128.37, 141.39, 156.86.

EXAMPLE 25

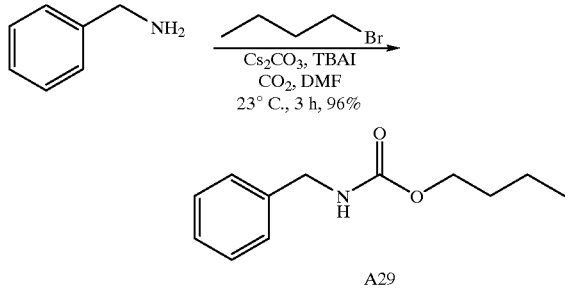

Preparation of carbamate A29. To a solution of benzylamine (0.20 g, 1.9 mmol) in anhydrous N,N-dimethylformamide (10 mL), cesium carbonate (1.82 g, 6 mmol, 3 eq.) and tetrabutylammonium iodide (2.06 g, 6 mmnol, 3 eq.) are added. Carbon dioxide (flow rate ≅25–30 mL/min) is bubbled through the solution for 1 hour before 1-bromobutane (0.77 g, 6 mmol, 3 eq.) is added to the solution. The reaction proceeds at room temperature with constant carbon dioxide bubbling for 3 hours after which all the starting material (benzylamine) is consumed. The reaction mixture is poured into water (~30 mL) and extracted with ethyl acetate (3×30 mL) thoroughly. The organic layer is washed with water (2×30 mL), brine (30 mL), and dried over anhydrous sodium sulfate. Evaporation of the solvent and subjection to silica gel column chromatography (5:1 hexanes:EtOAc) affords carbamate A29 (480 mg, 96%) as an oil. Data for A29: IR (thin film) 3330, 3085, 3062, 3027, 2949, 2859, 1699, 1524, 1496, 1453, 1256, 1138 cm$^{-1}$ $^1$H NMR (360 MHz, CDCl$_3$) δ0.85 (t, 3H, J=7.23 Hz) 1.32 (m, 2H), 1.52 (m, 2H), 4.02 (t, 2H, J=6.26 Hz), 4.28 (d, 2H, J=4.71 Hz), 4.93 (bs, NH), 7.17–7.27 (m, 5H). $^{13}$C NMR (90 MHz, CDCl$_3$) δ13.72, 19.03, 31.04, 44.99, 64.88, 127.40, 127.47, 128.61, 138.59, 156.77.

EXAMPLES 26–43

Efficient Synthesis of Carbamates from Aromatic Primary and Secondary Amines

In further embodiments of the present invention, the inventor has surprisingly discovered that carbamates are synthesized in good to excellent yields from relatively unreactive aromatic amines under mild conditions in DMF in the presence of TBAI, Cs$_2$CO$_3$, and CO$_2$. Aromatic amines are generally less reactive than corresponding alkyl amines, therefore this example significantly extends the utility of the present invention. The following examples are illustrative of the synthesis of carbamates from aromatic amines.

EXAMPLE 26

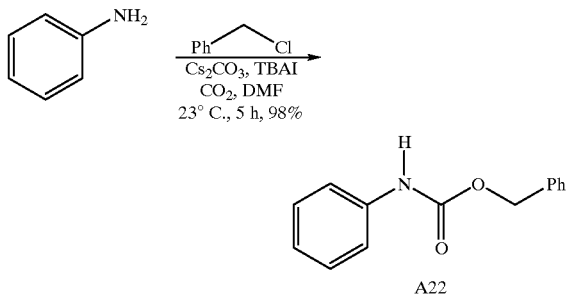

Preparation of carbamate A22. To a solution of aniline (0.186 g, 2 mmol) in anhydrous N,N-dimethylformamide (10 mL), cesium carbonate (1.96 g, 6 mmol, 3 eq.) and tetrabutylammonium iodide (2.22 g, 6 mmol, 3 eq.) are added. Carbon dioxide is bubbled through the solution for 1 hour before benzyl chloride (0.76 g, 6 mmol, 3 eq.) is added to the solution in one portion via syringe. The reaction proceeds at room temperature with constant carbon dioxide bubbling for 5 h after which point all of aniline is consumed. The reaction mixture is poured into water (30 mL) and extracted with ethyl acetate (3×30 mL) thoroughly. The organic layer is washed with water (2×30 mL), brine (30 mL), and then dried over anhydrous sodium sulfate. Evaporation of the solvent and subjection to silica gel column chromatography (5:1 hexanes:EtOAc) affords carbamate A22 (0.44 g, 98%) as an oil. Data for A22: IR (thin film) 3317, 3061, 3035, 2988, 2945, 2892, 1693, 1597, 1532, 1444, 1313, 1227 cm$^{-1}$. $^1$H NMR (360 MHz, CDCl$_3$) 5.04 (s, 2H), 6.75–7.34 (m, 10H). $^{13}$C NMR (90 MHz, CDCl$_3$) 66.88, 118.63, 123.39, 126.89, 127.51, 128.51, 128.94, 135.95, 137.71, 153.37.

EXAMPLE 27

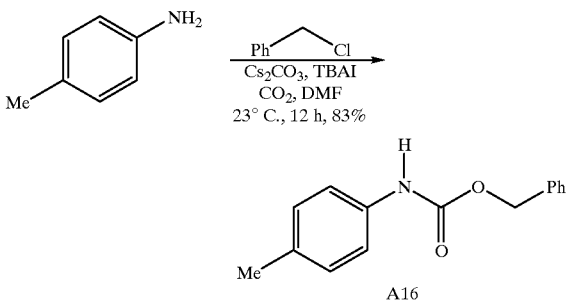

Preparation of carbamate A16. p-toluidine (0.21 g, 2 mmol) is dissolved in anhydrous N,N-dimethylformamide (10 mL) to make a 0.2 M solution. Cesium carbonate (1.96 g, 6 mmol, 3 eq.) and tetrabutylammonium iodide (2.22 g, 6 mmol, 3 eq.) are added to the solution with vigorous stirring. After, carbon dioxide is allowed to pass through the suspension for 1 hour, and benzyl chloride (0.76 g, 6 mmol, 3 eq.) is added to the reaction mixture with constant stirring. The reaction proceeds at ambient temperature with carbon dioxide bubbling through for a time period of 12 hours after which the p-Toluidine is consumed. The reaction is quenched with water (30 mL), extracted with ethyl acetate (3×30 mL), brine (30 mL) and dried over anhydrous sodium sulfate. Removal of solvent in vacuo and subjected to column chromatography (5:1 hexanes:EtOAc) affords carbamate A16 (0.40 g, 83%) as an oil. Data for A16: IR (thin film) 3318, 3063, 3032, 2948, 2921, 1700, 1597, 1537, 1408, 1315, 1224, 1062 cm$^{-1}$ $^{1}$H NMR (360 MHz, CDCl$_3$) δ2.71 (s, 3H), 5.04 (s, 2H), 6.87–7.24 (m, 10H). $^{13}$C NMR (90 MHz, CDCl$_3$) δ20.82, 66.74, 118.77, 126.79, 127.16, 128.44, 130.40, 132.87, 135.14, 136.06, 153.49.

EXAMPLE 28

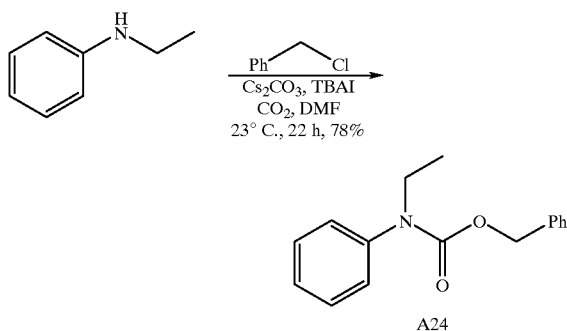

A24

Preparation of carbamate A24. To a solution of N-ethylaniline (0.24 g, 2 mmol) in anhydrous N,N-dimethylformamide (10 mL), cesium carbonate (1.96 g, 6 mmol, 3 eq.) and tetrabutylammonium iodide (2.22 g, 6 mmol, 3 eq.) are added. Carbon dioxide (flow rate≈25–30 mL/min) is bubbled through the solution for 1 hour before benzyl chloride (0.75 g, 6 mmol, 3 eq.) is added to the solution. The reaction proceeds at room temperature with constant carbon dioxide bubbling for 22 h at ambient temperature. The reaction mixture is poured into water (30 mL) and extracted with ethyl acetate (3×30 mL) thoroughly. The organic layer is then washed with water (2×30 mL), brine (30 mL), and dried over anhydrous sodium sulfate. Evaporation of the solvent and subjection to silica gel column chromatography (9:1 hexanes:EtOAc) affords carbamate A24 (0.20 g, 78%) as an oil. Data for A24: IR (thin film) 3085, 3060, 3024, 2966, 2925, 2866, 1732, 1598, 1505, 1452, 1370, 1268 cm$^{-1}$. $^{1}$H NMR (360 MHz, CDCl$_3$) δ1.17–1.22 (t, 3 H, J=7.04 Hz), 3.75–3.80 (q, 2H, J=7.2 Hz), 5.19 (s, 2H), 7.24–7.41 (m, 10 H). $^{13}$C NMR (90 MHz, CDCl$_3$) δ13.58, 45.27, 66.85, 126.52, 127.38, 127.65, 128.25, 128.44, 128.82, 136.65, 141.53, 155.06.

EXAMPLE 29

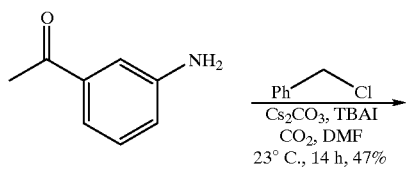

-continued

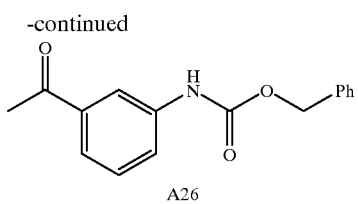

A26

Preparation of carbamate A26. To a solution of 3-aminoacetophenone (0.2 g, 1.5 mmol) in anhydrous N,N-dimethylformamide (8 mL), cesium carbonate (1.4 g, 4.3 mmol, 3 eq.) and tetrabutylammonium iodide (1.63 g, 4.3 mmol, 3 eq.) are added to the solution with vigorous stirring. Carbon dioxide is bubbled into the solution continuously for 1 hour before benzyl chloride (0.37 g, 4.3 mmol, 3 eq.) is added. The reaction is allowed to proceed at room temperature with constant carbon dioxide bubbling and vigorous stirring for 14 hours. The reaction mixture is quenched with water and extracted with ethyl acetate (3×30 mL). The combined organic layers are then washed with water (2×30 mL), brine (30 mL) and dried over anhydrous sodium sulfate. Evaporation of the solvent and subjection of the crude residue to column chromatography (1:1 hexanes:EtOAc) affords carbamate A26 (0.187 g, 47%) as a pale oil. Data for A26: IR (thin film) 3345, 3084, 3061, 3028, 2917, 2866, 1734, 1682, 1596, 1494, 1450, 1356, 1264 cm$^{-1}$. $^{1}$H NMR (360 MHz, CDCl$_3$) δ2.52 (s, 3H), 4.73 (s, 2H), 6.94–7.43 (m, 10 H). $^{-}$CNMR(90MHz, CDCl$_3$) δ26.53, 54.19, 111.42, 117.01, 126.54, 127.00, 127.44, 128.19, 128.29, 128.65, 129.29, 138.42, 149.07, 198.20.

EXAMPLE 30

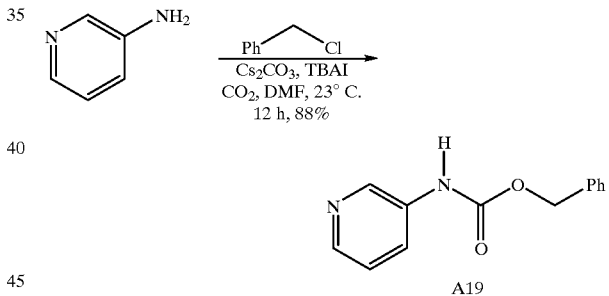

A19

Preparation of carbamate A19. To a solution of 3-aminopyridine (0.20 g, 2 mmol) in anhydrous N,N-dimethylformamide (11 mL), cesium carbonate (1.96 g, 6 mmol, 3 eq.) and tetrabutylammonium iodide (2.22 g, 6 mmol, 3 eq.) are added to the solution with vigorous stirring. Carbon dioxide is bubbled into the solution continuously for 1 hour before benzyl chloride (0.76 g, 6 mmol, 3 eq.) is added. The reaction is allowed to proceed at room temperature with constant carbon dioxide bubbling and stirring for 12 hours at which point the amine is consumed. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (1:1 hexanes:EtOAc) affords carbamate A19 (0.40 g, 88%) as a pale yellow oil. Data for A19: IR (thin film) 3244, 3186, 3111, 3029, 2960, 2877, 2821, 2778, 1720, 1617, 1590, 1559, 1429, 1291, 1227, 1039 cm$^{-1}$. $^{1}$ H NMR (360 MHz, CDCl$_3$) δ5.04 (s, 2H), 6.99–8.29 (m, 10H). $^{13}$C NMR (90

MHz, CDCl₃) δ67.38, 123.73, 125.78, 128.39, 128.53, 128.67, 140.23, 144.51, 153.33.

EXAMPLE 31

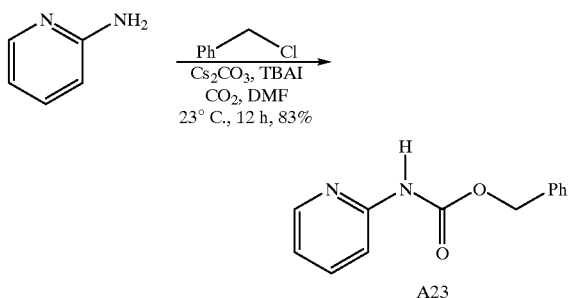

A23

Preparation of carbamate A23. To a solution of 2-aminopyridine (0.2 g, 2 mmol) in anhydrous N,N-dimethylformamide (11 mL), cesium carbonate (1.96 g, 6 mmol, 3 eq.) and tetrabutylammonium iodide (2.22 g, 6 mmol, 3 eq.) are added to the solution with vigorous stirring. Carbon dioxide is bubbled into the solution continuously for 1 hour before benzyl chloride (0.76 g, 6 mmol, 3 eq.) was added. The reaction is allowed to proceed at ambient temperature with constant carbon dioxide bubbling and stirring for 12 hours at which point the amine is consumed. The reaction mixture is quenched with water and extracted with ethyl acetate (3×30 mL). The combined organic layers are rinsed with water (2×30 mL), brine (30 mL) and dried over anhydrous sodium sulfate. Evaporation of the solvent and subjection of the crude residue to column chromatography (1:1 hexanes:EtOAc) affords carbamate A23 (0.35 g, 83%) as a pale yellow oil. Data for A23: IR (thin film) 3181, 3118, 3037, 2953, 2925, 2895, 2852, 1733, 1592, 1546, 1438, 1307, 1221, 1064 cm⁻¹. ¹H NMR (360 MHz, CDCl₃) δ5.07 (s, 2H), 6.61–7.99 (m, 9H), 10.19 (s, NH). ¹³C NMR (90 MHz, CDCl₃) δ67.04, 112.47, 118.32, 128.39, 128.56, 129.35, 135.88, 138.43, 147.62, 152.36, 153.47.

EXAMPLE 32

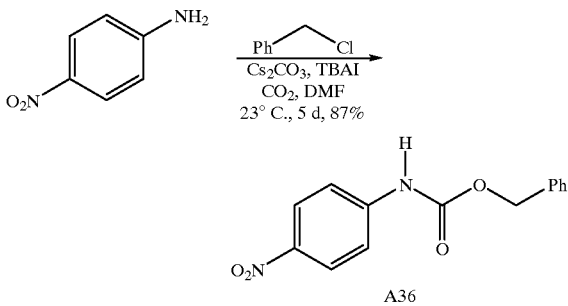

A36

Preparation of carbamate A36. To a solution of p-nitroaniline (0.29 g, 2 mmol) in anhydrous N,N-dimethylformamide (10 mL), cesium carbonate (2.04 g, 6 mmol, 3 eq.) and tetrabutylammonium iodide (2.32g, 6 mmol, 3 eq.) are added to the solution with vigorous stirring. Carbon dioxide is bubbled into the solution continuously for 1 hour before benzyl chloride (0.76 g, 6 mmol, 3 eq.) is added. The reaction is allowed to proceed at room temperature with constant carbon dioxide bubbling and stirring for 5 days. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (1:1 hexanes:EtOAc) affords carbamate A36 (0.47 g, 87%) as a pale yellow oil. Data for A36: IR (thin film) 3390, 3085, 3061, 3029, 2955, 2929, 2857, 1735, 1596, 1472, 1253, 1096 cm⁻¹ ¹H NMR (360 MHz, CDCl₃) δ4.73 (s, 2H), 6.65–8.05 (m, 10H). ¹³C NMR (90 MHz, CDCl₃) δ54.34, 111.04, 126.24, 127.57, 128.30, 128.56, 129.01, 129.52, 136.28, 153.74.

EXAMPLE 33

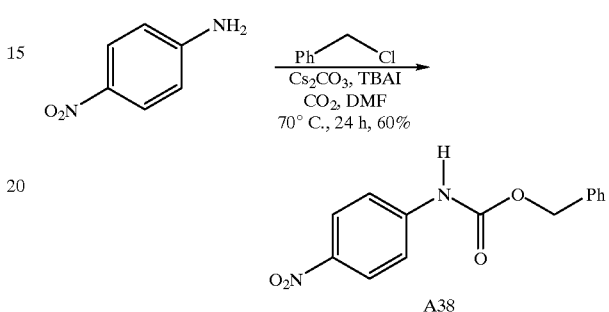

A38

Preparation of carbamate A38. To a solution of p-nitroaniline (0.29 g, 2 mmol) in anhydrous N,N-dimethylformamide (10 mL), cesium carbonate (2.0 g, 6 mmol, 3 eq.) and tetrabutylammonium iodide (2.32 g, 6 mmol, 3 eq.) are added to the solution with vigorous stirring. Carbon dioxide is bubbled into the solution continuously for 1 hour before benzyl chloride (0.76 g, 6 mmol, 3 eq.) is added. The reaction is allowed to proceed at a temperature of 70° C. with constant carbon dioxide bubbling and stirring for 24 hours. The reaction mixture is quenched with water and extracted with ethyl acetate (3×30 mL). The combined organic layers were washed with water (2×30 mL), brine (30 mL) and dried over anhydrous sodium sulfate. Evaporation of the solvent and subjection of the crude residue to column chromatography (1:1 hexanes:EtOAc) affords carbamate A36 (0.31 g, 60%) as a pale yellow oil.

EXAMPLE 34

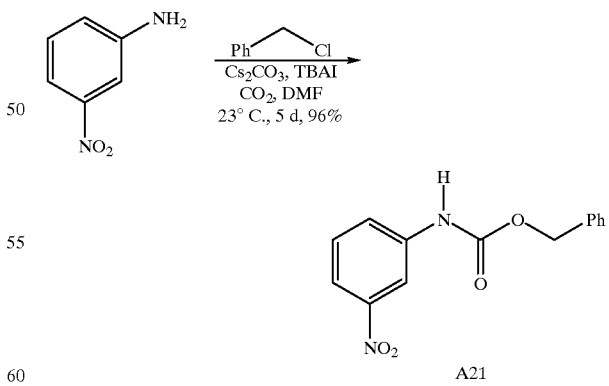

A21

Preparation of carbamate A21. To a solution of m-nitroaniline (0.28 g, 2 mmol) in anhydrous N,N-dimethylformamide (10 mL), cesium carbonate (1.96 g, 6 mmol, 3 eq.) and tetrabutylammonium iodide (2.22 g, 6 mmol, 3 eq.) are added to the solution with vigorous stirring.

Carbon dioxide is bubbled into the solution continuously for 1 hour before benzyl chloride (0.76 g, 6 mmol, 3 eq.) is added. The reaction is allowed to proceed at room temperature with constant carbon dioxide bubbling and stirring for 5 days. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (1:1 hexanes:EtOAc) affords carbamate A21 (0.49 g, 96%) as a pale yellow oil. Data for A21: IR (thin film) 3421, 3085, 3061, 3028, 2954, 2922, 2852, 1619, 1526, 1451, 1346, 1236 cm$^{-1}$. $^1$H NMR (360 MHz, CDCl$_3$) δ4.54 (s, 2H), 6.77–7.39 (m, 9H). $^{13}$C NMR (90 MHz, CDCl$_3$) δ54.11, 106.55, 111.35, 118.0, 126.49, 127.37, 128.90, 129.79, 137.08, 149.49.

EXAMPLE 35

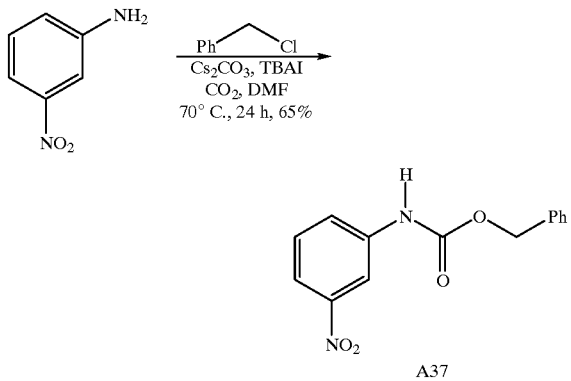

Preparation of carbamate A37. To a solution of m-nitroaniline (0.27 g, 2 mmol) in anhydrous N,N-dimethylformamide (10 mL), cesium carbonate (1.9 g, 6 mmol, 3 eq.) and tetrabutylammonium iodide (2.16 g, 6 mmol, 3 eq.) are added to the solution with vigorous stirring. Carbon dioxide is bubbled into the solution continuously for 1 hour before benzyl chloride (0.76 g, 6 mmol, 3 eq.) is added. The reaction is allowed to proceed at a temperature of 70° C. with constant carbon dioxide bubbling and stirring for 24 hours. The reaction mixture is quenched with water and extracted with ethyl acetate (3×30 mL), water (2×30 mL), brine (30 mL) and dried over anhydrous sodium sulfate. Evaporation of the solvent and subjection of the crude residue to column chromatography (2:1 hexanes:EtOAc) affords carbamate A37 (0.334 g, 65%) as an oil.

EXAMPLE 36

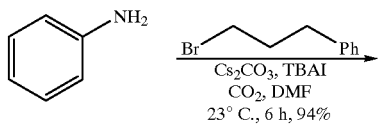

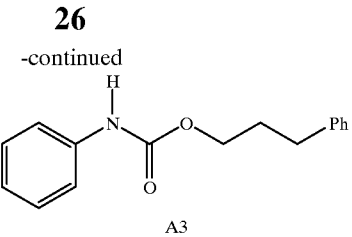

Preparation of carbamate A3. To a solution of aniline (186 mg, 2 mmol) in anhydrous N,N-dimethylformamide (10 mL), cesium carbonate (1.96 g, 6 mmol, 3 eq.) and tetrabutylammonium iodide (2.22 g, 6 mmol, 3 eq.) are added. Carbon dioxide (flow rate≅25–30 mL/min) is bubbled through the solution for 1 hour before 1-bromo-3-phenylpropane (1.2 g, 6 mmol, 3 eq.) is added to the solution in one portion. The reaction proceeds at room temperature with constant carbon dioxide bubbling for 6 hours after which all the starting material (aniline) is consumed. The reaction mixture is poured into water (~30 mL) and extracted with ethyl acetate (3×30 mL) thoroughly. The organic layer is washed with water (2×30 mL), brine (30 mL), and dried over anhydrous sodium sulfate. Evaporation of the solvent and subjection to silica gel column chromatography (5:1 hexanes:EtOAc) affords carbamate A3 (480 mg, 94%) as an oil. Data for A3: IR (thin film) 3320, 3137, 3060, 3026, 2954, 2858, 1700, 1600, 1539, 1443, 1213, 1220, 1063 cm$^{-1}$. $^1$H NMR (360 MHz, CDCl$_3$) δ2.12 (m, 2H), 2.80 (t, 2H, J=7.53 Hz), 4.28 (t, 2H, J=6.52 Hz), 7.17–7.61 (m, 11H). $^{13}$C NMR (90 MHz, CDCl$_3$) δ29.67, 30.44, 64.53, 118.6, 123.29, 125.93, 128.33, 128.94, 137.86, 141.14, 153.6.

EXAMPLE 37

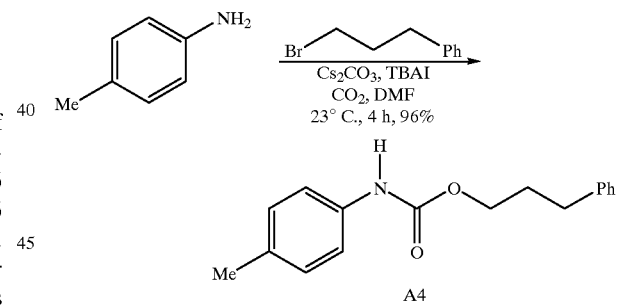

Preparation of carbamate A4. p-toluidine (0.21 g, 2 mmol) is dissolved in anhydrous N,N-dimethylformamide (10 mL) to make a 0.2 M solution. Cesium carbonate (1.96 g, 6 mmol, 3 eq.) and tetrabutylammonium iodide (2.22 g, 6 mmol, 3 eq.) are added to the solution with vigorous stirring. After, carbon dioxide is allowed to pass through the suspension for 1 hour. 1-Bromo-3-phenylpropane (1.2 g, 6 mmol, 3 eq.) is added to the reaction mixture with constant stirring. The reaction proceeds at ambient temperature with carbon dioxide bubbling through for a time period of 4 hours after which the p-toluidine is consumed. The reaction is then washed with water (2×30 mL), brine (30 mL), and dried over anhydrous sodium sulfate. Removal of solvent in vacuo and subjection to column chromatography (5:1 hexanes:EtOAc) affords the carbamate A4 (0.520 g, 96%) as an oil. Data for A4: IR (thin film) 3318, 3061, 3026, 2950, 2922, 2860, 1704, 1599, 1530, 1453, 1408, 1315, 1223, 1065 cm$^{-1}$. $^1$H NMR (360 MHz, CDCl$_3$) δ2.00 (m, 2H), 2.31 (s, 3H), 2.69

(t, 2H, J=7.53 Hz), 4.18 (t, 2H, 7.05–7.33 (m, 11H). $^{13}$C NMR (90 MHz, CDCl$_3$) δ20.54, 30.38, 31.94, 64.6, 125.80, 126.97, 128.94, 129.28, 129.42, 132.60, 135.29, 141.06, 155.65.

EXAMPLE 38

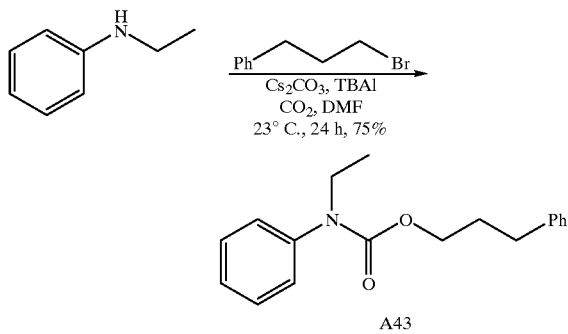

A43

Preparation of carbamate A43. To a solution of N-ethylaniline (0.121 g, 1 mmol) in anhydrous N,N-dimethylformamide (5 mL), cesium carbonate (1.0 g, 3 mmol, 3 eq.) and tetrabutylammonium iodide (1.11 g, 3 mmol, 3 eq.) are added. Carbon dioxide (flow rate≅25–30 mL/min) is bubbled through the solution for 1 hour before 1-bromo-3-phenylpropane (0.60 g, 3 mmol, 3 eq.) is added to the solution. The reaction proceeds at room temperature with constant carbon dioxide bubbling for 24 h at ambient temperature. The reaction mixture is poured into water (30 mL) and extracted with ethyl acetate (3×3 mL) thoroughly. The organic layer is then washed with water (2×30 mL), brine (30 mL), and dried over anhydrous sodium sulfate. Evaporation of the solvent and subjection to silica gel column chromatography (9:1 hexanes:EtOAc) affords carbamate A43 (0.212 g, 75%) as an oil. Data for A43: IR (thin film) 3085, 3060, 3024, 2966, 2925, 2866, 2851, 1732, 1598, 1505, 1452, 1370, 1268 cm$^{-1}$. $^1$H NMR (360 MHz, CDCl$_3$) δ0.98 (t, 3H, J=7.04 Hz), 1.71–1.83 (m, 2H), 2.52 (t, 2H, J=6.52 Hz), 3.10–3.23 (m, 4H), 6.95–7.16 (m, 10H). $^{13}$C NMR (90 MHz, CDCl$_3$) δ12.27, 28.94, 33.92, 44.91, 49.84, 111.88, 115.40, 125.84, 126.12, 128.33, 128.46, 129.20, 141.76, 147.84.

EXAMPLE 39

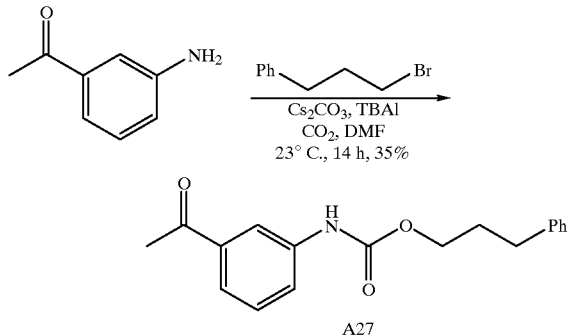

A27

Preparation of carbamate A27. To a solution of 3-aminoacetophenone (0.2 g, 1.5 mmol) in anhydrous N,N-dimethylformamide (10 mL), cesium carbonate (1.4 g, 4.3 mmol, 3 eq.) and tetrabutylammonium iodide (1.63 g, 4.3 mmol, 3 eq.) are added to the solution with vigorous stirring. Carbon dioxide is bubbled into the solution continuously for 1 hour before 1-bromo-3-phenylpropane (0.86 g, 4.3 mmol, 3 eq.) was added. The reaction is allowed to proceed at room temperature with constant carbon dioxide bubbling and vigorous stirring for 14 hours. The reaction mixture is quenched with water and extracted with ethyl acetate (3×30 mL). The combined organic layers are then washed with water (2×30 mL), brine (30 mL) and dried over anhydrous sodium sulfate. Evaporation of the solvent and subjection of the crude residue to column chromatography (1:1 hexanes:EtOAc) affords carbamate A27 (0.15 g, 35%) as a pale oil. Data for A27: IR (thin film) 3336, 3085, 3062, 3026, 2955, 2856, 1715, 1599, 1549, 1509, 1413, 1332, 1216, 1112 cm$^{-1}$. $^1$H NMR (360 MHz, CDCl$_3$) δ1.85–1.93 (m, 2H), 2.48 (s, 3H), 2.58–2.67 (m, 2H), 3.09–3.44 (m, 2H), 3.7 (bs, N$\underline{H}$), 7.04–7.25 (m, 9H). $^{13}$C NMR (90 MHz, CDCl$_3$) δ26.66, 30.77, 33.23, 63.24, 111.28, 117.38, 117.50, 125.93, 128.30, 128.38, 129.20, 138.01, 141.41, 148.41, 198.68.

EXAMPLE 40

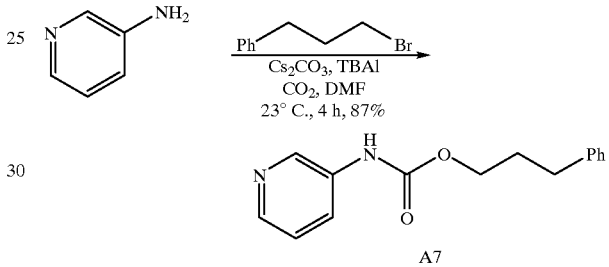

A7

Preparation of carbamate A7. To a solution of 3-aminopyridine (0.190 g, 2 mmol) in anhydrous N,N-dimethylformamide (10 mL) are added cesium carbonate (1.96 g, 6 mmol, 3 eq.) and tetrabutylammonium iodide (2.22 g, 6 mmol, 3 eq.). Carbon dioxide is then bubbled through the turbid solution at ambient temperature for 1 hour in one portion 1-bromo-3-phenylpropane is added (1.2 g, 6 mmol, 3 eq.) and the reation is stirred at room temperature for 4 hours. The reaction is quenched with water and extracted with ethyl acetate (3×30 mL). The organic layer is washed with water (2×30 mL), brine (30 mL), and dried over anhydrous sodium sulfate. Evaporation of the solvent results in a yellow oil which is purified via column chromatogaphy (1:1 hexanes:EtOAc) to afford carbamate A7 (0.350 g, 87%) as a yellow oil. Data for A7: IR (thin film) 3227, 3184, 3121, 3026, 2956, 2925, 2855, 1727, 1608, 1552, 1484, 1300, 1230, 1070 cm$^{-1}$. $^1$H NMR (360 MHz, CDCl$_3$) δ1.85 (m, 2H), 2.54 (t, 2H, J=7.53 Hz), 4.01 (t, 2H, J=6.52 Hz), 6.93–7.86 (m, 10H). $^{13}$C NMR (90 MHz, CDCl$_3$) δ30.39, 32.06, 64.92, 126.0, 128.32, 128.41, 140.06, 141.02, 143.91, 153.76.

EXAMPLE 41

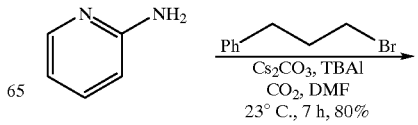

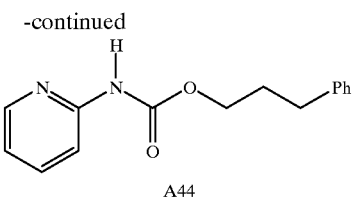

A44

Preparation of carbamate A44. To a solution of 2-aminopyridine (0.2 g, 2 mmol) in anhydrous N,N-dimethylformamide (11 mL), cesium carbonate (1.96 g, 6 mmol, 3 eq.) and tetrabutylammonium iodide (2.22 g, 6 mmol, 3 eq.) are added to the solution with vigorous stirring. Carbon dioxide is bubbled into the solution continuously for 1 hour before 1-bromo-3-phenylpropane (1.2 g, 6 mmol, 3 eq.) is added. The reaction is allowed to proceed at ambient temperature with constant carbon dioxide bubbling and stirring for 7 hours. The reaction mixture is quenched with water and extracted with ethyl acetate (3×30 mL). The combined organic layers are rinsed with water (2×30 mL), brine (30 mL) and dried over anhydrous sodium sulfate. Evaporation of the solvent and subjection of the crude residue to column chromatography (1:1 hexanes:EtOAc) affords carbamate A44 (0.41 g, 80%) as a pale yellow oil. Data for A44: IR (thin film) 3280, 3183, 3083, 3059, 3025, 2931, 2857, 1729, 1648, 1586, 1513, 1495, 1439, 1374, 1331, 1306 cm$^{-1}$. $^1$H NMR (360 MHz, CDCl$_3$) δ1.97–1.99 (m, 2H), 2.6–2.75 (m, 2H), 4.20–4.30 (m, 2H) 6.99–7.30 (m, 6H), 8.1–8.70 (m, 4H). $^{13}$C NMR (90 MHz CDCl$_3$) δ30.87, 33.08, 64.55, 106.79, 112.43, 125.84, 128.30, 138.32, 141.37, 146.77, 158.25.

EXAMPLE 42

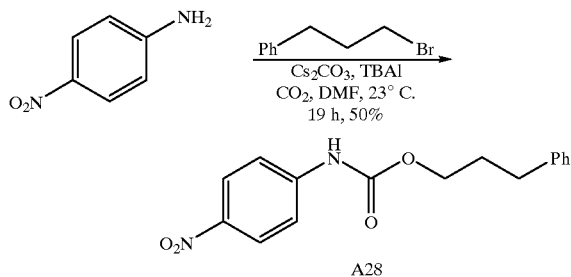

A28

Preparation of carbamate A28. To a solution of p-nitroaniline (0.28 g, 2 mmol) in anhydrous N,N-dimethylformamide (10 mL), cesium carbonate (1.96 g, 6 mmol, 3 eq.) and tetrabutylammonium iodide (2.22 g, 6 mmol, 3 eq.) are added to the solution with vigorous stirring. Carbon dioxide is bubbled into the solution continuously for 1 hour before 1-bromo-3-phenylpropane (1.2 g, 6 mmol, 3 eq.) is added. The reaction is allowed to proceed at room temperature with constant carbon dioxide bubbling and stirring for 19 hours. The reaction mixture is quenched with water and extracted with ethyl acetate (3×30 mL). The combined organic layers were washed with water (2×30 mL), brine (30 mL) and dried over anhydrous sodium sulfate. Evaporation of the solvent and subjection of the crude residue to column chromatography (1:1 hexanes:EtOAc) affords carbamate A28 (0.30 g, 50%) as a pale yellow oil. Data for A28: IR (thin film) 3336, 3085, 3026, 2955, 2856, 1715, 1599, 1549, 1509, 1413, 1332, 1216, 1112cm$^{-1}$. $^1$H NMR(360 MHz, CDCl$_3$) δ1.82 (m, 2H), 2.56 (t, 2H, J=7.09 Hz), 4.05 (t, 2H, J=6.48 Hz), 7.00–8.02 (m, 10H). $^{13}$C NMR (90 MHz, CDCl$_3$) δ30.24, 32.01, 65.29, 117.64, 125.14, 126.05, 128.30, 129.42, 140.89, 142.81, 144.01, 152.84.

EXAMPLE 43

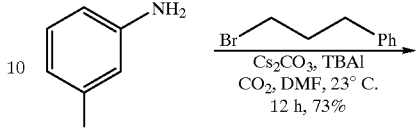

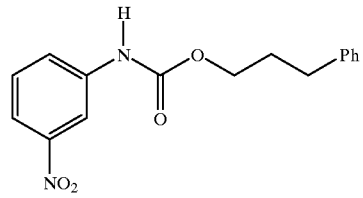

A17

Preparation of carbamate A17. To a solution of m-nitroaniline (0.28 g, 2 mmol) in anhydrous N,N-dimethylformamide (10 mL), cesium carbonate (1.96 g, 6 mmol, 3 eq.) and tetrabutylammonium iodide (2.22 g, 6 mmol, 3 eq.) are added to the solution with vigorous stirring. Carbon dioxide is bubbled into the solution continuously for 1 hour before 1-bromo-3-phenylpropane (1.2 g, 6 mmol, 3 eq.) is added. The reaction is allowed to proceed at room temperature with constant carbon dioxide bubbling and stirring for 12 hours. The reaction mixture is quenched with water and extracted with ethyl acetate (3×30 mL). The combined organic portions are washed with water (2×30 mL), brine (30 mL) then dried over anhydrous sodium sulfate. Evaporation of the solvent and subjection of the crude residue to column chromatography (1:1 hexanes:EtOAc) afforded carbamate A17 (0.440 g, 73%) as a pale yellow oil. Data for A17: IR (thin film) 3325, 3086, 3062, 3026, 2955, 2925, 2856, 1710, 1532, 1350, 1283, 1222 cm$^{-1}$ $^1$H NMR (360 MHz, CDCl$_3$) δ1.89 (m, 2H), 2.54 (t, 2H, J=7.53 Hz), 4.05 (t, 2H, J=6.52 Hz), 6.76–812 (m, 10H). $^{13}$C NMR (90 MHz, CDCl$_3$) δ30.35, 32.09, 65.20, 113.26, 117.95, 124.08, 126.06, 128.46, 129.82, 139.19, 140.99, 148.66, 153.25.

EXAMPLES 43–69

Efficient Solid Phase Synthesis of Carbamates from Non-Aromatic Amines.

The present invention further provides a simple and mild method for the solid phase synthesis of carbamates. In the presence of TBAI, a variety of non-aromatic amines are coupled to Merrifield's resin, which in this embodiment functions as the organic electrophile. During the reaction, CO$_2$ is bubbled through the reaction mixture and carbamate formation is thereby facilitated, which results in coupling of the amine to the resin through formation of a CO$_2$ bridge. The invention produces substantially carbamates, in respectable to excellent yields. Although good results are obtained at room temperature, yields are improved if the reactions are carried out at 60° C. Surprisingly, carbamates of aniline derivatives and aminopyridines are formed successfully in moderate to excellent yields.

It will be obvious to one of ordinary skill that solid supports and resins having amine groups, instead of electrophiles, covalently attached to their surfaces can likewise be used to synthesize immobilized carbamates. In this embodiment, the electrophile is supplied in soluble form, and the resulting carbamate has the opposite orientation relative to the support compared to embodiments where the electrophile is immobilized, as in the following examples.

In a further embodiment of the present invention, resin-bound carbamates are easily released from the resin by treatment with LiAlH$_4$ in THF. Cleavage liberates the corresponding N-methyl secondary amine.

EXAMPLE 44

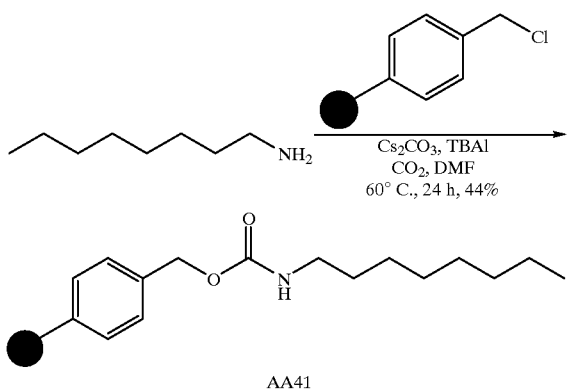

AA41

Preparation of carbamate AA41: Into a stirred solution of n-octylamine (0.646 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of the reaction is then raised to 60° C., after which carbon dioxide is then passed into the suspension for 15 minutes. Merrifield's resin (1 g, 2 mmol, 1 eq.) is added in one portion and the reaction is allowed to further react at 60° C. for 24 hours with constant carbon dioxide bubbling. The solution is then cooled to room temperature and filtered through a coarse fitted disc. The resin is subsequently washed with 20 mL aliquots of water, methanol/water (1:1 v/v), water, tetrahydrofuran, dichloromethane, and methanol in the given order and then dried in vacuo to yield the desired carbamate AA41 (1.04 g, 44%) as a solid. Data for AA41: IR (KBr pellet) 3400, 3320, 2980, 2950, 2930, 2915, 2825, 1729, 1710, 1595, 1500, 1480, 1450, 1400, 1230, 1040, 1020, 740, 695 cm$^{-1}$.

EXAMPLE 45

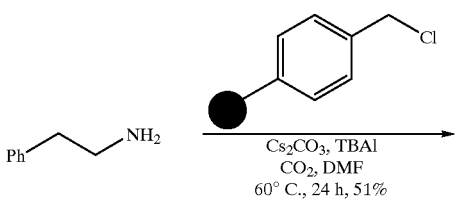

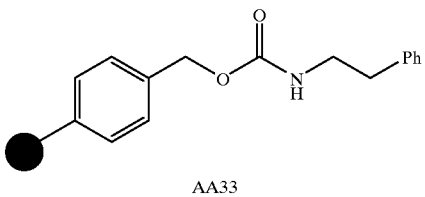

AA33

Preparation of carbamate AA33: Phenethylamine (0.61 g, 5 mmol, 2.5 eq.) is dissolved in N,N-dimethylformamide (40 mL) to make a 0.2 M solution. Cesium carbonate (2.44 g, 7.5 mmol, 3.75 eq.) and tetrabutylammonium iodide (2.77 g, 7.5 mmol, 3.75 eq.) are added to the solution under vigorous stirring. Dry carbon dioxide is allowed to pass into the stirred suspension at room temperature for 1 hour. The temperature of reaction is then raised to 60° C., after which Merrifield's resin (1 g, 2 mmol, 1 eq.) is added and the reaction is allowed to continue with stirring at 60° C. for 24 hours with constant carbon dioxide bubbling. The reaction is subsequently cooled to room temperature and filtered through a coarse fitted filter funnel. The resin is subsequently washed with 20 mL aliquots of water, methanol/water (1:1 v/v), water, tetrahydrofuran, dichloromethane, and methanol in the given order and then dried in vacuo to yield the desired carbamate AA33 (1.10 g, 51%) as a solid. Data AA33: IR (KBr pellet) 3400, 3080, 3060, 3040, 2920, 2850, 1940, 1729, 1710, 1595, 1525, 1485, 1450, 1210, 1130, 1000, 840, 695 cm$^{-1}$.

EXAMPLE 46

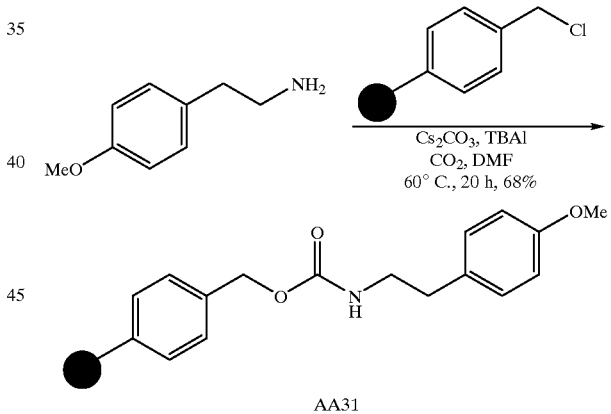

AA31

Preparation of carbamate AA31: Into a stirred solution of p-methoxyphenethylamine (0.76 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of the reaction is then raised to 60° C., after which carbon dioxide is passed into the suspension for 2 hours. Merrifield's resin (1 g, 2 mmol, 1 eq.) is added in one portion and the reaction is further allowed to continue at 60° C. for 20 hours with constant carbon dioxide bubbling. The reaction is then cooled to room temperature and filtered through a coarse fitted disc. The resin is subsequently washed with 20 mL aliquots of water, methanol/water (1:1 v/v), water, tetrahydrofuran, dichloromethane, and methanol in the given order and then dried in vacuo to yield desired carbamate AA31 (1.20 gm, 68%) as a solid. Data for AA31:

IR (KBr pellet) 3080, 3060, 3020, 2920, 2860, 1950, 1875, 1825, 1722, 1595, 1510, 1495, 1440, 1210, 1150, 1020, 815, 740, 695 cm$^{-1}$.

EXAMPLE 47

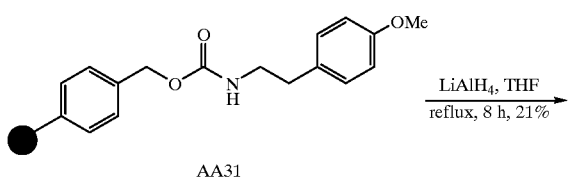

AA31

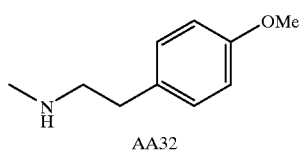

AA32

Cleavage of solid phase support of carbamate AA31: Under a nitrogen atmosphere resin bound carbamate AA31 (1.02 g, 1.12 nunol) is placed in a flame dried flask containing anhydrous tetrahydrofuran (20 mL). Lithium aluminum hydride (377 mg, 10 mmol) is then added in portions to the resulting suspension over a period of 20 minutes, and the reaction is refluxed under a nitrogen atmosphere for 8 hours. The reaction is subsequently cooled to 0° C. and quenched with dropwise addition of water (0.4 mL) followed by 15% sodium hydroxide solution (0.4 mL) and finally water (1.1 mL). The reaction mixture is filtered through a coarse filtration frit to remove aluminum salts, and the residual salts are washed diethyl ether (4×8 mL). The combined filtrate and washings are dried over sodium sulfate and concentrated in vacuo. The crude product is then purified by flash chromatography (1:1 hexanes:ethyl acetate), to yield the desired N-methylated product AA32 (0.039 g, 21%).

EXAMPLE 48

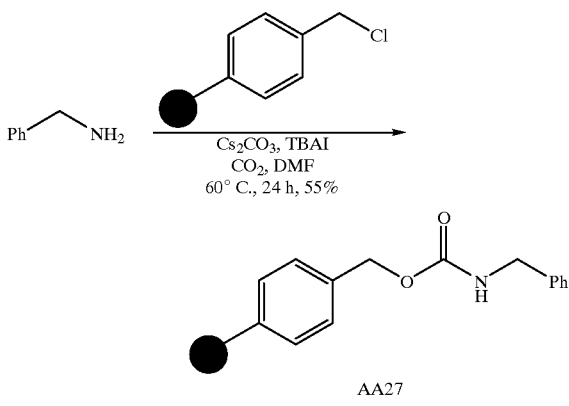

AA27

Preparation of carbamate AA27: Into a stirred solution of benzylamine (0.536 g, 5 mmol, 2.5 eq.) in anhydrous N,N-dimethylformamide (40 mL), Cesium carbonate (2.44 g, 7.5 mmol, 3.75 eq.) and tetrabutylammonium iodide (2.77 g, 7.5 mmol, 3.75 eq.) are added. Carbon dioxide is then passed into the reaction at room temperature for 1 hour. The temperature of the reaction is then raised to 60° C., after which Merrifield's resin (1 g, 2 mmol, 1 eq.) is added in one portion and the reaction was further continued at 60° C. for 24 hours with constant carbon dioxide bubbling. The suspension is then cooled to room temperature and filtered through a coarse flitted disc. The resin is subsequently washed with 20 mL aliquots of water, methanol/water (1:1 v/v), water, tetrahydrofuran, dichloromethane and methanol in the given order and then dried in vacuo to yield desired carbamate AA27 (1.09 g, 55%) as a solid. Data for AA27: IR (KBr pellet) 3400, 3350, 3080, 3060, 3020, 3040, 2920, 2840, 1950, 1870, 1780, 1722, 1590, 1520, 1505, 1495, 1465, 1210, 1120, 1020, 750, 695 cm$^{-1}$.

EXAMPLE 49

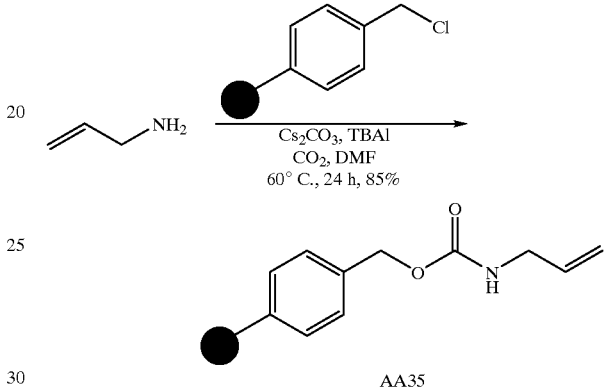

AA35

Preparation of carbamate AA35: Into a stirred solution of allylamine (0.29 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of reaction is raised to 90° C., after which carbon dioxide is bubbled into the stirred suspension for 3 hours. The suspension is then cooled to 60° C. and Merrifield's resin (1 g, 2 mmol, 1 eq.) is added in one portion and the mixture is stirred at the same temperature for 24 hours with constant carbon dioxide bubbling. The solution is then cooled to room temperature and filtered through a coarse fitted filter disc. The resin is subsequently washed with 20 mL aliquots of water, methanol/water (1:1 v/v), water, tetrahydrofuran, dichloromethane and methanol in the given order. and then dried in vacuo to yield desired carbamate AA36 (1.10 gm, 85%) as a solid. Data for AA36: IR (KBr pellet) 3420, 3320, 3080, 3060, 3020, 2935, 2850, 1722, 1712, 1650, 1595, 1525, 1500, 1450, 1215, 750, 695 cm$^{-1}$.

EXAMPLE 50

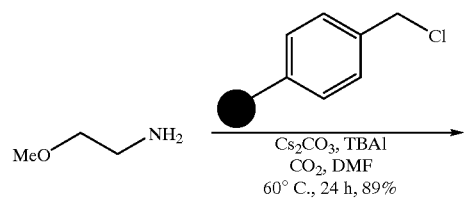

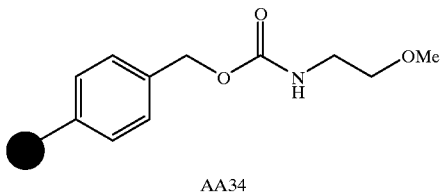

AA34

Preparation of carbamate AA34: To a solution of 2-methoxyethylamine (0.37 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. Carbon dioxide is then bubbled into the reaction at room temperature for 1 hour. The temperature of reaction is raised to 60° C., after which, Merrifield's resin (1 g, 2 mmol, 1 eq.) is added and reaction is allowed to further react at 60° C. for 24 hours with continuous $CO_2$ bubbling. The reaction mass was cooled to room temperature and filtered through a coarse fitted filter disc. The insoluble resin is then washed with 20 mL aliquots of water, methanol/water (1:1 v/v), water, tetrahydrofuran, dichloromethane and methanol in the given order and then dried in vacuo to yield desired carbamate AA34 (1.06 g, 89%) as a solid. Data for AA34: IR (KBr pellet) 3420, 3320, 3080, 3060, 3040, 2925, 2840, 1722, 1590, 1525, 1495, 1450, 1220, 1110, 1020, 830, 740, 695 cm$^{-1}$.

EXAMPLE 51

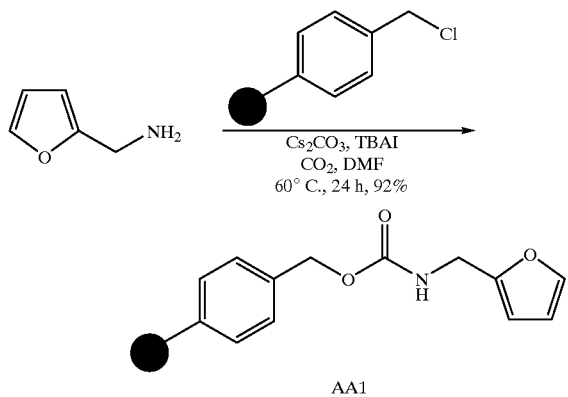

AA1

Preparation of carbamate AA1: Into a stirred solution of furfurylamine (0.47 g, 5 mmol, 2.5 eq.) in anhydrous N,N-dimethylformamide (40 mL), cesium carbonate (2.44 g; 7.5 mmol, 3.75 eq) and tetrabutylammonium iodide (2.8 g, 7.5 mmol, 3.75 eq) are added. The temperature of the suspension is raised to 90° C., after which carbon dioxide (flow rate≅25–30 mL/min) is bubbled into the stirred suspension at 90° C. for 3 hours. The reaction is then cooled to 60° C. and Merrifield's resin (1 g, 2 mmol, 1 eq.) is added in one portion and the mixture is stirred at 60° C. for 24 hours with constant carbon dioxide bubbling. The suspension is then cooled to room temperature and filtered through a coarse fitted filter funnel. The resin is subsequently washed with 20 ml aliquots of water, methanol/water (1:1 v/v), water, tetrahydrofuran, dichloromethane, and methanol in the given order and then dried in vacuo to yield the desired carbamate AA1 (1.2 g, 92%) as a solid. Data for AA1: IR (KBr pellet) 3475, 3360, 3080, 3060, 3030, 2915, 2865, 1701, 1600, 1530, 1450, 1345, 1225, 1120, 1010, 998, 850, 730, 695 cm$^{-1}$.

EXAMPLE 52

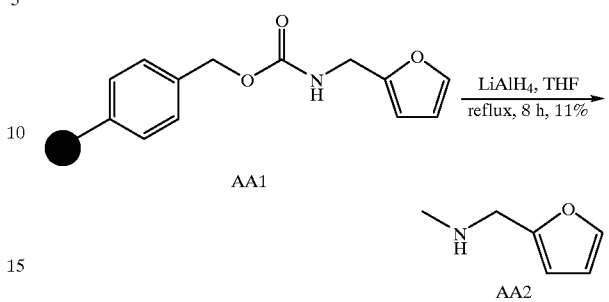

Cleavage of solid phase support for carbamate AA1: Under a nitrogen atmosphere, resin bound carbamate AA1 (1.07 g, 1.65 mmol) is placed in a flame dried round-bottom flask containing anhydrous tetrahydrofuran (20 mL). Lithium aluminum hydride (0.377 g, 10 mmol) is added in portions to the resulting slurry over a period of 20 minutes. The reaction is then refluxed under nitrogen atmosphere for 8 hours. The reaction is subsequently cooled to 0° C. and quenched with dropwise addition of water (0.4 mL), followed by 15% aqueous sodium hydroxide solution (0.4 mL), and finally water (1.1 mL). The reaction mixture is then filtered through a coarse filtration frit to remove aluminum salts, and the residual salts are washed diethyl ether (4×8 mL). The combined filtrate and washings are dried over sodium sulfate and concentrated in vacuo. The crude product was then purified by flash chromatography (1:1 hexanes-:ethyl acetate) to yield the desired N-methylated product AA2 (0.21 g, 11%).

EXAMPLE 53

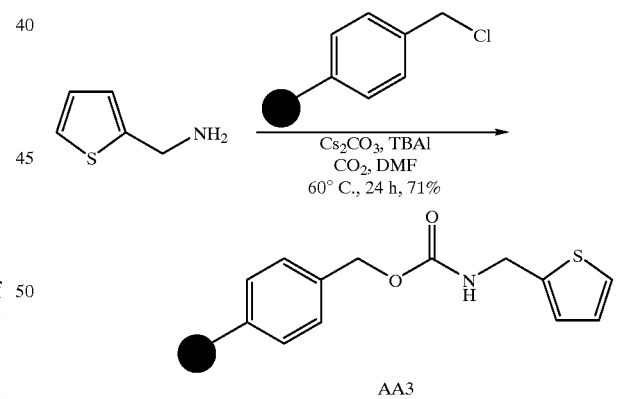

AA3

Preparation of carbamate AA3: To a solution of 2-Thiophenemethylamine (0.56 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of reaction is raised to 90° C., after which carbon dioxide (flow rate 25–30 mL/min) is bubbled into the stirred suspension at 90° C. for 3 h. The reaction mass is then cooled to 60° C., and Merrifield's resin (1 g, 2 mmol, 1 eq.) is added into the reaction and stirred at 60° C. for 24 hours with constant carbon dioxide bubbling. The reaction mass is subsequently cooled to room temperature and filtered through a coarse fitted filter disc. The resin is subsequently washed with 20 mL aliquots of water, methanol/water (1:1 v/v), water, tetrahydrofuran, dichloromethane and methanol in the given order and then dried in vacuo to yield desired carbamate AA3 (1.15 g, 71%) as a solid. Data for AA3: IR (KBr pellet) 3430, 3325, 3080, 3040, 3020, 2930, 2850, 1705, 1600, 1510, 1465, 1360, 1210, 1150, 1110, 1020, 950, 830, 750, 690, 530 cm$^{-1}$.

EXAMPLE 54

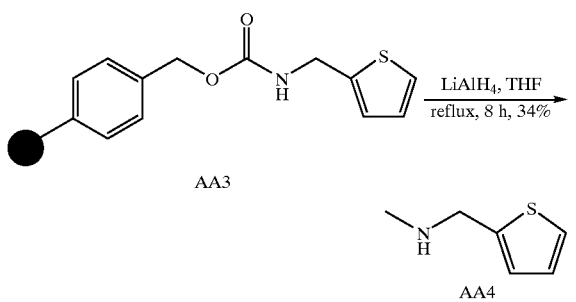

Cleavage of solid phase support for carbamate AA3: Under a nitrogen atmosphere, resin bound carbamate AA3 (1.02 g, 1.25 mmol) is placed in a flame dried round-bottomed flask containing anhydrous tetrahydrofuran (20 mL). Lithium aluminum hydride (0.377 g, 10 mmol) is added in portions to the resulting suspension over a period of 20 minutes. The reaction mass is then refluxed under nitrogen atmosphere for 8 hours. The reaction is subsequently cooled to 0° C. and quenched by dropwise addition of water (0.4 mL), followed by 15% aqueous sodium hydroxide solution (0.4 mL), and finally water (1.1 mL). The reaction mixture is filtered through a coarse filtration frit to remove aluminum salts, and the residual salts are washed diethyl ether (4×8 mL). The combined filtrate and washings are dried over sodium sulfate and concentrated in vacuo. The crude product is then purified by flash chromatography (1:1 hexanes: ethyl acetate) to yield the desired N-methylated product AA4 (0.55 g, 34%). Data for AA4: $^1$H NMR (360 MHz, CDCl$_3$) δ2.01 (bs, N$\underline{H}$), 2.35 (s, 3H), 3.82 (s, 2H), 6.83–7.11 (m, 3H).

EXAMPLE 55

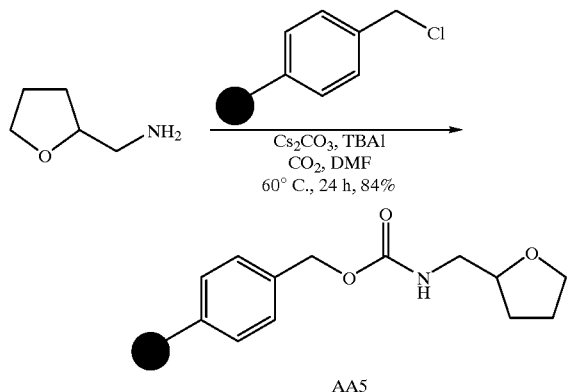

Preparation of carbamate AA5: Tetrahydrofurfurylamine (0.51 g, 5 mmol, 2.5 eq.) is dissolved in N,N-dimethylformamide (40 mL) to make a 0.2 M solution. Cesium carbonate (2.44 g, 7.5 mmol, 3.75 eq.) and tetrabutylammonium iodide (2.77 g, 7.5 mmol, 3.75 eq.) are added to the solution with vigorous stirring. The temperature of reaction is then raised to 60° C., after which carbon dioxide (flow rate 25–30 mL/min) is allowed to pass into the stirred suspension for 3 hours. Merrifield's resin (1 g, 2 mmol, 1 eq.) is added in into the reaction and the mixture is stirred at 60° C. for 24 h with constant carbon dioxide bubbling. The reaction mass is subsequently cooled to room temperature and filtered through a coarse fitted filter disc. The resin is subsequently washed with 20 mL aliquots of water, methanol/water (1:1 v/v), water, tetrahydrofuran, dichloromethane, and methanol in the given order and then dried in vacuo to yield desired carbamate AA5 (1.17 g, 84%) as a solid. Data for AA5: IR (KBr pellet) 3475, 3360,3080, 3065, 3025, 2915, 2865, 1722, 1600, 1510, 1490, 1470, 1375, 1225, 1070, 1020, 815, 775, 695, 530 cm$^{-1}$.

EXAMPLE 56

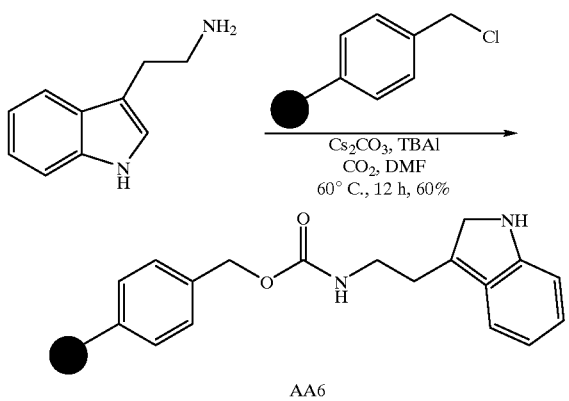

Preparation of carbamate AA6: Into a stirred solution of tryptamine (0.80 g, 5 mmol, 2.5 eq.) in anhydrous N,N-dimethylformamide (40 mL), cesium carbonate (2.44 g, 7.5 mmol, 3.75 eq.) and tetrabutylarunonium iodide (2.77 g, 7.5 mmol, 3.75 eq.) are added. The temperature of reaction is raised to 60° C., after which carbon dioxide is bubbled into the stirred suspension at 60° C. for 10 h. Merrifield's resin (1 g, 2 mmol, 1 eq) is added in one portion into the reaction and continued at 60° C. for 12 h with constant carbon dioxide bubbling. The reaction mass is then cooled to room temperature and filtered through a coarse fitted filter disc. The resin is subsequently washed with 20 mL aliquots of water, methanol/water (1:1 v/v), water, tetrahydrofuran, dichloromethane, and methanol in the given order and then dried in vacuo to yield desired carbamate AA6 (1.18 g, 60%) as a solid. Data for AA6: IR (KBr pellet) 3450, 3385, 3080, 3065, 3015, 2920, 2835, 1708, 1580, 1495, 1475, 1420, 1380, 1360, 1200, 1105, 1080, 995, 801, 720, 695, 530 cm$^{-1}$.

EXAMPLE 57

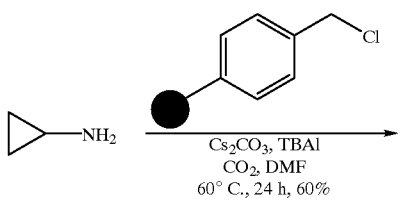

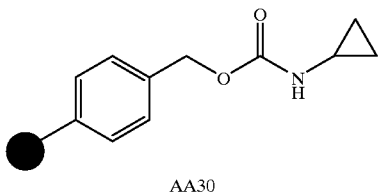

AA30

Preparation of carbamate AA30: To a solution of cyclopropylamine (0.850 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. Carbon dioxide is bubbled into the reaction at room temperature for 1 hour. The temperature of reaction is then raised to 60° C., after which, Merrifield's resin (1 g, 2 mmol, 1 eq.) is added, and reaction was allowed to continue at 60° C. for a further 24 hours with continuous $CO_2$ bubbling. The reaction is cooled to room temperature and filtered through a coarse fitted disc. The insoluble resin is then washed with 20 mL aliquots of water, methanol/water (1:1 v/v), water, tetrahydrofuran, dichloromethane and methanol in the given order and then dried in vacuo to yield desired carbamate AA30 (1.05 g, 60%) as a solid. Data for AA30: IR (KBr pellet) 3380, 3080, 3060, 3040, 3020, 2925, 2830, 1920, 1722, 1600, 1525, 1495, 1450, 1365, 1345, 1220, 1210, 1195, 1020, 810, 750, 695 $cm^{-1}$.

EXAMPLE 58

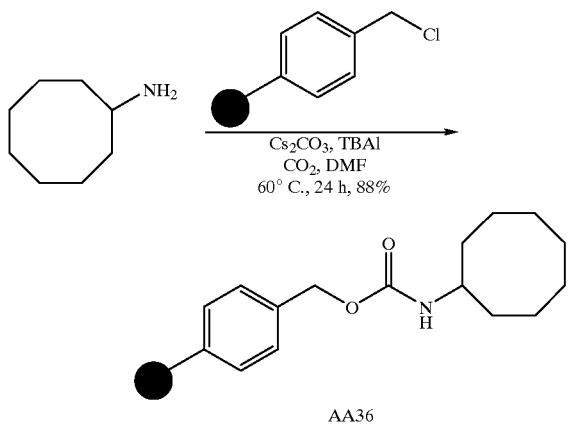

AA36

Preparation of carbamate AA36: Into a stirred solution of cyclooctylamine (0.64 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of the reaction is raised to 90° C., after which carbon dioxide is bubbled into the stirred suspension at 90° C. for 3 hours. The suspension is then cooled to 60° C. and Merrifield's resin (1 g, 2 mmol, 1 eq.) is added in one portion into the reaction and the mixture is stirred at the same temperature for 24 hours with constant carbon dioxide bubbling. The reaction is then cooled to room temperature and filtered through a coarse fitted disc. The resin is subsequently washed with 20 mL aliquots of water, methanol/water (1:1 v/v), water, tetrahydrofuran, dichloromethane and methanol in the given order and then dried in vacuo to yield desired carbamate AA36 (1.23 g, 88%) as a solid. Data for AA36: IR (KBr pellet) 3450, 3370, 3080, 3060, 3035, 2915, 2820, 1722, 1595, 1500, 1480, 1440, 1205, 1030, 820, 770, 695 530 $cm^{-1}$.

EXAMPLE 59

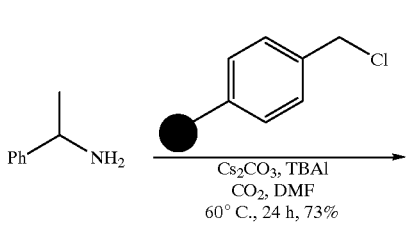

AA39

Preparation of carbamate AA39: Into a stirred solution of D,L-α-methylbenzylamine (0.61 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of reaction is then raised to 60° C., after which carbon dioxide is passed into the reaction for 15 minutes. Merrifield's resin (1 g, 2 mmol, 1 eq.) is added in one portion and the reaction is fturther continued at 60° C. for 24 hours with constant carbon dioxide bubbling. The suspension is then cooled to room temperature and filtered through a coarse flitted disc. The resin is subsequently washed with 20 mL aliquots of water, methanol/water (1:1 v/v), water, tetrahydrofuran, dichloromethane, and methanol in the given order and then dried in vacuo to yield desired carbamate AA39 (1.17 g, 73%) as a solid. Data for AA39: IR (KBr pellet) 3400, 3320, 3080, 3060, 3020, 2980, 2825, 1900, 1850, 1735, 1722, 1595, 1480, 1440, 1330, 1210, 1040, 1015, 720, 695 $cm^{-1}$.

EXAMPLE 60

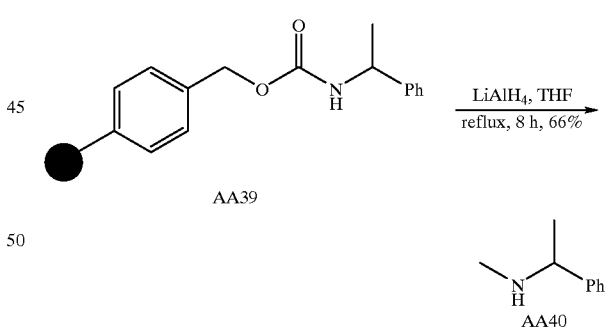

AA40

Cleavage of solid phase support of carbamate AA39: Under a nitrogen atmosphere, resin bound carbamate AA39 (1.06 g, 1.31 mmol) is placed in a flame dried round-bottom flask containing anhydrous tetrahydrofuran (20 mL). Lithium aluminum hydride (0.38 g, 10 mmol) is added in portions to the resulting suspension over a period of 20 minutes. The reaction is then refluxed under a nitrogen atmosphere for 8 hours. The reaction is subsequently cooled to 0 ° C. and quenched with dropwise addition of water (0.4 mL), followed by 15% sodium hydroxide solution (0.4 mL) and finally water (1.1 mL). The reaction mixture is then filtered through a coarse filtration frit to remove aluminum salts, and the residual salts are washed diethyl ether (4×8 mL). The combined filtrate and washings are dried over sodium sulfate and concentrated in vacuo. The crude product is then purified by flash chromatography (1:1 hexanes:ethyl acetate), to yield desired N-methylated product AA39 (0.118 g, 66%).

EXAMPLE 61

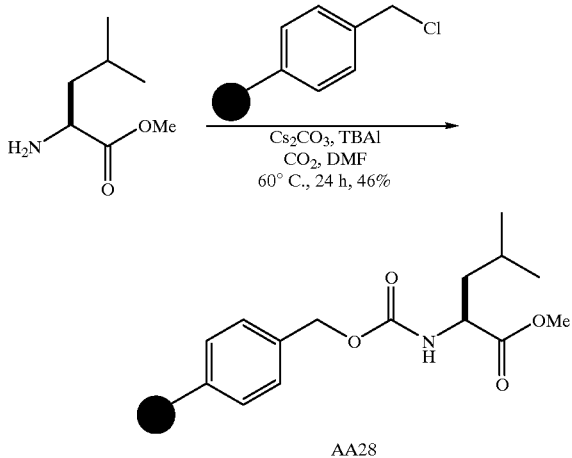

AA28

Preparation of carbamate AA28: Leucine methyl ester (0.508 g, 5 mmol, 2.5 eq.) was dissolved in N,N-dimethylformamide (40 mL) to make a 0.2 M solution. Cesium carbonate (2.44 g, 7.5 mmol, 3.75 eq.) and tetrabutylammonium iodide (2.77 g, 7.5 mmol, 3.75 eq.) are added to the solution with vigorous stirring. Carbon dioxide is then allowed to pass into the stirred suspension at room temperature for 1 hour. The temperature of reaction is then raised to 60° C., after which Merrifield's resin (1 g, 2 mmol, 1 eq.) is added and the reaction was continued with stirring at 60° C. for 24 hours with constant carbon dioxide bubbling. The reaction is subsequently cooled to room temperature and filtered through a coarse fitted disc. The resin is washed with 20 mL aliquots of water, methanol/water (1:1 v/v), water, tetrahydrofuran, dichloromethane and methanol in the given order and then dried in vacuo to yield desired carbamate AA28 (1.13 g, 46%) as a solid. Data AA28: IR (KBr pellet) 3420, 3360, 3080, 3040, 3020, 2935, 2840, 1950, 1722, 1595, 1515, 1495, 1450, 1240, 1190, 1160, 810, 750, 695 cm$^{-1}$.

EXAMPLE 62

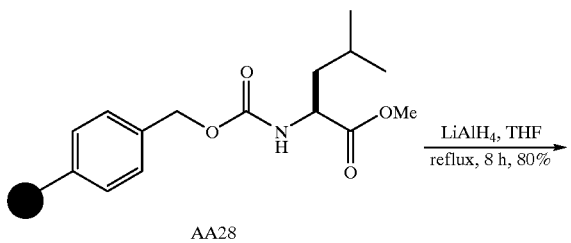

AA28

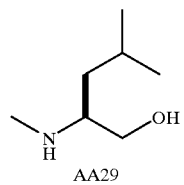

AA29

Cleavage of solid phase support of carbamate AA28: Under nitrogen atmosphere, resin bound carbamate AA28 (1.06 g, 0.865 mmol) is placed in a flame dried round-bottom flask containing anhydrous tetrahydrofuran (20 mL). Lithium aluminum hydride (0.38 g, 10 mmol) is then added in portions to the resulting suspension over a period of 20 minutes, and the reaction is refluxed under a nitrogen atmosphere for 8 hours. The reaction is subsequently cooled to 0° C. and quenched with dropwise addition of water (0.4 mL), followed by 15% sodium hydroxide solution (0.4 mL) and finally water (1.1 mL). The reaction mixture is then filtered through a coarse filtration fit to remove aluminum salts, and the residual salts are washed diethyl ether (4×8 mL). The combined filtrate and washings are dried over sodium sulfate and concentrated in vacuo. The crude product is then purified by flash chromatography (1:1 hexanes:ethyl acetate), to yield the desired N-methylated product AA29 (0.103 g, 80%).

EXAMPLE 63

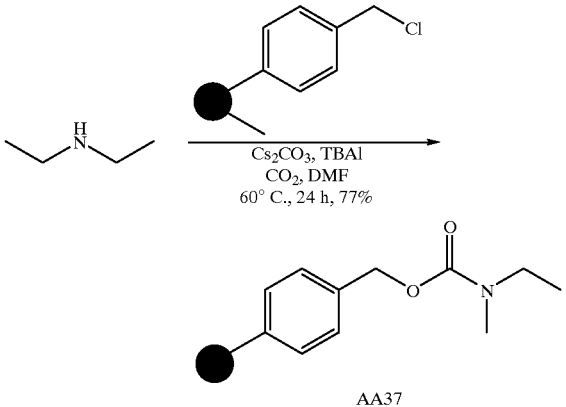

AA37

Preparation of carbamate AA37: To a solution of diethylamine (0.37 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. Carbon dioxide is bubbled into the reaction at room temperature for 1 hour. The temperature of the reaction is raised to 60° C., after which, Merrifield's resin (1 g, 2 mmol, 1 eq) is added and reaction is further equilibrated at 60° C. for further 24 hours with continuous CO$_2$ passing. The reaction mass is cooled to room temperature and filtered through a coarse fitted disc. The insoluble resin is then washed with 20 ml aliquots of water, methanol/water (1:1 v/v); water, tetrahydrofuran, dichloromethane, and methanol in the given order and then dried in vacuo to yield desired carbamate AA37 (1.1 g, 77%) as a solid. Data for AA37: IR (KBr pellet) 3030, 3040, 3020, 2990, 2920, 1709, 1595, 1495, 1480, 1450, 1425, 1375, 1350, 1250, 1175, 1080, 980, 800, 740, 695, 595, 530 cm$^{-1}$.

EXAMPLE 64

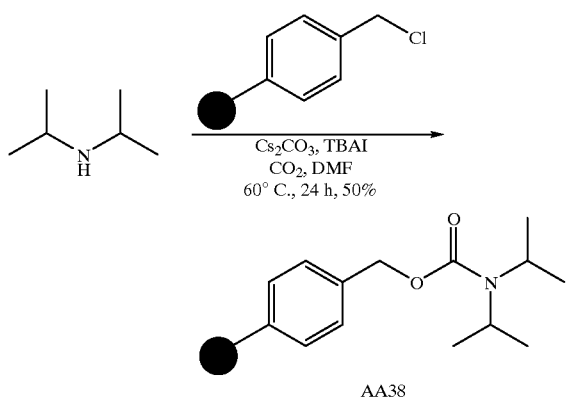

AA38

Preparation of carbamate AA38: To a solution of diisopropylamine (0.51 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. Carbon dioxide is then bubbled into the reaction at room temperature for 1 hour. The temperature of reaction is raised to 60° C., after which, Merrifield's resin (1 g, 2 mmol, 1 eq.) is added and reaction is allowed to react further at 60° C. for 24 hours with continuous CO$_2$ bubbling. The reaction is cooled to room temperature and filtered through a coarse fitted disc. The insoluble resin is then washed with 20 mL aliquots of water, methanol/water (1:1 v/v), water, tetrahydrofuran, dichloromethane and methanol in the given order and then dried in vacuo to yield the desired carbamate AA38 (1.08 g, 50%) as a solid. Data for AA38: IR (KBr pellet) 3400, 3080, 3050, 3020, 2950, 2925, 2850, 1703, 1580, 1490, 1450, 1360, 1290, 1275, 1030, 770, 695, 530 cm$^{-1}$.

EXAMPLE 65

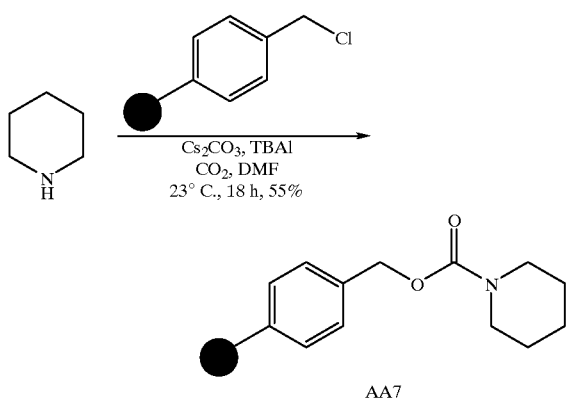

AA7

Preparation of carbamate AA7: To a stirred solution of piperidine (0.43 g, 5 mmol, 2.5 eq.) in anhydrous N,N-dimethylformamide (40 mL), cesium carbonate (2.44 g, 7.5 mmol, 3.75 eq.), tetrabutylammonium iodide (2.77 g, 7.5 mmol, 3.75 eq), and Merrifield's resin (1 g, 2 mmol, 1 eq) are added. Carbon dioxide is then bubbled into the stirred suspension at 23° C. for 18 hours. The reaction mass is subsequently filtered through a coarse fitted filter disc. The insoluble resin is then washed with 20 ml aliquots of water, methanol/water (1:1 v/v), water, tetrahydrofuran, dichloromethane, and methanol in the given order and then dried in vacuo to yield desired carbamate AA7 (1.07 g, 55%) as a solid. Data for AA7: IR (KBr pellet) 3400, 3090, 3060, 3030, 2915, 2870, 2785, 2720, 1950, 1850, 1765, 1698, 1585, 1525, 1480, 1440, 1375, 1345, 1300, 1250, 1225, 1175, 1090, 1030, 1000, 995, 800, 735, 695, 530 cm$^{-1}$.

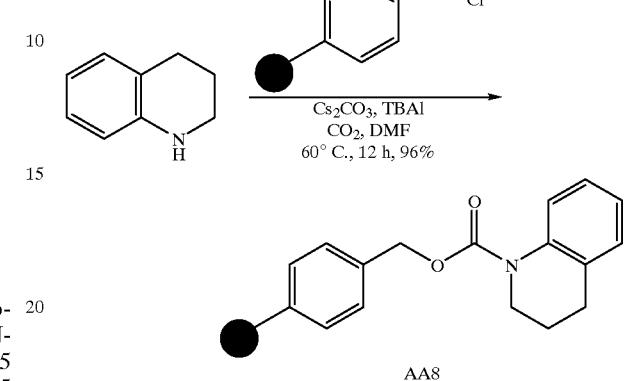

AA8

EXAMPLE 66

Preparation of carbamate AA8: Quinoline (0.67 g, 5 mmol, 2.5 eq.) is dissolved in N,N-dimethylformamide (40 mL) to make a 0.2 M solution. Cesium carbonate (2.44 g, 7.5 mmol, 3.75 eq.) and tetrabutylammonium iodide (2.77 g, 7.5 mmol, 3.75 eq.) are added to the solution under vigorous stirring. The temperature of reaction is then raised to 60° C., after which carbon dioxide is allowed to pass into the stirred suspension at the same temperature for 10 hours. Merrifield's resin (1 g, 2 mmol, 1 eq.) is added and the reaction is continually stirred at 60° C. for 12 hours with constant carbon dioxide bubbling. The reaction mass is then cooled to room temperature and filtered through a coarse fitted filter disc. The resin is subsequently washed with 20 mL aliquots of water, methanol/water (1:1 v/v), water, tetrahydrofuran, dichloromethane and methanol in the given order and then dried in vacuo to yield desired carbamate AA8 (1.27 g, 96%) as a solid. Data for AA8: IR (KBr pellet) 3440, 3075, 3045, 2920, 2850, 1900, 1875, 1740, 1695, 1590, 1560, 1505, 1450, 1395, 1320, 1250, 1220, 1170, 1115, 1010, 950, 905, 830, 820, 740, 695, 530 cm$^{-1}$.

EXAMPLE 67

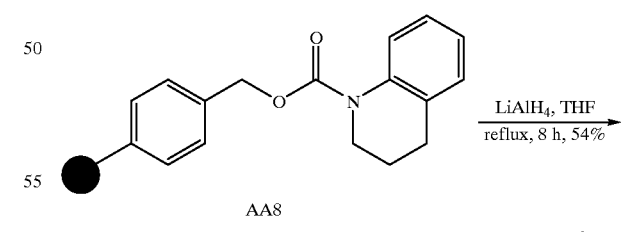

AA8

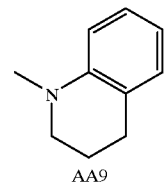

AA9

Cleavage of solid phase support for carbamate AA8: Resin bound carbamate AA8 (1.21 g, 1.83 mmol) is placed

EXAMPLE 68

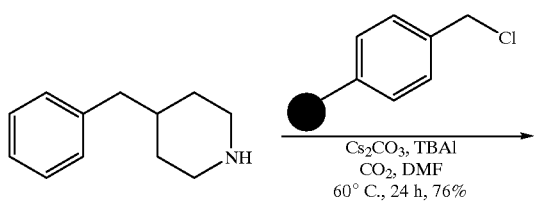

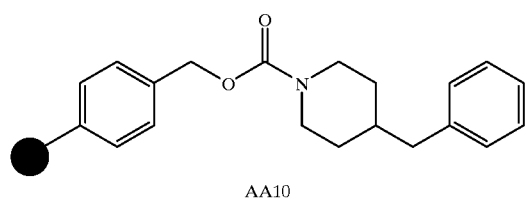

Preparation of carbamate AA10: Into a stirred solution of 4-benzylpiperidine (0.876 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of the reaction is raised to 60° C., after which carbon dioxide is passed into the solution for 3 hours. Merrifield's resin (1 g, 2 mmol, 1 eq.) is added in one portion and the reaction is further continued at 60° C. for 24 hours with constant carbon dioxide bubbling. The reaction mass is then cooled to room temperature and filtered through a coarse fitted filter disc. The resin is subsequently washed with 20 mL aliquots of water, methanol/water (1:1 v/v), water, tetrahydrofuran, dichloromethane and methanol in the given order and then dried in vacuo to yield desired carbamate AA10 (1.26 g, 76%) as a solid. Data for AA10: IR (KBr pellet) 3400, 3080, 3065, 3010, 3025, 2920, 2805, 2795, 2760, 1930, 1850, 1800, 1699, 1590, 1495, 1470, 1350, 1340, 1245, 1215, 1150, 1085, 1078, 1015, 995, 882, 800, 725, 695, 535 cm$^{-1}$.

EXAMPLE 69

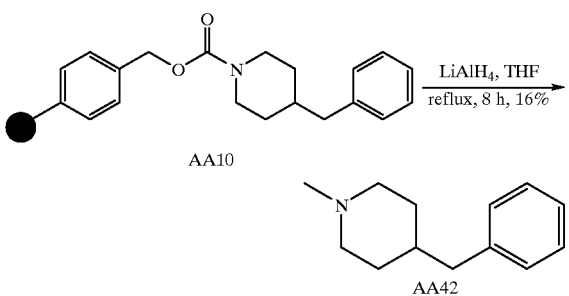

Cleavage of solid phase support of carbamate AA42: Under a nitrogen atmosphere, resin bound carbamate AA10 (1.16 g, 1.39 mmol) is placed in a flame dried round-bottom flask containing anhydrous tetrahydrofuran (20 mL). Lithium aluminum hydride (0.38 g, 10 mmol) is added in portions to the resulting suspension over a period of 20 minutes. The reaction is then refluxed under a nitrogen atmosphere for 8 hours. The reaction is subsequently cooled to 0° C. and quenched with dropwise addition of water (0.4 mL), followed by 15% sodium hydroxide solution (0.4 mL) and finally water (1.1 ml). The reaction mixture is then filtered through a coarse filtration frit to remove aluminum salts, and the residual salts were washed diethyl ether (4×8 mL). The combined filtrate and washings were dried over sodium sulfate and concentrated in vacuo. The crude product is then purified by flash chromatography (1:1 hexanes:ethyl acetate), to yield the desired N-methylated product AA42 (0.43 g, 16%).

EXAMPLE 70

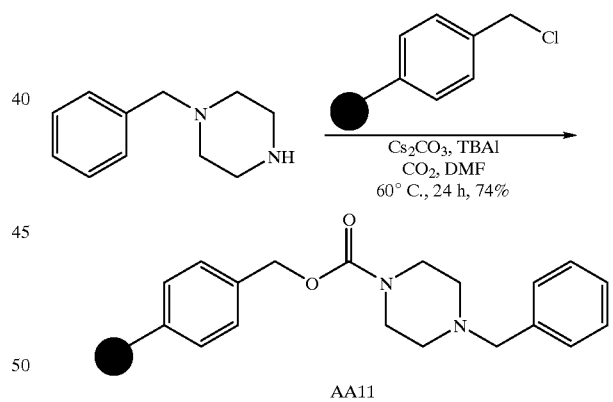

Preparation of carbamate AA11: To a solution of 1-benzylpiperazine (0.88 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of the reaction is raised to 60° C., after which carbon dioxide is bubbled into the reaction for 12 hours. Subsequently, Merrifield's resin (1 g, 2 mmol, 1 eq.) is added and the reaction is continued at 60° C. for a further 24 hours. The reaction mass is cooled to room temperature, and then filtered through a coarse fitted disc. The insoluble resin is then washed with 20 ml aliquots of water, methanol/water (1:1 v/v), water, tetrahydrofuran, dichloromethane, and methanol in the given order and then dried in vacuo to yield desired

--- in a flame dried round-bottom flask containing anhydrous tetrahydrofuran (20 mL) under nitrogen atmosphere. Lithium aluminum hydride (0.38 g, 10 mmol) is added in portions to the resulting suspension over a period of 20 minutes. The reaction is then refluxed under a nitrogen atmosphere for 8 hours. The reaction is subsequently cooled to 0° C. and quenched with dropwise addition of water (0.4 mL), followed by 15% sodium hydroxide solution (0.4 mL) and finally water (1.1 mL). The reaction mixture is then filtered through a coarse filtration frit to remove insoluble aluminum salts, and the residual salts are washed diethyl ether (4×8 mL). The combined filtrate and washings are dried over sodium sulfate and concentrated in vacuo. The crude product is then purified by flash chromatography (1:1 hexanes:ethyl acetate), to yield the desired N-methylated product AA9 (0.154 g, 54%). Data for AA9: $^{1}$H NMR (360 MHz, CDCl$_3$) δ1.99 (m, 2 H), 2.78 (t, 2 H, J=6.48 Hz), 2.88 (s, 3 H), 3.22 (t, 2 H, J=5.76 Hz), 6.58–7.26 (m, 4 H).

carbamate AA11 (1.25 g, 74%) as a solid. Data for AA11: IR (KBr pellet) 3450, 3080, 3060, 3025, 2920, 2805, 2760, 1920, 1850, 1790, 1701, 1595, 1490, 1450, 1350, 1285, 1210, 1130, 1010, 910, 695, 720, 695, 530 cm$^{-1}$.

EXAMPLE 71–86

Efficient Solid Phase Synthesis of Carbamates from Aromatic Amines

Under substantially similar conditions to those above, the inventor has surprisingly found that solid-phase carbamates are also synthesized in good yields from comparatively unreactive aromatic amines by the methods of the present invention. Furthermore, these carbamates can also be cleaved to yield corresponding secondary N-methyl amines.

EXAMPLE 71

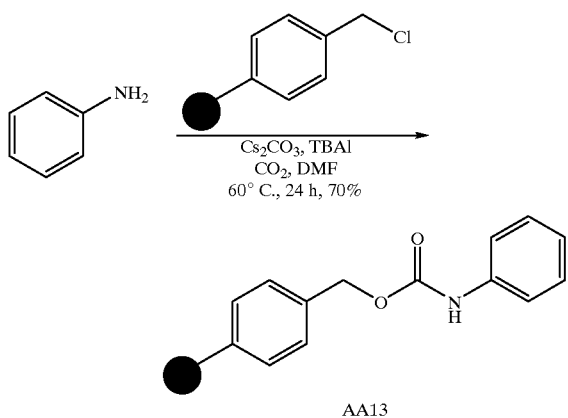

AA13

Preparation of carbamate AA13: Aniline (0.54 g, 5 mmnol, 2.5 eq.) is dissolved in N,N-dimethylformamide (40 mL) to make a 0.2 M solution. Cesium carbonate (2.44 g, 7.5 mmol, 3.75 eq.) and tetrabutylammonium iodide (2.77 g, 7.5 mmol, 3.75 eq.) are added to the solution with vigorous stirring. The temperature of reaction mass is then raised to 60° C., after which carbon dioxide is allowed to pass into the stirred suspension for 1 hour. Merrifield's resin (1 g, 2 mmol, 1 eq.) is added into the reaction and the stirring is continued at 60° C. for 24 hours with constant carbon dioxide bubbling. The reaction mass is subsequently cooled to room temperature and filtered through a coarse fitted disc. The resin is subsequently washed with 20 ml aliquots of water, methanol/water (1:1 v/v), water, tetrahydrofuran, dichloromethane and methanol in the given order and then dried in vacuo to yield desired carbamate AA13 (1.12 g, 70%) as a solid. Data for AA13: IR (KBr pellet) 3420, 3300, 3080, 3060, 3040, 2925, 1730, 1600, 1510, 1485, 1445, 1210, 1120, 995, 695 cm$^{-1}$.

EXAMPLE 72

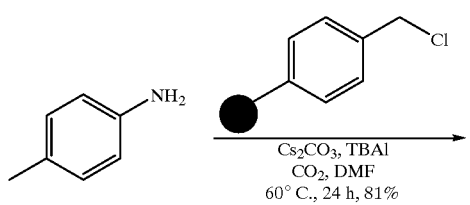

-continued

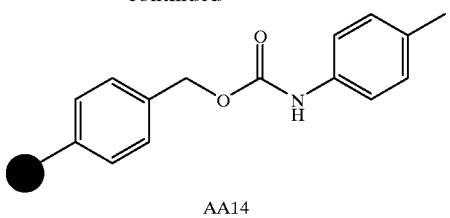

AA14

Preparation of carbamate AA14: Into a stirred solution of p-toluidine (0.54 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. Carbon dioxide is passed into the reaction at room temperature for 1 hour. The temperature of the reaction mass is then raised to 60° C., after which Merrifield's resin (1 g, 2 mmol, 1 eq.) is added in one portion and the reaction is further continued at 60° C. for 24 hours with constant carbon dioxide bubbling. The reaction mass is then cooled to room temperature and filtered through a coarse fitted disc. The resin is subsequently washed with 20 mL aliquots of water, methanol/water (1:1 v/v), water, tetrahydrofuran, dichloromethane, and methanol in the given order and then dried in vacuo to yield desired carbamate AA14 (1.18 g, 81%) as a solid. Data for AA14: IR (KBr pellet) 3420, 3330, 3080, 3060, 3020, 2915, 2850, 1950, 1900, 1722, 1605, 1525, 1445, 1405, 1315, 1200, 1035, 1010, 815, 740, 695 cm$^{-1}$.

EXAMPLE 73

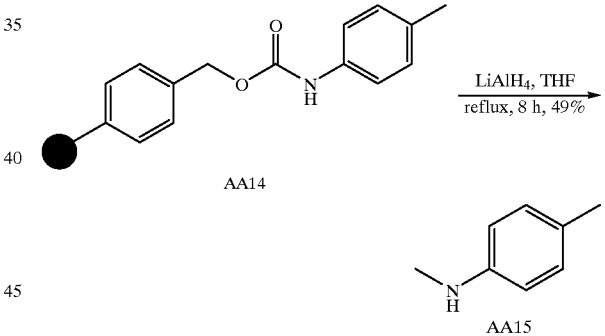

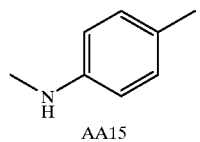

AA15

Cleavage of solid phase support for carbamate AA14: Under a nitrogen atmosphere, resin bound carbamate AA14 (1.13 g, 1.57 mmol) is placed in a flame dried round-bottom flask containing anhydrous tetrahydrofuran (20 mL). Lithium aluminum hydride (0.38 g, 10 mmol) is added in portions to the resulting suspension over a period of 20 minutes. The reaction is refluxed under a nitrogen atmosphere for 8 hours. The reaction is subsequently cooled to 0° C. and quenched with dropwise addition of water (0.4 mL), followed by 15% sodium hydroxide solution (0.4 mL) and finally water (1.1 mL). The reaction mixture is filtered through a coarse filtration frit to remove aluminum salts, and the residual salts are washed diethyl ether (4×8 mL). The combined filtrate and washings are dried over sodium sulfate and concentrated in vacuo. The crude product is then purified by flash chromatography (1:1 hexanes:ethyl acetate), to yield the desired N-methylated product AA15 (0.54 g, 49%). Data for AA15: $^1$H NMR (360 MHz, CDCl$_3$) δ2.26 (s, 3 H), 2.84 (s, 3 H), 6.65–7.27 (m, 4 H).

EXAMPLE 74

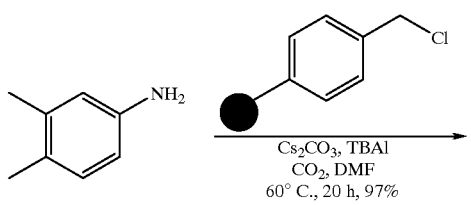

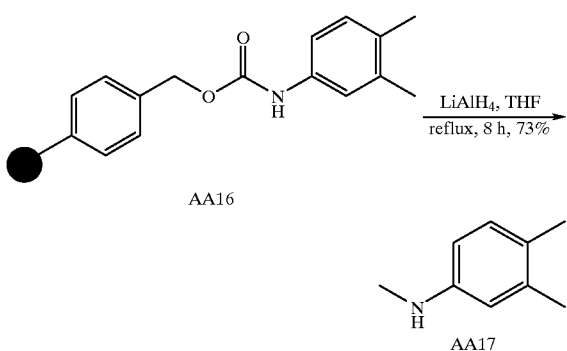

Preparation of carbamate AA16: To a solution of 3,4-dimethylaniline (0.61 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of reaction is raised to 60° C., after which carbon dioxide is bubbled into the solution for 3 hours. Subsequently, Merrifield's resin (1 g, 2 mmol, 1 eq.) is added and the reaction is further stirred at 60° C. for a further 20 hours with continual carbon dioxide bubbling. The reaction mass is cooled to room temperature, and then filtered through a coarse fitted filter disc. The insoluble resin is then washed with 20 mL aliquots of water, methanol/water (1:1 v/v), water, tetrahydrofuran, dichloromethane and methanol in the given order and then dried in vacuo to yield desired carbamate AA16 (1.25 g, 97%) as a solid. Data for AA16: IR (KBr pellet) 3415, 3335, 3050, 2925, 2805, 1950, 1875, 1729, 1610, 1595, 1530, 1450, 1390, 1300, 1270, 1205, 1140, 1050, 995, 795, 750, 695 cm$^{-1}$.

EXAMPLE 75

Cleavage of solid phase support of carbamate AA16: Under a nitrogen atmosphere, resin bound carbamate AA16 (1.14 g, 1.38 mmol) is placed in a flame dried round-bottom flask containing anhydrous tetrahydrofuran (20 mL). Lithium aluminum hydride (0.38 g, 10 mmol) is added in portions to the resulting suspension over a period of 20 minutes. The reaction is then refluxed under av nitrogen atmosphere for 8 hours. The reaction is subsequently cooled to 0° C. and quenched with dropwise addition of water (0.4 mL), followed by 15% sodium hydroxide solution (0.4 mL) and finally water (1.1 mL). The reaction mixture is filtered through a coarse filtration frit to remove aluminum salts, and the residual salts are washed diethyl ether (4×8 mL). The combined filtrate and washings are dried over sodium sulfate and concentrated in vacuo. The crude product is then purified by flash chromatography (1:1 hexanes:ethyl acetate), to yield desired N-methylated product AA17 (0.198 g, 73%). Data for AA17: $^{1}$H NMR (360 MHz, CDCl$_{3}$) δ2.20 (s, 3 H), 2.25 (s, 3 H), 2.81 (s, 3 H), 6.80–7.25 (m, 3 H).

EXAMPLE 76

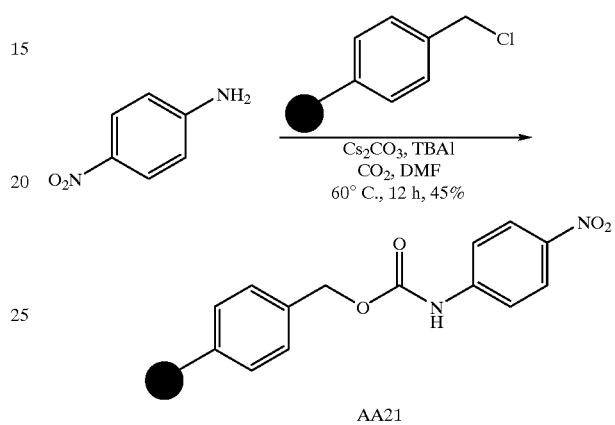

Preparation of carbamate AA21: To a solution of p-nitroaniline (0.69 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of reaction mass is raised to 60° C., after which carbon dioxide is bubbled into the reaction at the same temperature for 10 hours. Subsequently, Merrifield's resin (1 g, 2 mmol, 1 eq.) is added and reaction is further equilibrated at 60° C. for a further 12 hours. The reaction mass is cooled to room temperature, and then filtered through a coarse fitted disc. The insoluble resin is then washed with 20 mL aliquots of water, methanol/water (1:1 v/v), water, tetrahydrofuran, dichloromethane, and methanol in the given order and then dried in vacuo to yield desired carbamate AA21 (1.29 g, 45%) as a solid. Data for AA21: IR (KBr pellet) 3420, 3080, 3060, 3020, 2910, 2840, 1920, 1707, 1600, 1520, 1495, 1450, 1365, 1330, 1270, 1210, 1105, 1020, 960, 900, 850, 695, 530 cm$^{-1}$.

EXAMPLE 77

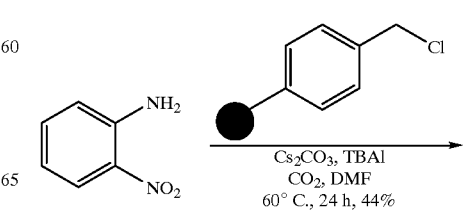

-continued

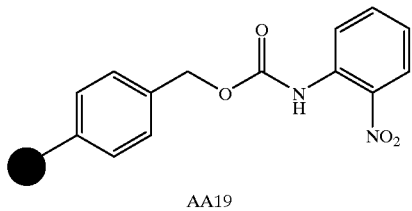

AA19

Preparation of carbamate AA19: o-nitroaniline (0.69 g, 5 mmol, 2.5 eq.) is dissolved in N,N-dimethylformamide (40 mL) to make a 0.2 M solution. Cesium carbonate (2.44 g, 7.5 mmol, 3.75 eq.) and tetrabutylammonium iodide (2.77 g, 7.5 mmol, 3.75 eq.) are added to the solution with vigorous stirring. Carbon dioxide is then allowed to pass into the stirred suspension at room temperature for 1 hour. The temperature of the reaction is then raised to 60° C., after which Merrifield's resin (1 g, 2 mmol, 1 eq.) is added, and the reaction is continued with stirring at 60° C. for 24 hours with constant carbon dioxide bubbling. The reaction is subsequently cooled to room temperature and filtered through a coarse fitted disc. The resin is subsequently washed with 20 mL aliquots of water, methanol/water (1:1 v/v), water, tetrahydrofuran, dichloromethane, and methanol in the given order and then dried in vacuo to yield desired carbamate AA19 (1.11 g, 44%) as a solid. Data for AA19: IR (KBr pellet) 3085, 3065, 3030, 2925, 2850, 1722, 1570, 1520, 1495, 1450, 1385, 1340, 1220, 1180, 1110, 1020, 695 cm$^{-1}$.

EXAMPLE 78

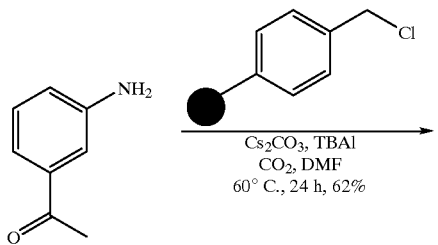

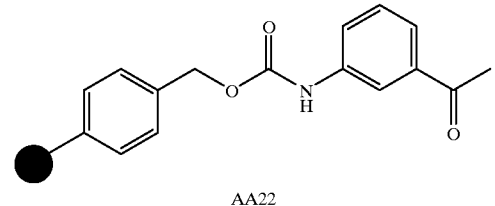

AA22

Preparation of carbamate AA22: Into a stirred solution of 3-aminoacetophenone (0.69 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. The temperature of the reaction is raised to 90° C., after which carbon dioxide is bubbled into the stirred suspension at 90° C. for 3 hours. The reaction mass is then cooled to 60° C. and Merrifield's resin (1 g, 2 mmol, 1 eq.) is added in one portion into the reaction, and the mixture is stirred at the same temperature for 24 hours with constant carbon dioxide bubbling. The reaction is then cooled to room temperature and filtered through a coarse fitted disc. The resin is subsequently washed with 20 mL aliquots of water, methanol/water (1:1 v/v), water, tetrahydrofuran, dichloromethane, and methanol in the given order and then dried in vacuo to yield desired carbamate AA22 (1.15 g, 62%) as a solid. Data for AA22: IR (KBr pellet) 3370, 3080, 3060, 3035, 2915, 2835, 1920, 1870, 1830, 1710, 1690, 1595, 1530, 1495, 1450, 1385, 1335, 1270, 1240, 1205, 1050, 775, 695 cm$^{-1}$.

EXAMPLE 79

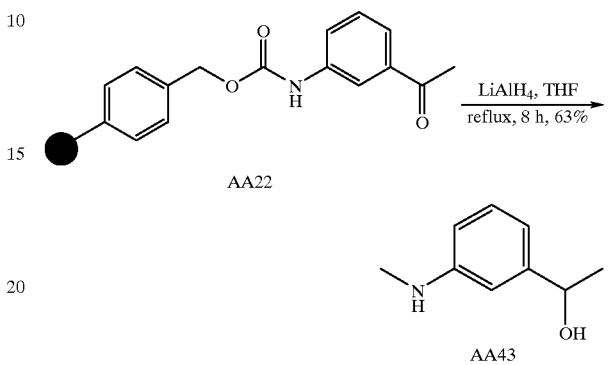

Cleavage of solid phase support of carbamate AA43: Under a nitrogen atmosphere, resin bound carbamate AA43 (1.07 g, 1.15 mmol) is placed in a flame dried round-bottom flask containing anhydrous tetrahydrofuran (20 mL). Lithium aluminum hydride (0.38 g, 10 mmol) is added in portions to the resulting suspension over a period of 20 minutes. The reaction is refluxed under a nitrogen atmosphere for 8 hours. The reaction is subsequently cooled to 0° C. and quenched with dropwise addition of water (0.4 mL), followed by 15% sodium hydroxide solution (0.4 mL), and finally water (1.1 mL). The reaction mixture is then filtered through a coarse filtration fit to remove aluminum salts, and the residual salts are washed diethyl ether (4×8 mL). The combined filtrate and washings are dried over sodium sulfate and concentrated in vacuo. The crude product is then purified by flash chromatography (1:1 hexanes:ethyl acetate), to yield desired N-methylated product AA43 (0.109 g, 63%). Data for AA43: $^1$H NMR (360 MHz, CDCl$_3$) 1.38 (d, 3 H, J=6.44 Hz), 2.73 (s, 3 H), 3.02 (bs, NH, OH), 4.69 (q, 1 H, J=6.44 Hz 6.42–7.10 (m, 4 H).

EXAMPLE 80

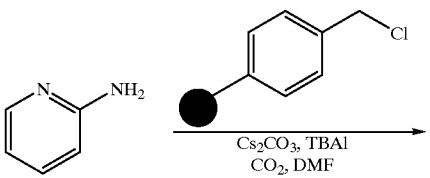

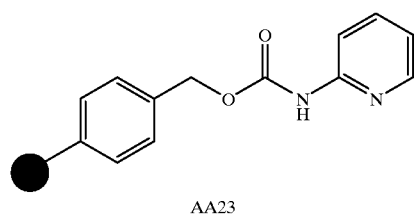

AA23

Preparation of carbamate AA23: 2-aminopyridine (0.470 g, 6 mmol, 2.5 eq.) is dissolved in N,N-dimethylformamide (40 mL) to make a 0.2 M solution. Cesium carbonate (2.44 g, 7.5 mmol, 3.75 eq.) and tetrabutylammonium iodide (2.77 g, 7.5 mmol, 3.75 eq.) are added to the solution under vigorous stirring. Carbon dioxide is then allowed to pass into the stirred suspension at room temperature for 1 hour. The temperature of reaction is then raised to 60° C., after which Merrifield's resin (1 g, 2 mmol, 1 eq.) is added and the reaction is allowed to proceed with stirring at 60° C. for 24 hours with constant carbon dioxide bubbling. The reaction is subsequently cooled to room temperature and filtered through a coarse fitted disc. The resin is then washed with 20 mL aliquots of water, methanol/water (1:1 v/v), water, tetrahydrofuran, dichloromethane and methanol in the given order and then dried in vacuo to yield the desired carbamate AA23 (1.11 g, 66%) as a solid. Data AA23: IR (KBr pellet) 3400, 3085, 3065, 3025, 2930, 2850, 1920, 1722, 1570, 1520, 1490, 1415, 1385, 1300, 1210, 1180, 1170, 1080, 1010, 720, 695 cm$^{-1}$.

EXAMPLE 81

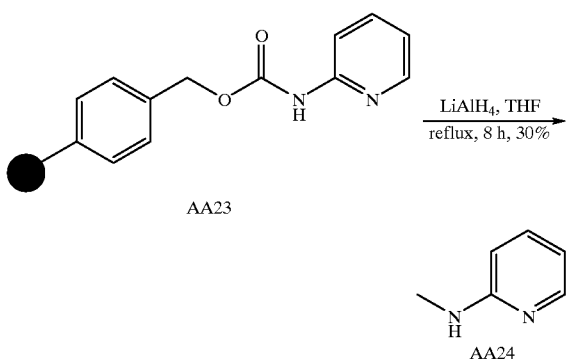

Cleavage of solid phase support of carbamate AA24: Under a nitrogen atmosphere, resin bound carbamate AA24 (1.05 g, 1.25 mmol) is placed in a flame dried round-bottom flask containing anhydrous tetrahydrofuran (20 mL). Lithium aluminum hydride (0.378 g, 10 mmol) is added in portions to the resulting suspension over a time period of 20 minutes. The reaction is then refluxed under a nitrogen atmosphere for 8 hours. The reaction is subsequently cooled to 0° C. and quenched with dropwise addition of water (0.4 mL), followed by 15% sodium hydroxide solution (0.4 mL) and finally water (1.1 mL). The reaction mixture is then filtered through a coarse filtration frit to remove aluminum salts, and the residual salts are washed diethyl ether (4×8 mL). The combined filtrate and washings are dried over sodium sulfate and concentrated in vacuo. The crude product is then purified by flash chromatography (1:1 hexanes:ethyl acetate), to yield the desired N-methylated product AA24 (0.93 g, 30%). Data for AA24: $^{1}$H NMR (360 MHz, CDCl$_3$) δ3.52 (s, 3H), 4.50 (bs, N$\underline{H}$), 7.50–7.62 (m, 1H), 7.80–7.89 (m, 1H), 8.60–8.80 (m, 2H).

EXAMPLE 82

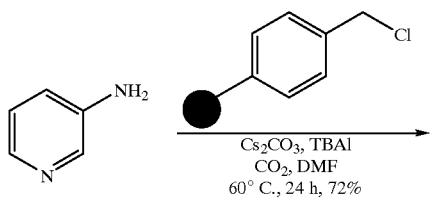

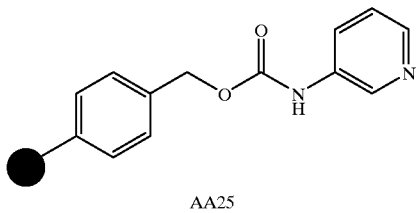

Preparation of carbamate AA25: 3-aminopyridine (0.47 g, 6 mmol, 2.5 eq.) is dissolved in N,N-dimethylformamide (40 mL) to make a 0.2 M solution. Cesium carbonate (2.44 g, 7.5 mmol, 3.75 eq.) and tetrabutylammonium iodide (2.77 g, 7.5 mmol, 3.75 eq.) are added to the solution under vigorous stirring. Carbon dioxide is then allowed to pass into the stirred suspension at room temperature for 1 hour. The temperature of reaction mass was then raised to 60° C., after which Merrifield's resin (1 g, 2 mmol, 1 eq.) is added and the reaction is continued with stirring at 60° C. for 24 hours with constant carbon dioxide bubbling. The reaction is subsequently cooled to room temperature and filtered through a coarse fitted disc. The resin is subsequently washed with 20 mL aliquots of water, methanol/water (1:1 v/v), water, tetrahydrofuran, dichloromethane, and methanol in the given order and then dried in vacuo to yield the desired carbamate AA25 (1.13 g, 72%) as a solid. Data AA25: IR (KBr pellet) 3400, 3080, 3060, 3040, 2915, 2860, 1722, 1595, 1575, 1490, 1480, 1410, 1210, 1050, 1020, 740, 695 cm$^{-1}$.

EXAMPLE 83

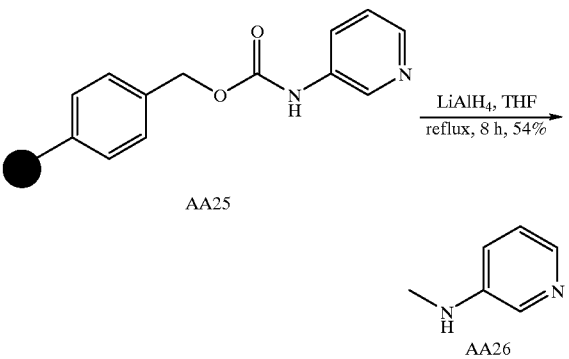

Cleavage of solid phase support of carbamate AA25: Under nitrogen atmosphere resin bound carbamate AA25 (1.13 g, 1.4 mmol) is placed in a flame dried round-bottom flask containing anhydrous tetrahydrofuran (20 mL). Lithium aluminum hydride (0.38 g, 10 mmol) is added in portions to the resulting suspension over a period of 20 minutes. The reaction mass is refluxed under a nitrogen atmosphere for 8 hours. The reaction is subsequently cooled to 0° C. and quenched with dropwise addition of water (0.4 mL), followed by 15% sodium hydroxide solution (0.4 mL) and finally water (1.1 mL). The reaction mixture is filtered through a coarse filtration frit to remove aluminum salts, and the residual salts are washed diethyl ether (4×8 mL). The combined filtrate and washings were dried over sodium sulfate and concentrated in vacuo. The crude product is then purified by flash chromatography (1:1 hexanes:ethyl acetate), to yield the desired N-methylated product AA26 (0.082 g, 54%). Data for AA26: $^{1}$H NMR (360 MHz, CDCl$_3$) 2.73 (s, 3H), 4.81 (bs, N$\underline{H}$), 6.72–8.91 (m, 4H).

EXAMPLE 84

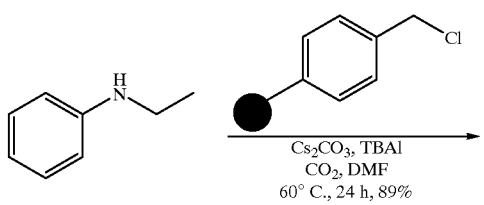

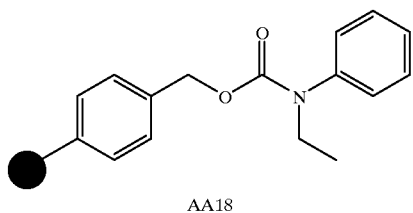

AA18

Preparation of carbamate AA18: Into a stirred solution of N-ethylaniline (0.61 g, 5 mmol, 2.5 eq.) in anhydrous N,N-dimethylformamide (40 mL), cesium carbonate (2.44 g, 7.5 mmol, 3.75 eq.) and tetrabutylammonium iodide (2.77 g, 7.5 mmol, 3.75 eq.) are added. Carbon dioxide is passed into the reaction at room temperature for 1 hour. The temperature of the reaction is then raised to 60° C., after which Merrifield's resin (1 g, 2 mmol, 1 eq.) is added in one portion and the reaction is further continued at 60° C. for 24 hours with constant carbon dioxide bubbling. The suspension is then cooled to room temperature and filtered through a coarse flitted filter disc. The resin is subsequently washed with 20 mL aliquots of water, methanol/water (1:1 v/v), water, tetrahydrofuran, dichloromethane and methanol in the given order and then dried in vacuo to yield desired carbamate AA18 (1.22 g, 89%) as a solid. Data for AA18: IR (KBr pellet) 3090, 3050, 3020, 2915, 1930, 1795, 1722, 1699, 1600, 1490, 1450, 1395, 1300, 1275, 1140, 1120, 1040, 1010, 810, 780,695 cm$^{-1}$.

EXAMPLE 85

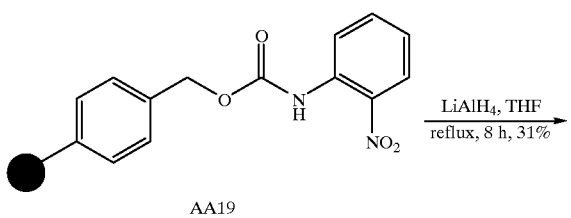

AA19

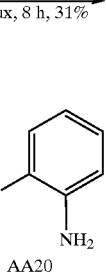

AA20

Cleavage of solid phase support of carbamate AA19: Under a nitrogen atmosphere, resin bound carbamate AA19 (1.01 g, 0.806 mmol) is placed in a flame dried round-bottomed flask containing anhydrous tetrahydrofuran (20 mL). Lithium aluminum hydride (0.38 g, 10 mmol) is added in portions to the resulting suspension over a period of 20 minutes. The reaction mass is then refluxed under a nitrogen atmosphere for 8 hours. The reaction is subsequently cooled to 0° C. and quenched with dropwise addition of water (0.4 mL) followed by 15% sodium hydroxide solution (0.4 mL) and finally water (1.1 mL). The reaction mixture is then filtered through a coarse filtration frit to remove aluminum salts, and the residual salts were washed diethyl ether (4×8 mL). The combined filtrate and washings are dried over sodium sulfate and concentrated in vacuo. The crude product is then purified by flash chromatography (1:1 hexanes:ethyl acetate), to yield the desired N-methylated product AA20 (0.30 g, 31%).

EXAMPLE 86

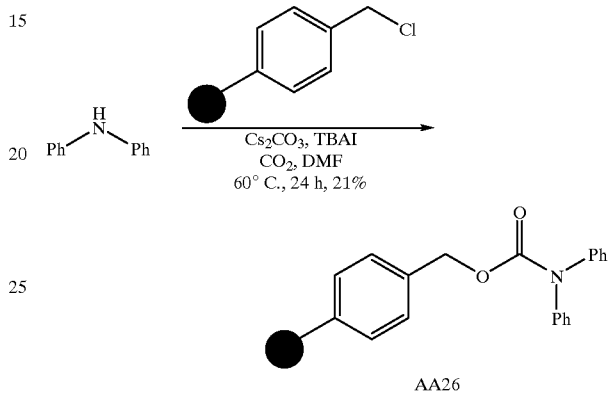

AA26

Preparation of carbamate AA26: To a solution of diphenylamine (0.85 g, 5 mmol, 2.5 eq.) in anhydrous N,N-dimethylformamide (40 mL), Cesium carbonate (2.44 g, 7.5 mmol, 3.75 eq.) and tetrabutylammonium iodide (2.77 g, 7.5 mmol, 3.75 eq.) are added. Carbon dioxide is then bubbled into the reaction at room temperature for 1 hour. The temperature of reaction is raised to 60° C., after which, Merrifield's resin (1 g, 2 mmol, 1 eq.) is added and the reaction is allowed to further react at 60° C. for further 24 hours with continuous CO$_2$ bubbling. The reaction is then cooled to room temperature and filtered through a coarse fitted disc. The insoluble resin is then washed with 20 mL aliquots of water, methanol/water (1:1 v/v), water, tetrahydrofuran, dichloromethane and methanol in the given order and then dried in vacuo to yield desired carbamate AA26 (1.02 g, 21%) as a solid.

EXAMPLE 87–92

Overalkylation of Carbamates Using Activated Halides

In a further embodiment of the present invention, N-alkylated carbamates (dialkyl carbamates) are produced in a "one-pot" reaction. Omission of TBAI, provision of excess organic electrophile, and longer reaction times, promote synthesis of N-alkylated carbamates in good yields. Table 1. In other respects, conditions are substantially similar to those in the preceding Examples. In this embodiment, the N-linked and O-linked moieties that derive from the organic electrophile are necessarily identical.

TABLE 1

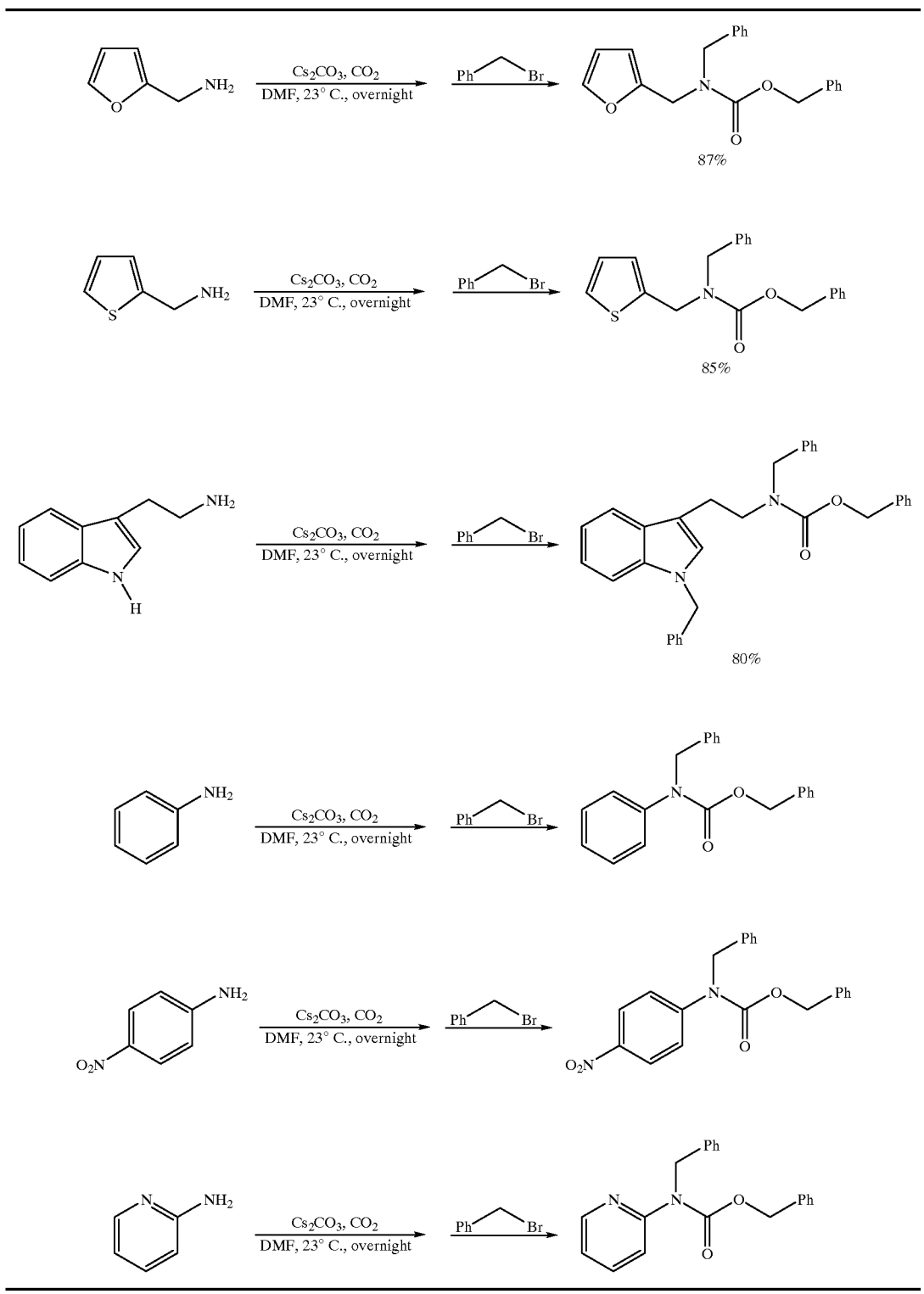

EXAMPLE 93–98

N-alkylation of Carbamates

In an alternative embodiment to that set forth in examples above, chemically different organic electrophiles are used sequentially to first effect carbamate synthesis, and subsequently effect N-alkylation of the preformed carbamate. In this embodiment the N-linked and O-linked moieties that derive from the organic electrophiles are different. As disclosed in FIG. 3, purification of the carbamate prior to N-alkylation is not essential; a "one-pot" carbamation is permitted to proceed essentially to completion, and addition of an excess amount of a second organic electrophile with a further reaction period results in good yield of the N-alkylated carbamate.

EXAMPLE 93

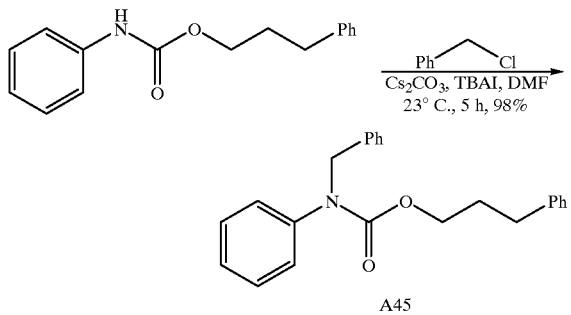

A45

Preparation of dialkyl carbamate A45: Under a nitrogen atmosphere, aniline carbamate A3 (0.11 g, 0.43 mmol) is dissolved in anhydrous N,N-dimethylformamide (5 mL) and with vigorous stirring, cesium carbonate (0.42 g, 1.29 mmol, 3 eq.) and tetrabutylammonium iodide (0.48 g, 1.29 mmol, 3 eq.) are added to the solution and stirred for 30 minutes at ambient temperature. After stirring for 30 minutes, benzyl chloride (0.17 g, 1.29 mmol, 3 eq.) is then added into the suspension. The reaction is allowed to proceed at room temperature with continual stirring for 5 hours. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (5:1 hexanes:EtOAc) afforded carbamate A45 (0.15 g, 98%) as an oil. Data for A45: IR (thin film) 3389, 3085, 3062, 3028, 2952, 2858, 1948, 1876, 1803, 1702, 1597, 1496, 1404, 1275, 1223 cm$^{-1}$. $^1$H NMR (360 MHz, CDCl$_3$) δ1.83 (t, 3H, J=6.7 Hz), 2.48 (t, 2H, J=7.4 Hz), 4.10 (t, 2H, J=6.1 Hz), 4.82 (s, 2H). 7.00–7.27 (m, 15H). $^{13}$C NMR (90 MHz, CDCl$_3$) δ30.51, 31.94, 54.14, 64.93, 125.82, 126.42, 126.83, 127.21, 127.68, 128.31, 128.38, 128.76, 137.98, 141.22, 142.11, 155.73.

EXAMPLE 94

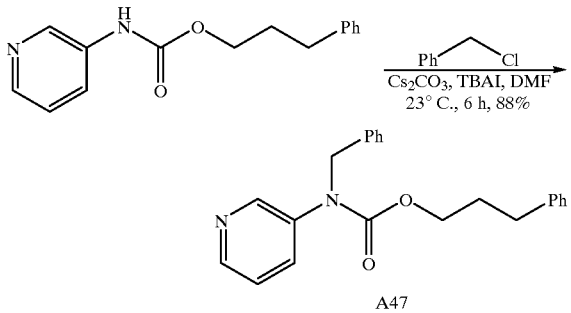

A47

Preparation of dialkyl carbamate A47: Under a nitrogen atmosphere, pyridine carbamate A7 (0.04 g, 0.16 mmol) is dissolved in anhydrous N,N-dimethylformamide (3 mL) and with vigorous stirring, cesium carbonate (0.15 g, 0.48 mmol, 3 eq.) and tetrabutylammonium iodide (0.17 g, 0.48 mmol, 3 eq.) are added to the solution and stirred for 30 minutes at ambient temperature. After stirring for 30 minutes, benzyl chloride (0.059 g, 0.48 mmol, 3 eq.) is then added into the suspension. The reaction is allowed to proceed at room temperature with continual stirring for 6 hours. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (5:1 hexanes:EtOAc) afforded carbamate A47 (0.044 g, 88%) as an oil. Data for A47: IR (thin film) 3400, 3085, 3061, 3028, 2953, 2926, 2853, 1950, 1707, 1584, 1575, 1480, 1453, 1429, 1401, 1370, 1288, 1225 cm$^{-1}$. $^1$H NMR (360 MHz, CDCl$_3$) δ1.81 (m, 2H), 2.46, (t, 2H, J=7.16 Hz), 4.07–4.08 (m, 2H), 4.80 (s, 2H), 6.98–7.36 (m, 12H), 8.37 (m, 2H). $^{13}$C NMR (90 MHz, CDCl$_3$) δ30.36, 31.95, 53.88, 65.45, 125.92, 127.59, 128.29, 128.35, 128.63, 137.18, 140.99, 155.40.

EXAMPLE 95

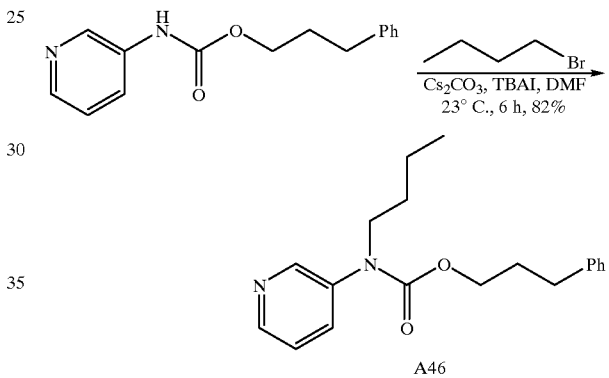

A46

Preparation of dialkyl carbamate A46: Under a nitrogen atmosphere, pyridine carbamate A7 (0.04 g, 0.16 mmol) is dissolved in anhydrous N,N-dimethylformamide (3 mL) and with vigorous stirring, cesium carbonate (0.15 g, 0.48 mmol, 3 eq.) and tetrabutylammonium iodide (0.17 g, 0.48 mmol, 3 eq.) are added to the solution and stirred for 30 minutes at ambient temperature. After stirring for 30 minutes, 1-bromobutane (0.064 g, 0.48 mmol, 3 eq.) is then added into the suspension. The reaction is allowed to proceed at room temperature with continual stirring for 6 hours. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (5:1 hexanes:EtOAc) afforded carbamate A46 (0.04 g, 82%) as an oil. Data for A46: IR (thin film) 3396, 3084, 3060, 3027, 2957, 2930, 2871, 1707, 1584, 1481, 1403, 1292, 1154cm$^{-1}$. $^1$H NMR(360 MHz, CDCl$_3$) δ0.81 (t, 3H, J=7.20 Hz), 1.17–1.26 (m, 2H), 1.41–1.47 (m, 2H), 1.81–1.82 (m, 2H (m, 2H), 3.59 (t, 2H, J=7.38 Hz), 4.03 (m, 2H), 7.02–7.47 (m, 7H), 8.42 (m, 2H). $^{13}$C NMR (90 MHz, CDCl$_3$) δ13.69, 19.76, 30.42, 32.03, 49.89, 65.09, 123.48, 125.92, 128.28, 128.35, 134.35, 141.06, 147.28, 155.18.

EXAMPLE 96

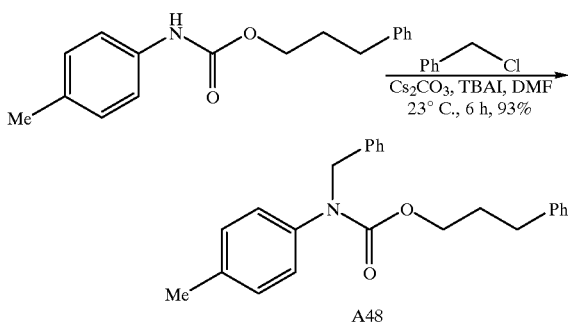

Preparation of dialkyl carbamate A48: Under a nitrogen atmosphere, p-toluidine carbamate A4 (0.07 g, 0.26 mmol) is dissolved in anhydrous N,N-dimethylformamide (3 mL) and with vigorous stirring, cesium carbonate (0.25 g, 0.78 mmol, 3 eq.) and tetrabutylammonium iodide (0.29 g, 0.78 mmol, 3 eq.) are added to the solution and stirred for 30 minutes at ambient temperature. After stirring for 30 minutes, benzyl chloride (0.1 g, 0.78 mmol, 3 eq.) is then added into the suspension. The reaction is allowed to proceed at room temperature with continual stirring for 6 hours. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (5:1 hexanes:EtOAc) afforded carbamate A48 (0.087 g, 93%) as an oil. Data for A48: IR (thin film) 3389, 3085, 3061, 3028, 2948, 2923, 2859, 1948, 1699, 1604, 1514, 1495, 1401, 1370, 1291, 1225, cm$^{-1}$ $^1$H NMR (360 MHz, CDCl$_3$) δ1.82 (m, 2H), 2.26 (s, 3H), 2.46–2.50 (m, 2H), 4.08 (m, 2H), 4.70 (s, 2H), 6.96–7.23 (m, 14H). $^{13}$C NMR (90 MHz, CDCl$_3$) 20.96, 30.56, 31.97, 54.23, 64.91, 125.83, 127.19, 128.30, 128.35, 129.41, 129.55, 138.08, 141.30, 155.91.

EXAMPLE 97

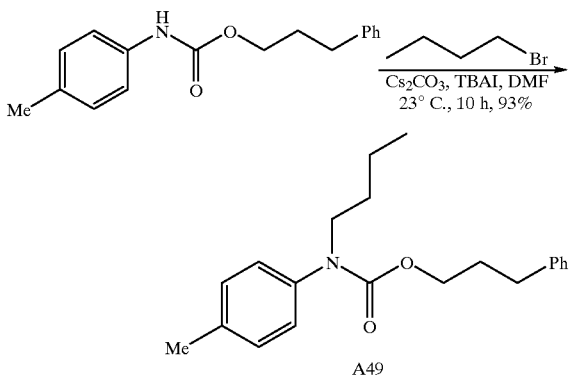

Preparation of dialkyl carbamate A49: Under a nitrogen atmosphere, p-toluidine carbamate A4 (0.05 g, 0.19 mmol) is dissolved in anhydrous N,N-dimethylformamide (3 mL) and with vigorous stirring, cesium carbonate (0.18 g, 0.57 mmol, 3 eq.) and tetrabutylammonium iodide (0.18 g, 0.57 mmol, 3 eq.) are added to the solution and stirred for 30 minutes at ambient temperature. After stirring for 30 minutes, 1-bromobutane (0.077 g, 0.57 mmol, 3 eq.) is then added into the suspension. The reaction is allowed to proceed at room temperature with continual stirring for 10 hours. The reaction mixture is quenched with water and extracted with ethyl acetate (3×30 mL). The combined organic layers are washed with water (2×30 mL), brine (30 mL) and dried over anhydrous sodium sulfate. Evaporation of the solvent and subjection of the crude residue to column chromatography (5:1 hexanes:EtOAc) afforded carbamate A49 (0.06 g, 93%) as an oil. Data for A49: IR (thin film) 3389, 3084, 3061, 3027, 2956, 2930, 2870, 1702, 1604, 1514, 1453, 1413, 1371, 1294, 1273, 1216, 1152, 1019 cm$^{-1}$. $^1$H NMR (360 MHz, CDCl$_3$) δ0.84 (t, 3H, J=7.2 Hz), 1.23–1.29 (m, 2H), 1.47 (m, 2H), 1.82 (m, 2H), 2.29 (s, 3H), 2.54 (m, 2H), 3.56–3.60 (m, 2H), 4.03 (m, 2H), 7.03–7.20 (m, 9H). $^{13}$C NMR (90 MHz, CDCl$_3$) δ13.75, 19.83, 20.97, 30.35, 30.61, 32.02, 50.05, 64.53, 125.81, 127.11, 128.29, 128.33, 129.46, 141.37, 155.67.

EXAMPLE 98

Synthesis of Silylcarbamates

In a further embodiment of the present invention, organic electrophiles are used that provide carbamates in which the ester oxygen bridges to an element other than carbon. Use of silicon-based organic electrophiles in the present invention, such as tri-isopropylsilicon chloride (TIPS), result in facile silylcarbamate formation in good yield under mild reaction conditions (FIG. 5).

EXAMPLE 98

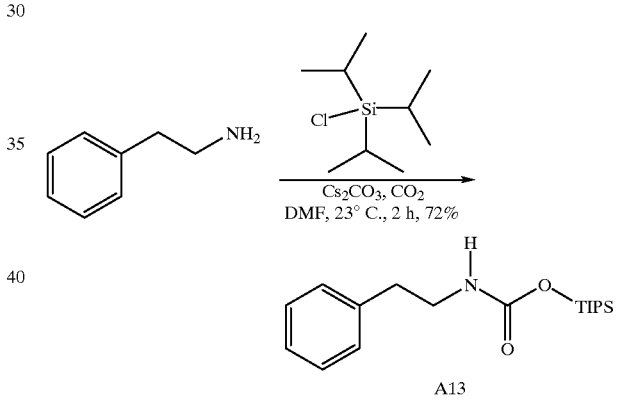

Preparation of carbamate A13. To a solution of phenethylamine (0.25 g, 1 mmol) in anhydrous N,N-dimethylformamide (20 mL), cesium carbonate (0.98 g, 1.5 mmol, 1.5 eq.) is added to the solution with vigorous stirring. Carbon dioxide is bubbled into the solution continuously for 1 hour before triisopropylsilyl chloride (0.23 g, 1.2 mmol, 1 eq.) is added. The reaction is allowed to proceed at room temperature with constant carbon dioxide bubbling and stirring for 2 hours at which point the amine is consumed. The reaction mixture is quenched with water and extracted with dichloromethane (3×30 mL), bicarbonate (30 mL), brine (30 mL) and dried over anhydrous sodium sulfate. Evaporation of the solvent and subjection of the crude residue to column chromatography (5:1 hexanes:EtOAc) affords silyl carbamate A13 (0.38 g, 72%) as a pale yellow oil. Data for A13: IR (thin film) 3360, 3300, 3085, 3063, 3027, 2942, 2891, 2865, 1679, 1497, 1463, 1259 cm$^{-1}$. $^1$H NMR (360 MHz, CDCl$_3$) δ1.01 (m, 21H), 2.71 (t, 2H, J=7.13 Hz), 3.30 (q, 2H, J=6.91 Hz), 7.08–7.22 (m, 6H) $^{13}$C NMR (90 MHz, CDCl$_3$) δ12.05, 17.76, 36.09, 42.32, 126.33, 128.49, 128.79, 157.06.

In Summary, a method is disclosed for the mild and simple syntheses of carbamates, both in solution and on solid phases, utilizing a three component coupling of an amine, carbon dioxide, and an electrophile. This methodology provides a general synthesis scheme for carbamates for a variety of applications, including peptidomimetic synthesis, combinatorial library synthesis, drug design, protection of groups, and the like.

It should be apparent to those of ordinary skill that the examples disclosed herein adequately support the use of cesium bases to promote synthesis of carbamates in general, including silylcarbamates.

It should also be apparent that other embodiments of the present invention can be readily contemplated by those of ordinary skill in the art after reviewing the present specification and teachings. The present invention is not limited, however, to the specific embodiments disclosed herein and should not be construed so narrowly as to exclude embodiments that fall within the scope and spirit of the invention, which invention is limited solely by the scope of the following claims.

What is claimed is:

1. A method for synthesis of carbamates of the formula: RR'—N—CO$_2$—R", wherein said method comprises:
providing an anhydrous solvent containing an amount of a cesium base sufficient to promote carbamate synthesis; and
reacting together in said solvent an amine, RR'—NH, an electrophile, R"—X, and carbon dioxide dissolved therein, wherein R, R', and R" are each selected independently from the group consisting of hydrogen, alkyl having 1–18 carbon atoms, silyl, phenyl, benzyl, cyclopentyl, cyclohexyl, cycloheptyl, cyclooctyl, allyl, and heterocycle, wherein X is an organic halide, an organic electrophile comprising a mesyl group, an organic electrophile comprising a tosyl group, or a silyl halide.

2. The method of claim 1, further comprising the step of increasing the concentration of said carbon dioxide in said solvent.

3. The method of claim 2, wherein said step comprises bubbling a gas containing carbon dioxide through said solvent.

4. The method of claim 1, wherein said X is chloride, bromide, iodide, O-Ms, or O-Ts.

5. The method of claim 1, wherein said cesium base is cesium carbonate.

6. The method of claim 1, wherein said solvent comprises a polar aprotic solvent.

7. The method of claim 6, wherein said polar aprotic solvent is dimethyl sulfoxide, N, N-dimethylformamide, 1-methyl-2-pyrrolidinone, N,N-dimethylacetamide, or mixtures thereof.

8. The method of claim 1, wherein said electrophile is attached to a solid support.

9. The method of claim 1, wherein said amine is attached to a solid support.

10. The method of claim 8, wherein said solid support is a resin.

11. The method of claim 7, further comprising the step of chemically cleaving said carbamate from said solid support.

12. The method of claim 1, wherein said solvent further comprises an effective amount of a compound that enhances carbamation and suppresses N-alkylation of said carbamate by said electrophile.

13. The method of claim 12, wherein said compound that enhances carbamation and suppresses N-alkylation comprises a quaternary ammonium salt.

14. The method of claim 13, wherein said quaternary ammonium salt is tributylammonium iodide.

15. A method for synthesis of N-alkylated carbamates of the formula: RR"—N—CO$_2$—R", wherein said method comprises:
reacting together in said solvent an amine, R—NH$_2$, an excess of an electrophile, R"—X, and carbon dioxide dissolved therein, wherein R, and R" are each selected independently from the group consisting of hydrogen, alkyl having 1–18 carbon atoms, silyl, phenyl, benzyl, cyclopentyl, cyclohexyl, cycloheptyl, cyclooctyl, allyl, and heterocycle, wherein X is an organic halide, an organic electrophile comprising a mesyl group, an organic electrophile comprising a tosyl group, or a silyl halide.

16. A method for synthesis of N-alkylated carbamates of the formula: RR'—N—CO$_2$—R", wherein said R' and said R" are non-identical, and wherein said method comprises: providing an anhydrous solvent containing an amount of a cesium base sufficient to promote carbamate synthesis, and further comprising an amount of a cesium base sufficient to promote carbamate synthesis, and further comprising a sufficient amount of tributylammonium iodide effective to suppress N-alkylation of said carbamate;
reacting in said solvent an amine, R—NH$_2$, an electrophile, R"—X, and carbon dioxide, wherein R, R' and R" are substituents each independently selected from the group consisting of hydrogen, alkyl having 1–18 carbon atoms, silyl, phenyl, benzyl, cyclopentyl, cyclohexyl, cycloheptyl, cyclooctyl, allyl, and heterocycle, wherein X is an organic halide, an organic electrophile comprising a mesyl group, an organic electrophile comprising a tosyl group, or a silyl halide, whereby an intermediate carbamate, R—NH—CO$_2$—R" is substantially formed; and
alkylating said intermediate carbamate by adding an effective amount of an electrophile R'X.

17. The method as in claim 8 wherein said carbamate is a peptidomimetic.

18. The method as in claim 1 wherein said carbamate is a silyl carbamate.

19. The method as in claim 1 wherein said carbamate exhibits one or more chiral centers.

* * * * *